(12) United States Patent
Lee et al.

(10) Patent No.: US 12,389,794 B2
(45) Date of Patent: Aug. 12, 2025

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Su-Hyun Lee, Gyeonggi-do (KR); Bitnari Kim, Gyeonggi-do (KR); Hyo-Nim Shin, Gyeonggi-do (KR); Jeong-Eun Yang, Gyeonggi-do (KR); Sang-Hee Cho, Gyeonggi-do (KR); Tae-Jun Han, Gyeonggi-do (KR); Hyo-Soon Park, Gyeonggi-do (KR); So-Young Jung, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 681 days.

(21) Appl. No.: 17/263,137

(22) PCT Filed: Jul. 24, 2019

(86) PCT No.: PCT/KR2019/009166
§ 371 (c)(1),
(2) Date: Jan. 25, 2021

(87) PCT Pub. No.: WO2020/022769
PCT Pub. Date: Jan. 30, 2020

(65) Prior Publication Data
US 2021/0151693 A1 May 20, 2021

(30) Foreign Application Priority Data

Jul. 25, 2018 (KR) .................. 10-2018-0086830
Jul. 23, 2019 (KR) .................. 10-2019-0088681

(51) Int. Cl.
| | | |
|---|---|---|
| H10K 85/60 | (2023.01) | |
| C07D 209/94 | (2006.01) | |
| C07D 403/04 | (2006.01) | |
| C07D 403/10 | (2006.01) | |
| C07D 405/04 | (2006.01) | |
| C07D 405/10 | (2006.01) | |
| C07D 405/14 | (2006.01) | |
| C07D 409/10 | (2006.01) | |
| C07D 487/16 | (2006.01) | |
| C09K 11/06 | (2006.01) | |
| H10K 50/11 | (2023.01) | |
| H10K 101/00 | (2023.01) | |
| H10K 101/10 | (2023.01) | |

(52) U.S. Cl.
CPC ....... *H10K 85/6572* (2023.02); *C07D 209/94* (2013.01); *C07D 403/04* (2013.01); *C07D 403/10* (2013.01); *C07D 405/04* (2013.01); *C07D 405/10* (2013.01); *C07D 405/14* (2013.01); *C07D 409/10* (2013.01); *C07D 487/16* (2013.01); *C09K 11/06* (2013.01); *H10K 85/615* (2023.02); *H10K 85/626* (2023.02); *H10K 85/636* (2023.02); *H10K 85/654* (2023.02); *H10K 85/6574* (2023.02); *H10K 85/6576* (2023.02); *C09K 2211/1018* (2013.01); *H10K 50/11* (2023.02); *H10K 2101/10* (2023.02); *H10K 2101/90* (2023.02)

(58) Field of Classification Search
CPC .............. H10K 85/6572; H10K 50/11; H10K 2101/10; H10K 2101/90; H10K 85/657; H10K 85/615; H10K 85/626; H10K 85/636; H10K 85/654; H10K 85/6574; H10K 85/6576; C07D 209/94; C07D 403/04; C07D 403/10; C07D 405/04; C07D 405/10; C07D 405/14; C07D 409/10; C07D 487/16; C09K 11/06; C09K 2211/1018
See application file for complete search history.

(56) References Cited

U.S. PATENT DOCUMENTS

| | | | |
|---|---|---|---|
| 9,397,307 B2 | 7/2016 | Nishimura et al. | |
| 2016/0028021 A1* | 1/2016 | Zeng | ............ H10K 85/342 |
| | | | 252/301.16 |
| 2016/0163998 A1 | 6/2016 | Saito et al. | |
| 2016/0181548 A1 | 6/2016 | Parham et al. | |
| 2016/0233436 A1 | 8/2016 | Zeng et al. | |

(Continued)

FOREIGN PATENT DOCUMENTS

| | | |
|---|---|---|
| CN | 105693631 A | 6/2016 |
| CN | 105753849 A | 7/2016 |

(Continued)

OTHER PUBLICATIONS

Jiang, Zhong-Lin, et al. "The influence of the mixed host emitting layer based on the TCTA and TPBi in blue phosphorescent OLED." Optics Communications 372 (2016): 49-52. (Year: 2016).*

*Primary Examiner* — Dawn L Garrett
(74) *Attorney, Agent, or Firm* — G. Creston Campbell

(57) ABSTRACT

The present disclosure relates to a plurality of host materials comprising a first host material comprising a compound represented by the following formula 1, and a second host material comprising a compound represented by the following formula 2, and an organic electroluminescent device comprising the same. By comprising a specific combination of compounds as a host material, it is possible to provide an organic electroluminescent device having higher luminous efficiency and/or improved lifespan characteristics compared to conventional organic electroluminescent devices.

9 Claims, No Drawings

(56) References Cited

U.S. PATENT DOCUMENTS

2019/0165282 A1    5/2019  Parham et al.
2019/0312212 A1   10/2019  Moon et al.
2019/0312215 A1 * 10/2019  Kang .................. H10K 85/615

FOREIGN PATENT DOCUMENTS

| KR | 20120033017 A    |  4/2012 | |
|----|------------------|---------|---|
| KR | 20130128322 A    | 11/2013 | |
| KR | 20150121337 A    | 10/2015 | |
| KR | 20150122343 A    | 11/2015 | |
| KR | 20160049083 A    |  5/2016 | |
| WO | WO-2018021841 A1 * | 2/2018 | ........... C07D 403/04 |
| WO | WO-2018159964 A1 * | 9/2018 | ........... C07D 209/56 |

\* cited by examiner

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

In 1987, Tang et al. of Eastman Kodak first developed a small molecule green organic electroluminescent device (OLED) of TPD/Alq3 bilayer consisting of a light-emitting layer and a charge transport layer. Since then, the research on an OLED has been rapidly carried out, and it has been commercialized. At present, phosphorous materials, which provide excellent luminous efficiency in realizing panels, are mainly used in organic electroluminescent devices. OLEDs having high luminous efficiency and/or long lifespan are required for long periods of uses and high resolution of displays.

In order to enhance luminous efficiency, driving voltage and/or lifespan, various materials or concepts for an organic layer of an organic eletroluminescent device have been proposed. However, they were not satisfactory to use practically.

U.S. Pat. No. 9,397,307 discloses an organic electroluminescent device using a compound in which dibenzofuran or dibenzothiophene is bonded to a nitrogen-containing heteroaryl directly or via a linker as a host. However, said reference does not specifically disclose the specific combination of the plurality of host materials of the present disclosure, and development of a host material for improving performances of an OLED is still required.

DISCLOSURE OF INVENTION

Technical Problem

The objective of the present disclosure is to provide an organic eletroluminescent device having high luminous efficiency and/or improved lifespan characteristics by comprising a plurality of host materials comprising a specific combination of compounds.

Solution to Problem

The compound of formula 1 of the present disclosure provides slow hole mobility due to very deep HOMO (highest occupied molecular orbital) and fast electron mobility due to a nitrogen-containing moiety. Due to this imbalance of the hole and electron mobilities, improvement of luminous efficiency and lifespan characteristics is required.

As a result of intense studies, the present inventors found that introducing a combination of a compound of formula 1 and a compound of formula 2, which has fast hole mobility, could provide positive influence on the hole transport property. As a result, high efficiency and long lifespan due to increase of exciton formation in the light-emitting layer could be accomplished by using the combination of the compounds of formulas 1 and 2 in an OLED.

The present inventors found that the objective above can be achieved by a plurality of host materials comprising a first host material comprising a compound represented by the following formula 1, and a second host material comprising a compound represented by the following formula 2:

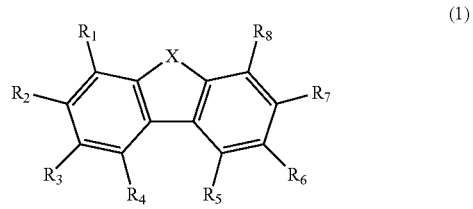

wherein

X represents O or S;

$R_1$ to $R_8$ each independently represent —$L_1$-HAr, hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, —$NR_9R_{10}$, or —$SiR_{11}R_{12}R_{13}$; or may be linked to an adjacent substituent to form a ring; with a proviso that at least one of $R_1$ to $R_8$ is —$L_1$-HAr;

$L_1$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene, where if a plurality of $L_1$ is present, each of $L_1$ may be the same or different;

HAr represents a substituted or unsubstituted nitrogen-containing (3- to 30-membered)heteroaryl, where if a plurality of HAr is present, each HAr may be the same or different;

wherein $L_2$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

Ar represents hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, —$NR_9R_{10}$, or —$SiR_{11}R_{12}R_{13}$; or may be linked to an adjacent substituent to form a ring;

is represented by the following formula 3 or formula 4;

(3)
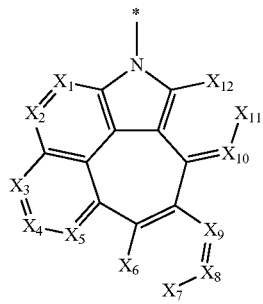

(4)
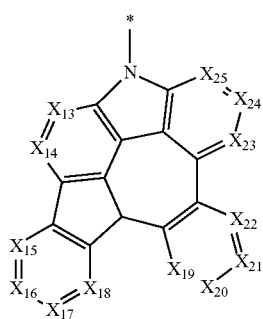

wherein $X_1$ to $X_{25}$ each independently represent N or $CR_{14}$;

$R_{14}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or adjacent $R_{14}$'s may be linked to each other to form a ring, and where if a plurality of $R_{14}$ is present, each $R_{14}$ may be the same or different;

$R_9$ to $R_{13}$ each independently represent a substituted or unsubstituted (C1-C30)alkyl, a substituted or unsubstituted (C6-C30)aryl, or a substituted or unsubstituted (3- to 30-membered)heteroaryl; and

* represents a bonding site with $L_2$.

Advantageous Effects of Invention

By comprising the plurality of host materials of the present disclosure, an organic electroluminescent device having higher luminous efficiency and/or improved lifespan characteristics compared to conventional organic electroluminescent devices can be provided, and a display device or a lighting device using the organic electroluminescent device can be manufactured.

MODE FOR THE INVENTION

Hereinafter, the present disclosure will be described in detail. However, the following description is intended to explain the disclosure, and is not meant in any way to restrict the scope of the disclosure.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (comprising a host material and a dopant material), an electron buffer material, a hole blocking material, an electron transport material, an electron injection material, etc.

The term "a plurality of organic electroluminescent materials" in the present disclosure means an organic electroluminescent material comprising a combination of at least two compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials may be a combination of at least two compounds, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. Such at least two compounds may be comprised in the same layer or different layers by a used method in the field, and may be mixture-evaporated or co-evaporated, or may be individually evaporated.

The term "a plurality of host materials" in the present disclosure means a host material comprising a combination of at least two compounds, which may be comprised in any light-emitting layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of host materials of the present disclosure may be a combination of at least two host materials, and selectively, conventional materials comprised in organic electroluminescent materials may be additionally comprised. A plurality of host materials of the present disclosure may be comprised in any light-emitting layer constituting an organic electroluminescent device, and the at least two compounds comprised in the plurality of host materials of the present disclosure may be comprised together in one light-emitting layer, or may each be comprised in separate light-emitting layers by a method known in the field. For example, the at least two compounds may be mixture-evaporated or co-evaporated, or may be individually evaporated.

Hereinafter, the compounds represented by formulas 1 and 2 will be described in detail.

Herein, the term "(C1-C30)alkyl(ene)" is meant to be a linear or branched alkyl(ene) having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl(ene)" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered) heterocycloalkyl" is meant to be a cycloalkyl having 3 to 7, preferably 5 to 7, ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms, in which the number of the ring backbone carbon atoms is preferably 6 to 25, more preferably 6 to 18. The above aryl(ene) may be partially saturated, and may comprise a spiro structure. The above aryl may include phenyl, biphenyl, terphenyl, naphthyl, binaphthyl, phenyinaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. More specifically, the above aryl may include a phenyl group, a 1-naphthyl group, a 2-naphthyl group, a 1-anthryl group, a 2-anthryl group, a 9-anthryl group, a benzanthryl group, a 1-phenanthryl group, a 2-phenanthryl group, a 3-phenanthryl group, a 4-phenanthryl group, a 9-phenanthryl group, a naphthacenyl group, a pyrenyl group, a 1-chrysenyl group, a 2-chrysenyl group, a 3-chrysenyl group, a 4-chrysenyl group, a 5-chrysenyl group, a 6-chrysenyl group, a benzo[c]phenanthryl group, a benzo[g]chrysenyl group, a 1-triphenylenyl group, a 2-triphenylenyl group, a 3-triphenylenyl group, a 4-triphenylenyl group, a 1-fluorenyl group, a 2-fluorenyl group, a 3-fluorenyl group, a 4-fluorenyl group, a 9-fluorenyl group, a benzofluorenyl group, a dibenzofluorenyl group, a 2-biphenylyl group, a 3-biphenylyl group, a 4-biphenylyl group, an o-terphenyl group, an m-terphenyl-4-yl group, an m-terphenyl-3-yl group, an m-terphenyl-2-yl group, a p-terphenyl-4-yl group, a p-terphenyl-3-yl group, a p-terphenyl-2-yl group, an m-quaterphenyl group, a 3-fluoranthenyl group, a 4-fluoranthenyl group, an 8-fluoranthenyl group, a 9-fluoranthenyl group, a benzofluoranthenyl group, an o-tolyl group, an m-tolyl group, a p-tolyl group, a 2,3-xytyl group, a 3,4-xylyl group, a 2,5-xylyl group, a mesityl group, an o-cumenyl group, an m-cumenyl group, a p-cumenyl group, a p-t-butylphenyl group, a p-(2-phenylpropyl)phenyl group, a 4'-methylbiphenylyl group, a 4"-t-butyl-p-terphenyl-4-yl group, a 9,9-dimethyl-1-fluorenyl group, a 9,9-dimethyl-2-fluorenyl group, a 9,9-dimethyl-3-fluorenyl group, a 9,9-dimethyl-4-fluorenyl group, a 9,9-diphenyl-1-fluorenyl group, a 9,9-diphenyl-2-fluorenyl group, a 9,9-diphenyl-3-fluorenyl group, a 9,9-diphenyl-4-fluorenyl group, etc.

The term "(3- to 30-membered)heteroaryl(ene)" is meant to be an aryl having 3 to 30 ring backbone atoms, and including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrroyl, imidazolyl, pyrazolyl, thiazolyl, thiadiazolyl, isothiazolyl, isoxazolyl, oxazoyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzonaphthofuranyl, benzonaphthothiophenyl, diazadibenzofuranyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, benzoquinoyl, isoquinoyl, benzoisoquinolyl, cinnolinyl, quinazolinyl, benzoquinazolinyl, quinoxalinyl, benzoquinoxalinyl, naphthyridinyl, triazanaphthyl, benzothienopyrimidinyl, carbazoyl, benzocarbazoyl, dibenzocarbazoyl, phenoxazinyl, phenothiazinyl, phenanthridinyl, benzodioxolyl, dihydroacridinyl, etc. More specifically, the above heteroaryl may include a 1-pyrrolyl group, a 2-pyrrolyl group, a 3-pyrrolyl group, a pyrazinyl group, a 2-pyridinyl group, a 2-pyrimidinyl group, a 4-pyrimidinyl group, a 5-pyrimidinyl group, a 6-pyrimidinyl group, a 1,2,3-triazin-4-yl group, a 1,2,4-triazin-3-yl group, a 1,3,5-triazin-2-yl group, a 1-imidazolyl group, a 2-imidazolyl group, a 1-pyrazolyl group, a 1-indolidinyl group, a 2-indolidinyl group, a 3-indolidinyl group, a 5-indolidinyl group, a 6-indolidinyl group, a 7-indolidinyl group, an 8-indolidinyl group, a 2-imidazopyridinyl group, a 3-imidazopyridinyl group, a 5-imidazopyridinyl group, a 6-imidazopyridinyl group, a 7-imidazopyridinyl group, an 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindoyl group, a 4-isoindoyl group, a 5-isoindolyl group, a 6-isoindolyl group, a 7-isoindoyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinoyl group, an 8-quinoyl group, a 1-isoquinolyl group, a 3-isoquinolyl group, a 4-isoquinoyl group, a 5-isoquinoyl group, a 6-isoquinolyl group, a 7-isoquinolyl group, an 8-isoquinoyl group, a 2-quinoxalinyl group, a 5-quinoxalinyl group, a 6-quinoxalinyl group, a 1-carbazoyl group, a 2-carbazoyl group, a 3-carbazolyl group, a 4-carbazolyl group, a 9-carbazolyl group, an azacarbazoyl-1-yl group, an azacarbazolyl-2-yl group, an azacarbazolyl-3-yl group, an azacarbazoyl-4-yl group, an azacarbazoyl-5-yl group, an azacarbazoly-6-yl group, an azacarbazoyl-7-yl group, an azacarbazolyl-8-yl group, an azacarbazoyl-9-yl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 2-oxazoyl group, a 4-oxazolyl group, a 5-oxazolyl group, a 2-oxadiazolyl group, a 5-oxadiazoyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indoyl group, a 4-t-butyl-3-indolyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-silafluorenyl group, a 2-silafluorenyl group, a 3-silafluorenyl group, a 4-silafluorenyl group, a 1-germafluorenyl group, a 2-germafluorenyl group, a 3-germafluorenyl group, and a 4-germafluorenyl group.

Furthermore, "halogen" includes F, Cl, Br, and I.

Herein, "substituted" in the expression "substituted or unsubstituted" means that a hydrogen atom in a certain functional group is replaced with another atom or functional group, i.e., a substituent. The substituents of the substituted alkyl, the substituted alkylene, the substituted aryl, the substituted arylene, the substituted heteroaryl, the substituted heteroarylene, the substituted cycloalkyl, the substituted cycloalkylene, the substituted cycloalkenyl, the substituted heterocycloalkyl, the substituted alkoxy, the substituted trialkylsiyl, the substituted dialkylarylsilyl, the substituted alkyldiarylsilyl, the substituted triarylsiyl, the substituted mono- or di-alkylamino, the substituted mono- or di-arylamino, and the substituted alkylarylamino in the formulas of the present disclosure each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkythio; a (C3-C30)cycloalkyl; a (C3-C30)cycloalkenyl; a (3- to 7-membered)heterocycloalkyl; a (C6-C30)aryloxy; a (C6-C30)arythio; a (3- to 30-membered)heteroaryl unsubstituted or substituted with a (C6-C30)aryl(s); a (C6-C30)aryl unsubstituted or substituted with at least one of a (C1-C30)alkyl(s), a (3- to 30-membered)heteroaryl(s), and a di(C6-C30)arylamino(s); a tri(C1-C30)alkylsiyl; a tri(C6-C30)arysilyl; a di(C1-C30)alkyl(C6-C30)arylsilyl; a (C1-C30)alkyldi(C6-C30)arylsiyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. Preferably, the substituents each independently are at least one selected from the group consisting of a (C1-C10)alkyl; a (C6-C20)aryl unsubstituted or substituted with at least one of a (C1-C10)alkyl(s), a (3- to 20-membered)heteroaryl(s), and a di(C6-C20)aryl-amino(s); a (3- to 20-membered)heteroaryl unsubstituted or substituted with a (C6-C20)aryl(s); and a di(C6-C20)ary-lamino. More preferably, the substituents each independently are at least one selected from the group consisting of a (C1-C6)alkyl; a (C6-C20)aryl unsubstituted or substituted with at least one of a (C1-C6)alkyl, a (5- to 15-membered)heteroaryl, and a di(C6-C12)arylamino; a (5- to 15-membered)heteroaryl unsubstituted or substituted with a (C6-C12)aryl; and a di(C6-C12)arylamino. For example, the substituents may be at least one of a methyl, a phenyl, a naphthyl, a biphenyl, a terphenyl, a phenanthrenyl, a triphenylenyl, a naphthylphenyl, a phenylnaphthyl, a dimethylfluorenyl, a dimethylbenzofluorenyl, a phenyl substituted with a phenylquinoxalinyl, a carbazolylphenyl, a dibenzofuranylphenyl, a phenyl substituted with a diphenylamino, a phenylquinoxalinyl, a carbazolyl, a phenylcarbazolyl, a dibenzofuranyl, and a diphenylamino.

In the formulas of the present disclosure, if adjacent substituents are linked to each other to form a ring, the ring may be a substituted or unsubstituted, mono- or polycyclic, (3- to 30-membered) alicyclic or aromatic ring, or the combination thereof which is formed by the link of two or more adjacent substituents, in which the formed ring may contain at least one heteroatom selected from B, N, O, S, Si, and P, preferably N. O, and S. For example, the fused ring may be a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, the heteroaryl or heteroarylene may each independently contain at least one heteroatom selected from B, N, O, S. Si, and P. In addition, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arysilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

In formula 1, X represents O or S.

In formula 1, $R_1$ to $R_8$ each independently represent —$L_1$-HAr, hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, —$NR_9R_{10}$, or —$SiR_{11}R_{12}R_{13}$; or may be linked to an adjacent substituent to form a ring; with a proviso that at least one of $R_1$ to R is —$L_1$-HAr. According to one embodiment of the present disclosure, one of $R_1$ to $R_8$ is —$L_1$-HAr, and the others are hydrogen.

In formula 1, $L_1$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene, where if a plurality of $L_1$ is present, each of $L_1$ may be the same or different. According to one embodiment of the present disclosure, L represents a single bond, or a substituted or unsubstituted (C6-C20) arylene. According to another embodiment of the present disclosure, $L_1$ represents a single bond or an unsubstituted (C6-C20)arylene. Specifically, $L_1$ may represent a single bond, a phenylene, a naphthylene, a biphenylene, a naphthylphenylene, a phenylnaphthylene, etc.

In formula 1. HAr represents a substituted or unsubstituted nitrogen-containing (3- to 30-membered)heteroaryl, where if a plurality of HAr is present, each of HAr may be the same or different. According to one embodiment of the present disclosure, HAr represents a substituted or unsubstituted nitrogen-containing (5- to 15-membered)heteroaryl. According to another embodiment of the present disclosure, HAr represents a substituted or unsubstituted nitrogen-containing (5- to 15-membered)heteroaryl, and the substituent of the substituted nitrogen-containing (5- to 15-membered)heteroaryl may be at least one of a (C6-C20)aryl unsubstituted or substituted with at least one of a (C1-C6) alkyl(s), a (5- to 15-membered)heteroaryl(s), and a di(C6-C12)arylamino(s); a (5- to 15-membered)heteroaryl unsubstituted or substituted with a (C6-C12)aryl(s). Specifically, HAr may represent a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted triazanaphthyl, a substituted or unsubstituted benzothienopyrimidinyl, etc. For example. HAr may represent a triazinyl, a quinazolinyl, a quinoxalinyl, a naphthyridinyl, a triazanaphthyl, a benzoquinazolinyl, a benzoquinoxalinyl, etc. The triazinyl may be substituted with at least one of a phenyl, a naphthyl, a biphenyl, a terphenyl, a naphthylphenyl, a dimethylbenzofluorenyl, a dibenzofuranylphenyl, and a dibenzofuranyl, the quinazolinyl may be substituted with at least one of a phenyl and a naphthyl, the quinoxalinyl may be substituted with at least one of a phenyl, a naphthyl, a biphenyl, a terphenyl, a phenanthrenyl, a triphenylenyl, a naphthylphenyl, a phenynaphthyl, a dimethylfluorenyl, a dimethylbenzofluorenyl, a phenyl substituted with a phenylquinoxalinyl, a carbazolylphenyl, a dibenzofuranylphenyl, a phenyl substituted with a diphenylamino, a phenylcarbazolyl, and a dibenzofuranyl, the naphthyridinyl may be substituted with at least one of a phenyl, a naphthyl, a biphenyl, a dimethylfluorenyl, a dimethylbenzofluorenyl, and a phenylcarbazolyl, the triazanaphthyl may be substituted with at least one phenyl, the benzoquinazolinyl may be substituted with at least one biphenyl, and the benzoquinoxalinyl may be substituted with at least one of a phenyl, a naphthyl, a biphenyl, and a naphthylphenyl.

According to one embodiment of the present disclosure, formula 1 may be represented by at least one of the following formulas 1-1 to 1-4.

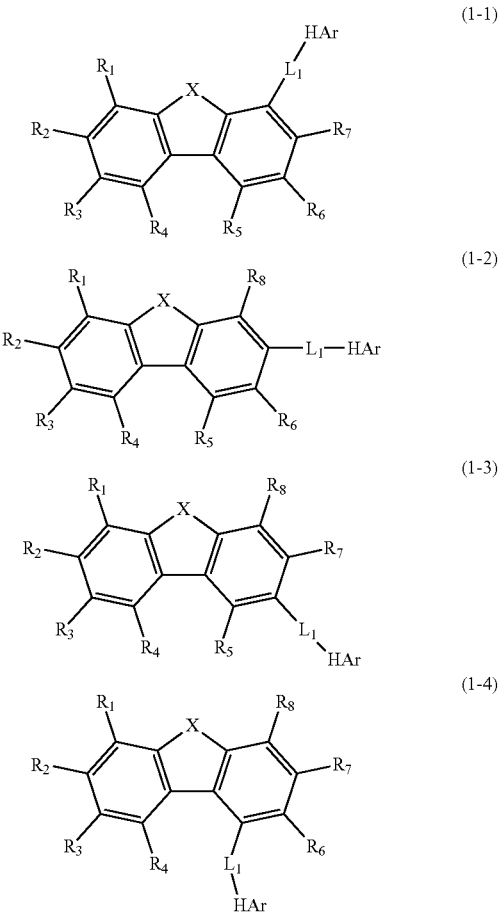

wherein
$R_1$ to $R_8$, X, $L_1$, and HAr are as defined in formula 1.

In formula 2, Ar represents hydrogen, deuterium, a halogen, a cyano, a substituted or unsubstituted (C1-C30)alkyl, a substituted or unsubstituted (C3-C30)cycloalkyl, a substituted or unsubstituted (C3-C30)cycloalkeny, a substituted or unsubstituted (3- to 7-membered)heterocycloalkyl, a substituted or unsubstituted (C6-C30)aryl, a substituted or unsubstituted (3- to 30-membered)heteroaryl, —NR$_9$R$_{10}$, or —SiR$_{11}$R$_{12}$R$_{13}$; or may be linked to an adjacent substituent to form a ring. According to one embodiment of the present disclosure, Ar represents a substituted or unsubstituted (C6-C25)aryl, a substituted or unsubstituted (5- to 15-membered) heteroaryl, or —NR$_9$R$_{10}$. Herein, R$_9$ and R$_{10}$ each independently represent a substituted or unsubstituted (C6-C12)aryl. According to another embodiment of the present disclosure, Ar represents a (C6-C25)aryl unsubstituted or substituted with at least one (C1-C6)alkyl, a(5- to 15-membered)heteroaryl unsubstituted or substituted with at least one (C6-C12)aryl, or —NR$_9$R$_{10}$. Herein, R$_9$ and R$_{10}$ each independently represent an unsubstituted (C6-C12)aryl. Specifically, Ar may represent a substituted or unsubstituted phenyl, a substituted or unsubstituted naphthyl, a substituted or unsubstituted biphenyl, a substituted or unsubstituted naphthylphenyl, a substituted or unsubstituted phenylnaphthyl, a substituted or unsubstituted terphenyl, a substituted or unsubstituted carbazolyl, a substituted or unsubstituted benzocarbazolyl, a substituted or unsubstituted dibenzocarbazolyl, a substituted or unsubstituted dibenzothiophenyl, a substituted or unsubstituted benzothiophenyl, a substituted or unsubstituted benzonaphthothiophenyl, a substituted or unsubstituted dibenzofuranyl, a substituted or unsubstituted benzofuranyl, a substituted or unsubstituted benzonaphthofuranyl, a substituted or unsubstituted diazadibenzofuranyl, a substituted or unsubstituted pyridyl, a substituted or unsubstituted pyrimidinyl, a substituted or unsubstituted triazinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted benzothienopyrimidinyl, a substituted or unsubstituted fluorenyl, a substituted or unsubstituted benzofluorenyl, a substituted or unsubstituted spirobifluorenyl, a substituted or unsubstituted diphenylamino, a substituted or unsubstituted phenylnaphthylamino, a substituted or unsubstituted phenylbiphenylamino, a substituted or unsubstituted naphthylbiphenylamino, a substituted or unsubstituted dibiphenylamino, a substituted or unsubstituted biphenylfluorenylamino, or a substituted or unsubstituted biphenyldibenzofuranylamino, etc. For example, Ar may represent a phenyl, a naphthyl, a biphenyl, a terphenyl, a spirobifluorenyl, a dimethylfluorenyl, a dimethylbenzofluorenyl, a phenylpyridyl, a diphenylpyrimidinyl, a dimethyltriazinyl, a phenylquinolyl, a diphenylquinazolinyl, a biphenylquinazolinyl, a phenylquinoxalinyl, a diphenylquinoxalinyl, a naphthylquinoxalinyl, a phenylnaphthyridinyl, a carbazoyl, a phenylcarbazolyl, a dibenzofuranyl, a phenyldibenzofuranyl, a dibenzothiophenyl, a phenyldiazadibenzofuranyl, a phenylbenzoquinazolinyl, a phenylbenzoquinoxalinyl, a diphenylamino, a phenylnaphthylamino, a phenylbiphenylamino, etc.

In formulas 3 and 4, $X_1$ to $X_{25}$ each independently represent N or $CR_{14}$. According to one embodiment of the present disclosure, $X_1$ to $X_{25}$ are all $CR_{14}$.

In formulas 3 and 4, $R_{14}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or adjacent $R_4$'s may be linked to each other to form a ring, and where if a plurality of $R_{14}$ is present, each $R_{14}$ may be the same or different. According to one embodiment of the present disclosure, $R_1$ may each independently represent hydrogen, or a substituted or unsubstituted (C6-C12)aryl, or adjacent $R_{14}$'s may be linked to each other to form a ring. According to another embodiment of the present disclosure, $R_{14}$ each independently represents hydrogen, or an unsubstituted (C6-C12)aryl, or adjacent $R_{14}$'s may be linked to each other to form a ring. Specifically, $R_{14}$ may each independently represent hydrogen, a phenyl, etc., or adjacent $R_4$'s may be linked to each other to form a benzene ring.

In formula 2, $l_2$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene. According to one embodiment of the present disclosure, $L_2$ represents a single bond, a substituted or unsubstituted (C6-C12)arylene, or a substituted or unsubstituted (5- to 15-membered)heteroarylene. According to another embodiment of the present disclosure, L represents a single bond, an unsubstituted (C6-C12) arylene, or a (5- to 15-membered)heteroarylene unsubstituted or substituted with a (C6-C12)aryl(s). Specifically, $L_2$ may represent a single bond, a phenylene, a naphthylene, a biphenylene, a phenylpyridylene, a phenyltriazinylene, a quinolylene, a quinazolinylene, a phenylquinazolinylene, a quinoxalinylene, a phenyiquinoxalinylene, a naphthyridinylene, a carbazolylene, a dibenzofuranylene, a benzoquinazolinylene, a benzoquinoxalinylene, a diazadibenzofuranylene, etc.

In formulas 1 and 2, $R_9$ to $R_{13}$ each independently represent a substituted or unsubstituted (C1-C30)alkyl, a substituted or unsubstituted (C6-C30)aryl, or a substituted or unsubstituted (3- to 30-membered)heteroaryl. According to one embodiment of the present disclosure, $R_9$ and $R_{10}$ each independently represent a substituted or unsubstituted (C6-C12)aryl. According to another embodiment of the present disclosure, $R_9$ and $R_{10}$ each independently represent an unsubstituted (C6-C12)aryl. Specifically, $R_9$ and $R_{10}$ each independently represent a phenyl, a naphthyl, a biphenyl, etc.

According to one embodiment of the present disclosure, formula 3 may be represented by the following formula 3-1:

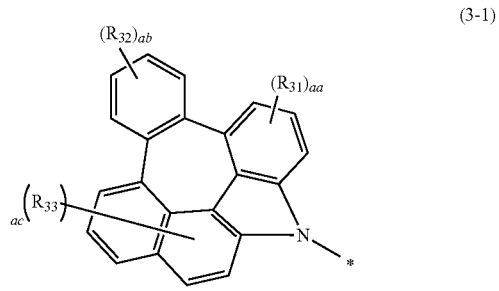

(3-1)

wherein $R_{31}$ to $R_{33}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a ring; and aa represents an integer of 1 to 3, ab represents an integer of 1 to 4, ac represents an integer of 1 to 5, where if aa, ab, and ac are an integer of 2 or more, each $R_1$, each $R_{32}$, and each $R_{33}$ may be the same or different.

According to one embodiment of the present disclosure, formula 4 may be represented by the following formula 4-1:

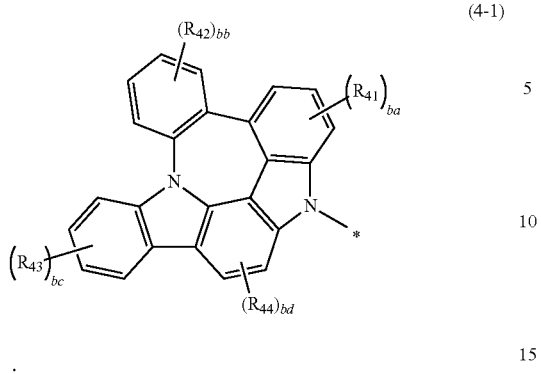

(4-1)

wherein $R_{41}$ to $R_{44}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsiyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent to form a ring; and ba represents an integer of 1 to 3, bb and bc each independently represent an integer of 1 to 4, bd represents 1 or 2, where if ba, bb, bc, and bd are an integer of 2 or more, each $R_{41}$, each $R_{42}$, each $R_{43}$, and each $R_{44}$ may be the same or different.

The compound represented by formula 1 includes the following compounds, but is not limited thereto.

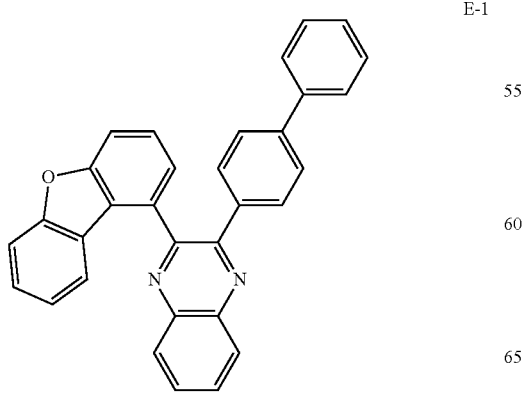

E-1

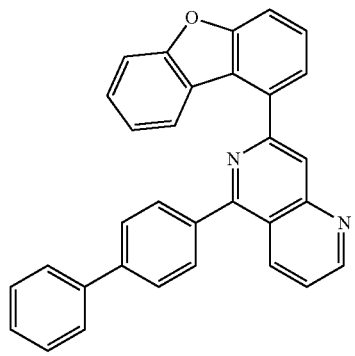

E-2

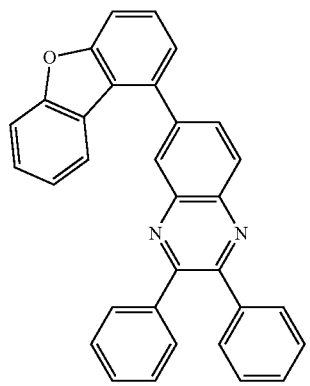

E-3

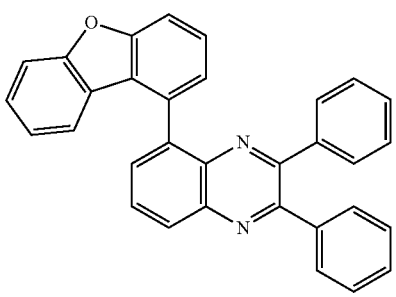

E-4

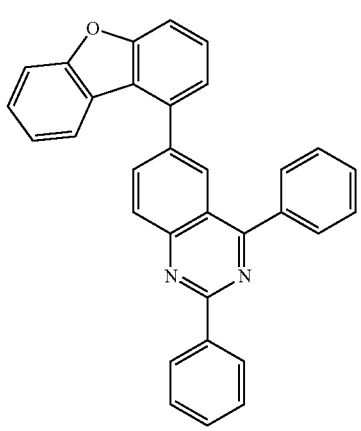

E-5

E-6
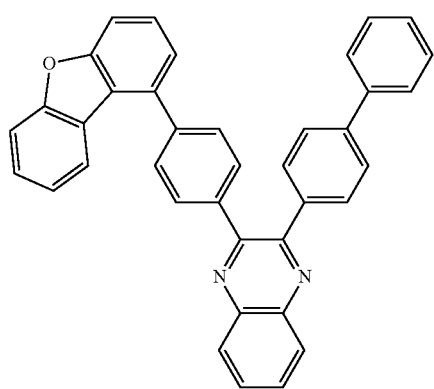
E-7
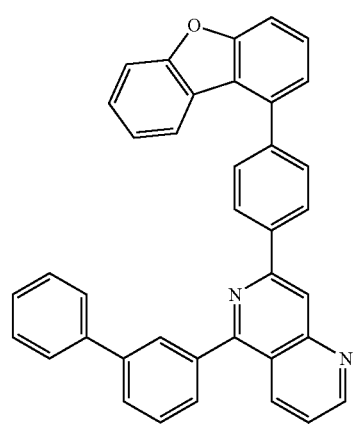
E-8
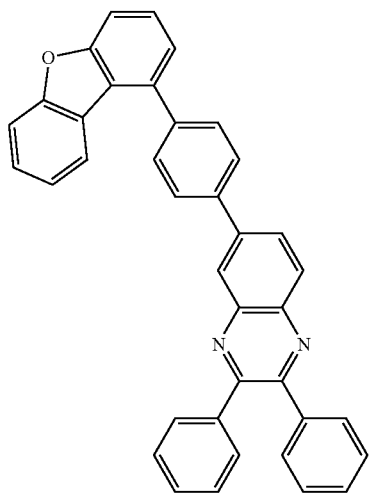
E-9
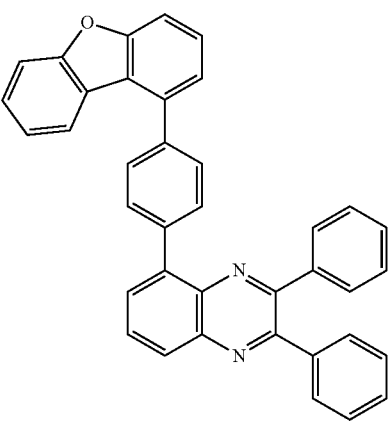
E-10
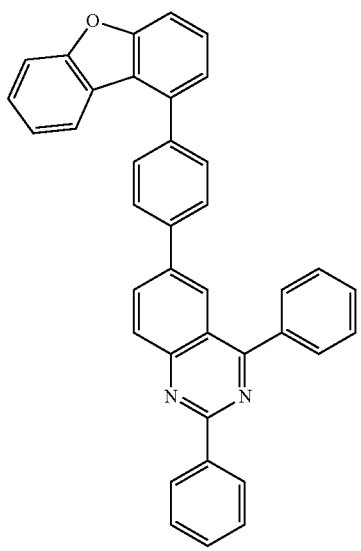
E-11

E-12
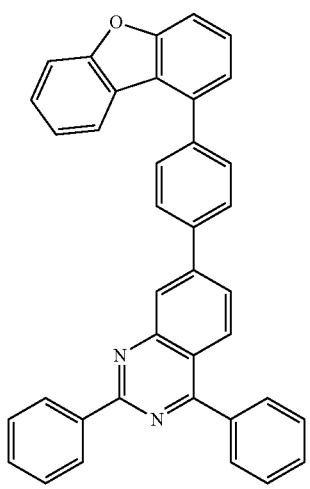
E-13
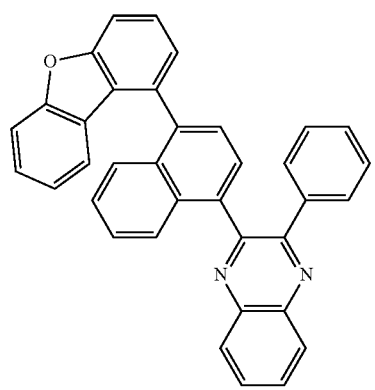
E-14
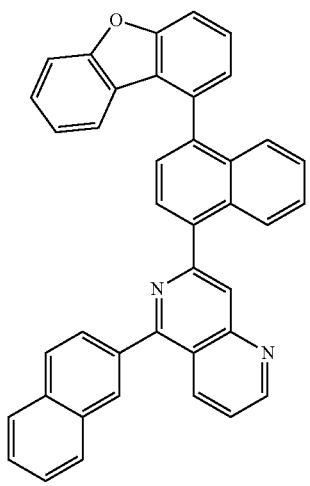
E-15
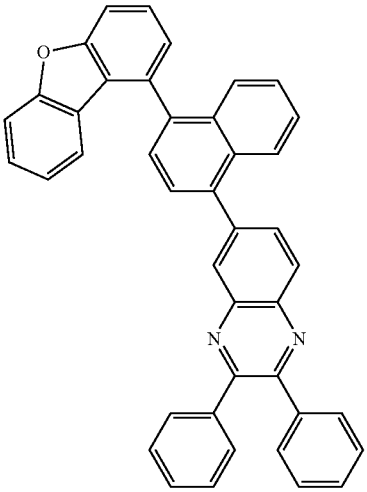
E-16
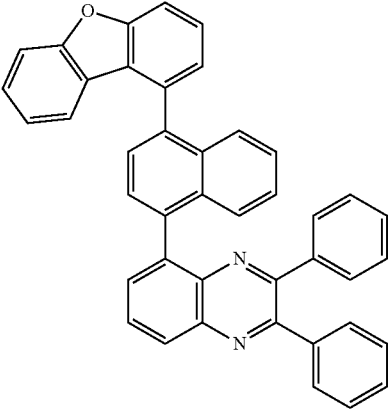
E-17
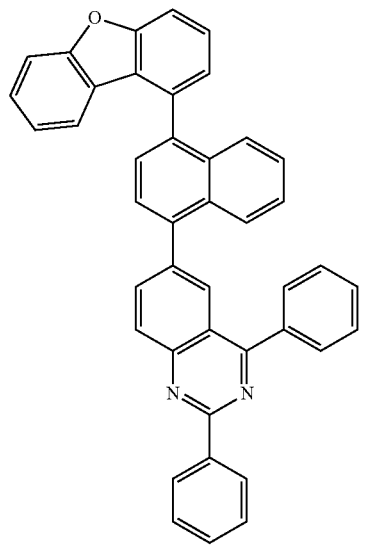

-continued
E-18
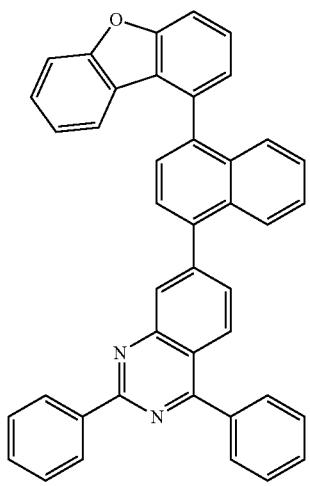
E-21
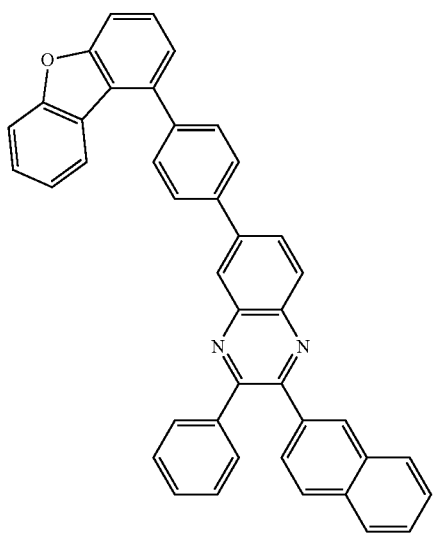
E-19
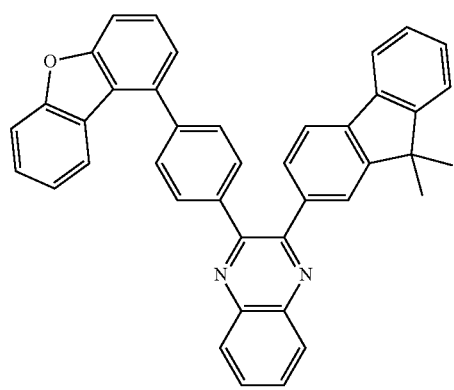
E-22
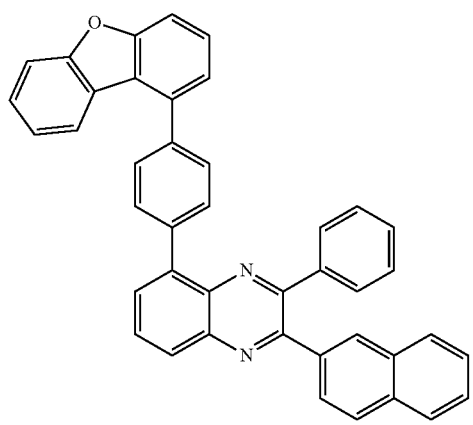
E-20
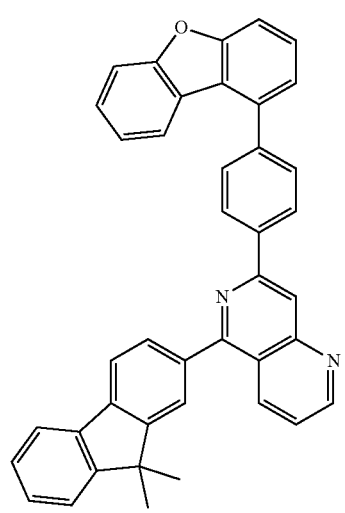
E-23
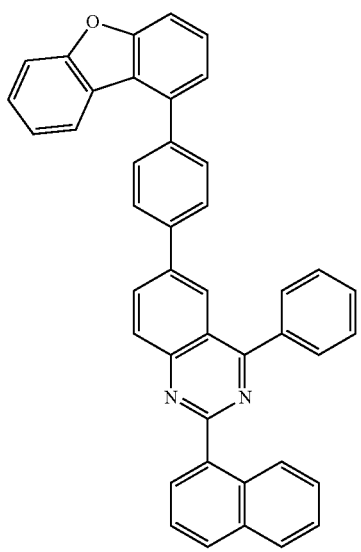

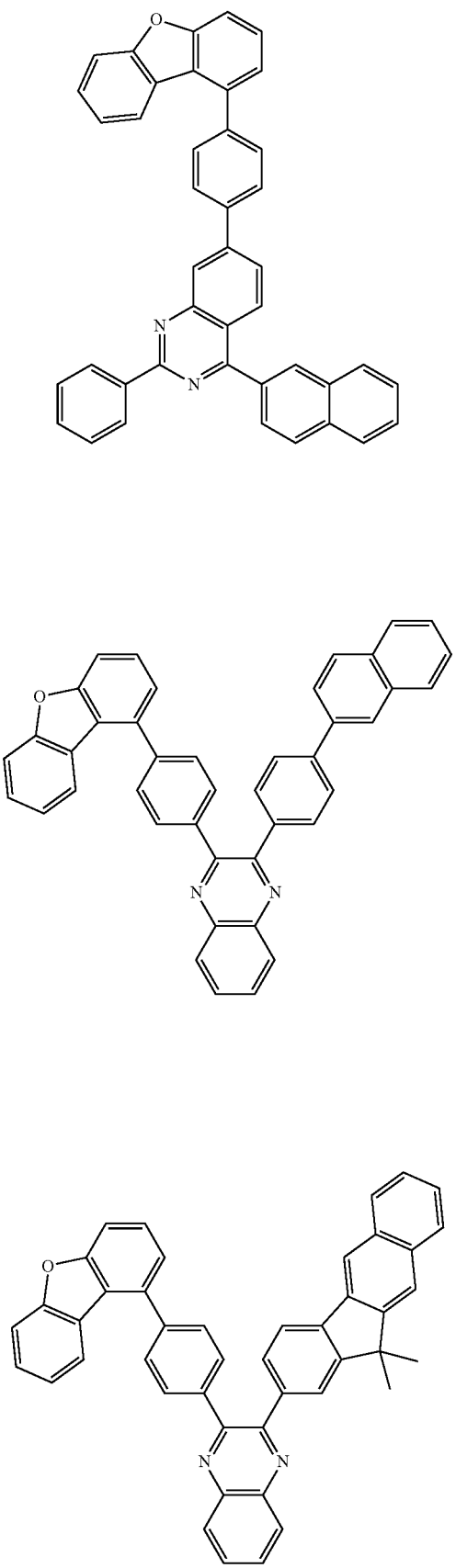

E-31
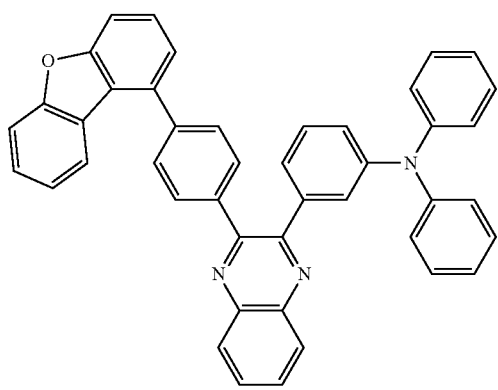
E-32
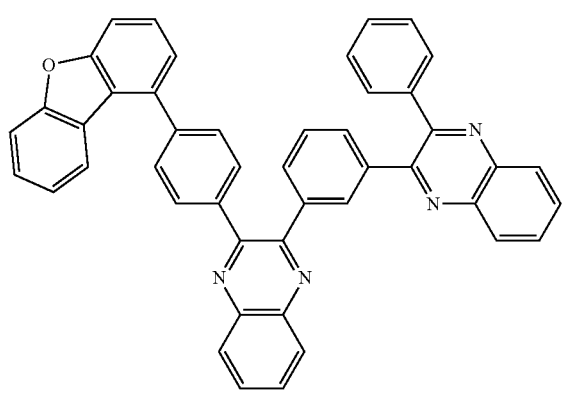
E-33
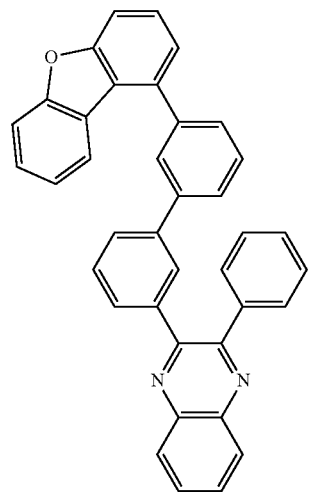
E-34
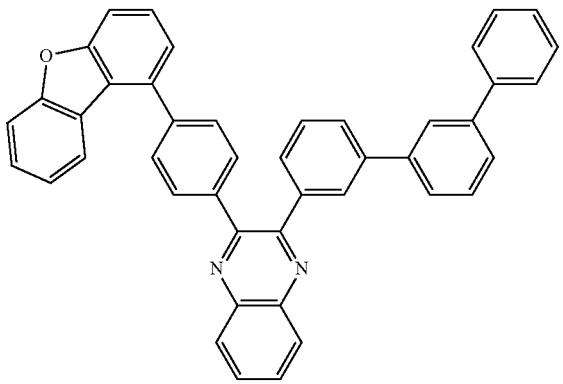
E-35
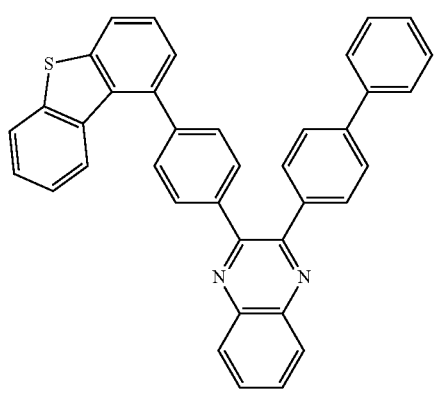
E-36
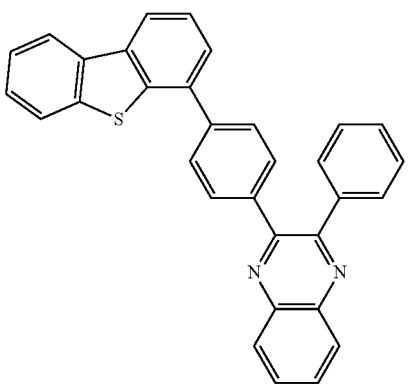
E-37
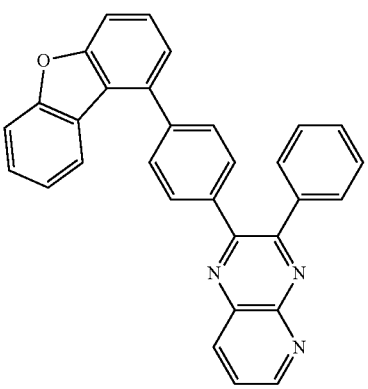

E-38
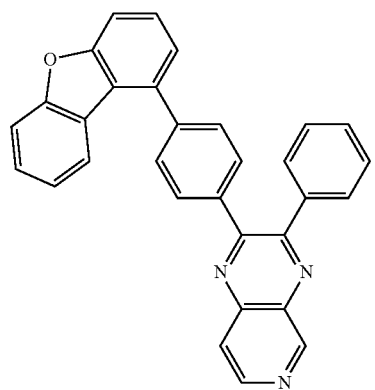
E-39
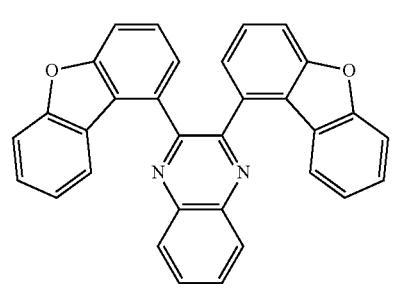
E-40
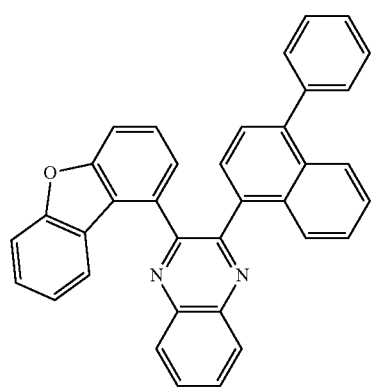
E-41
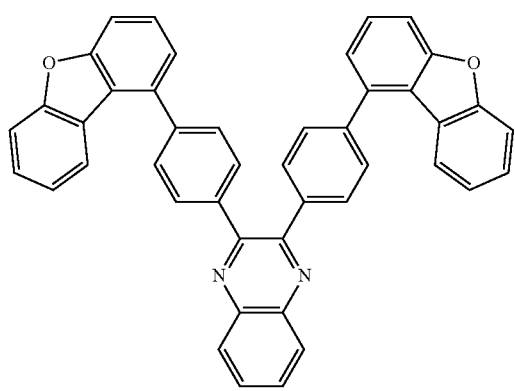
E-42
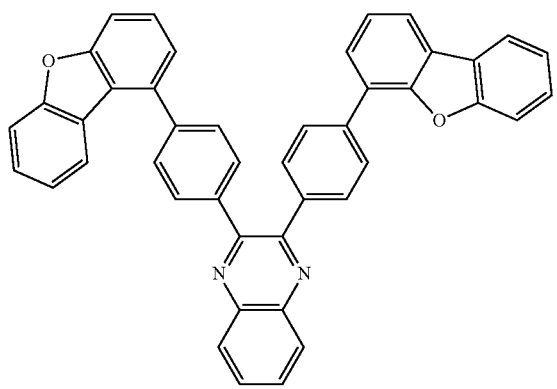
E-43
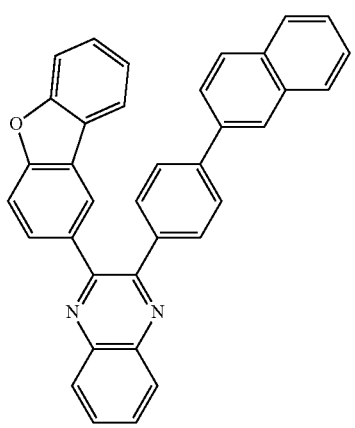
E-44
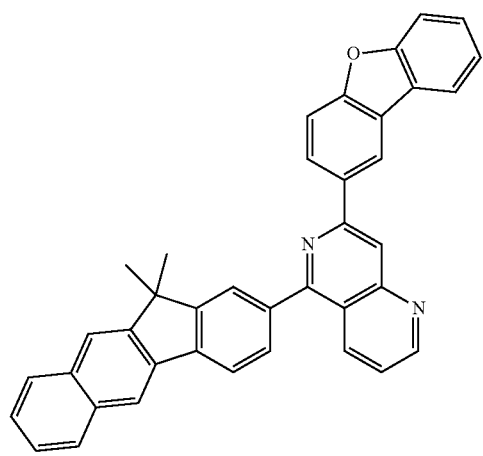

E-45
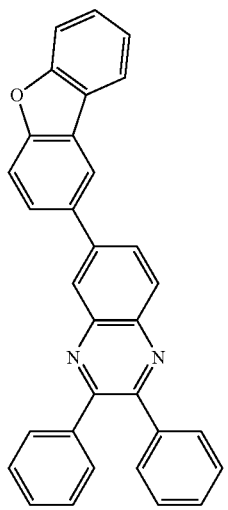
E-46
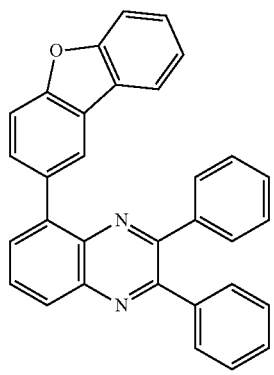
E-47
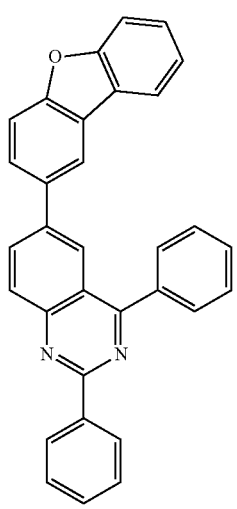
E-48
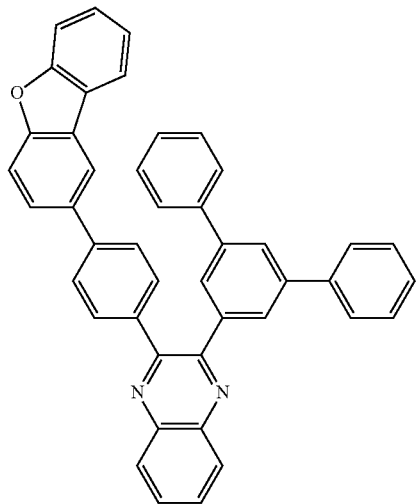
E-49
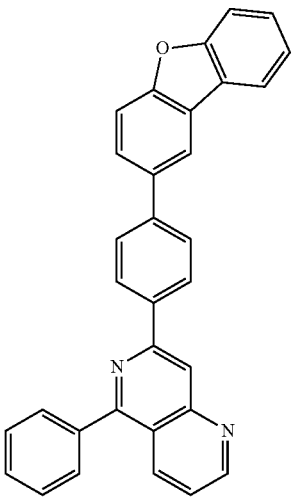
E-50
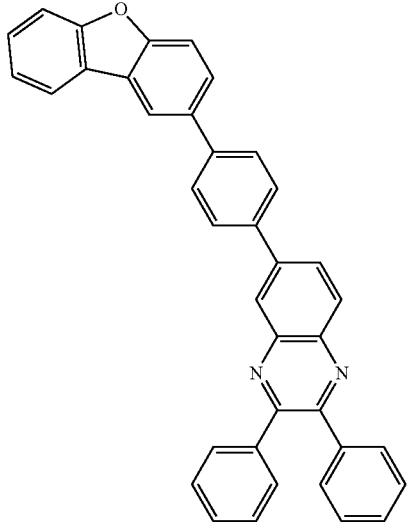

E-51
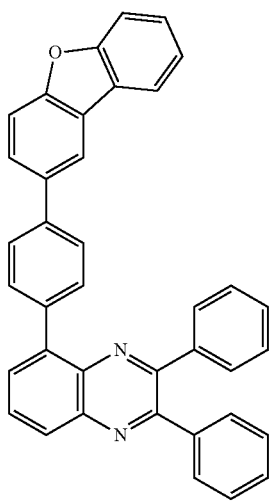
E-52
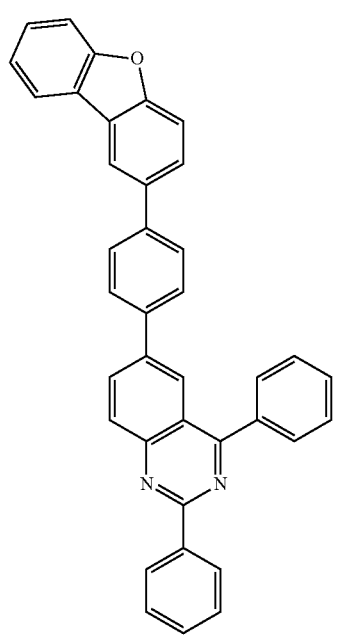
E-53
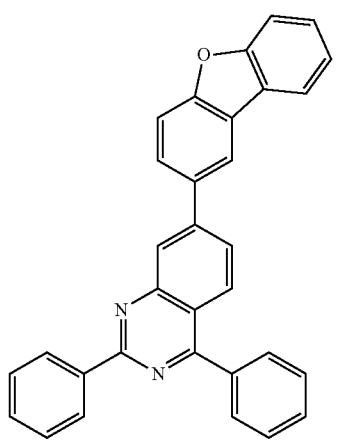
E-54
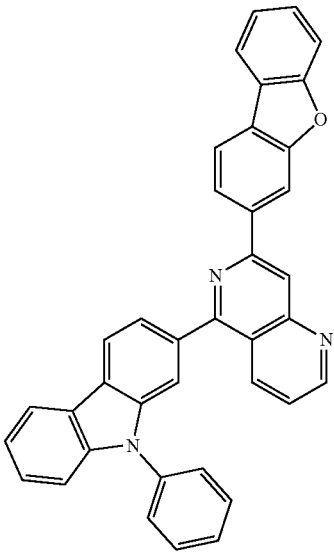
E-55
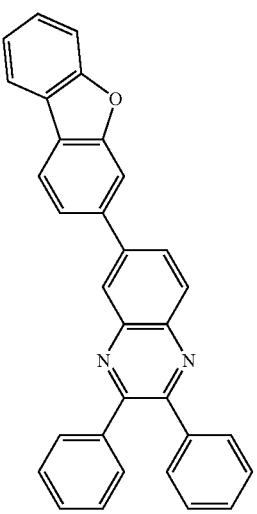
E-56
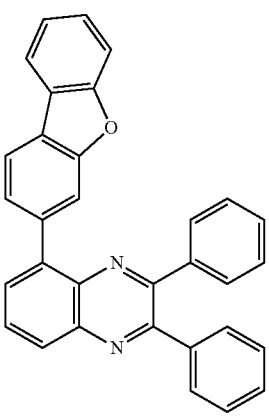

E-57
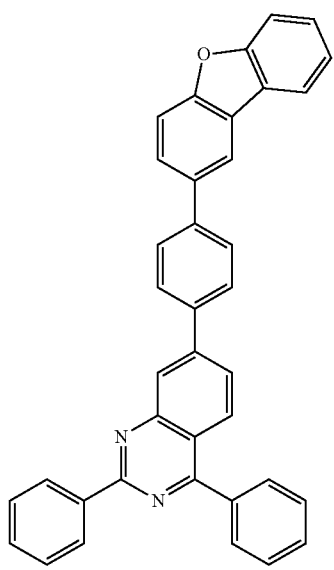
E-58
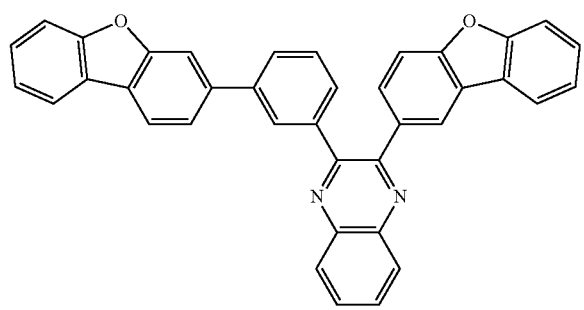
E-59
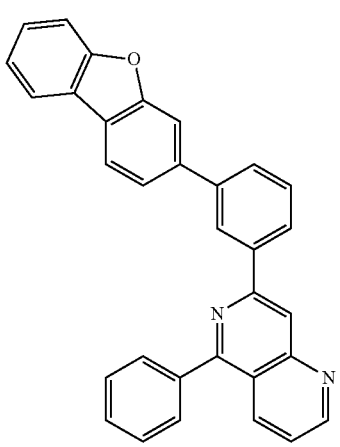
E-60
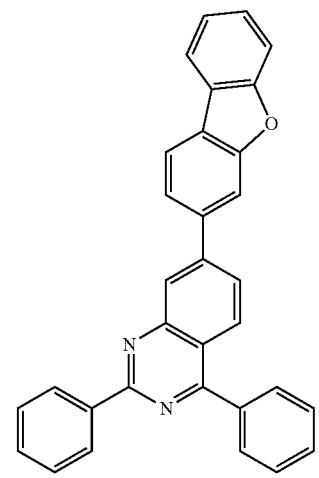
E-61
E-62

-continued
E-63
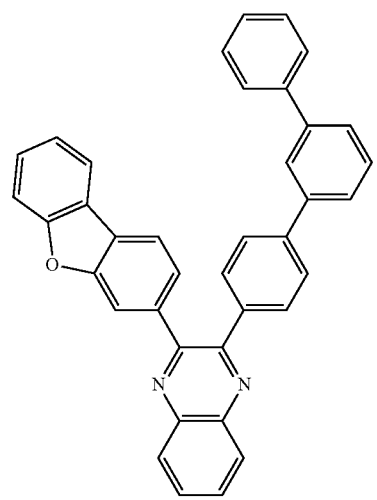
E-64
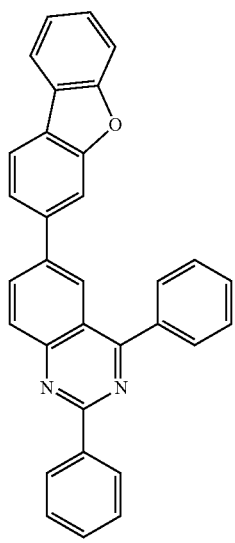
E-65
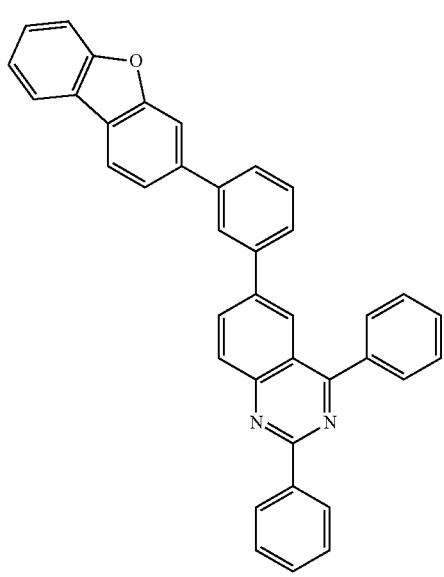
-continued
E-66
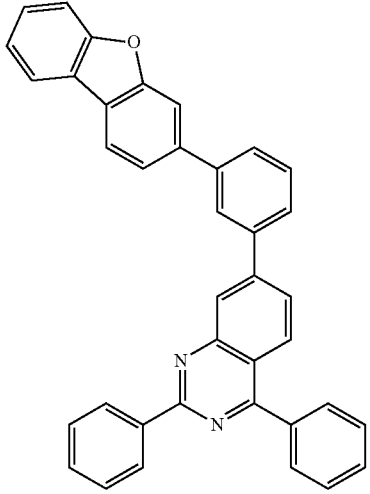
E-67
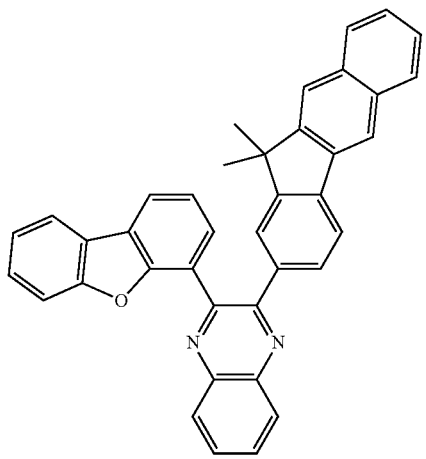
E-68
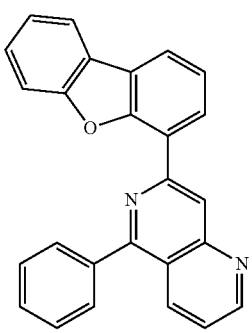

E-69
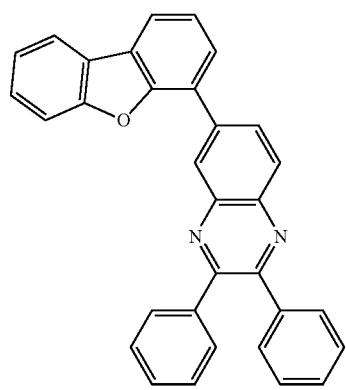
E-70
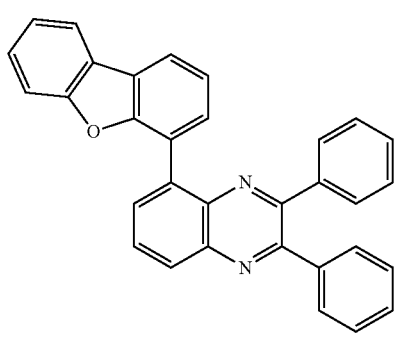
E-71
E-72
E-73
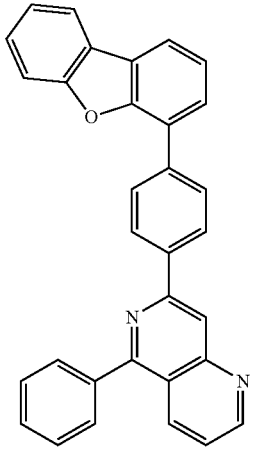
E-74
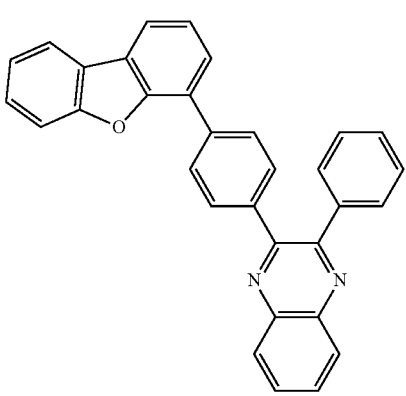
E-75
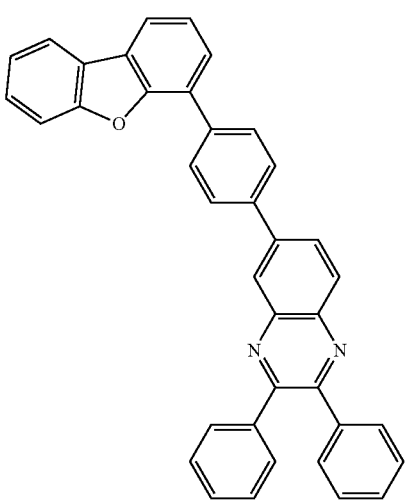

E-76
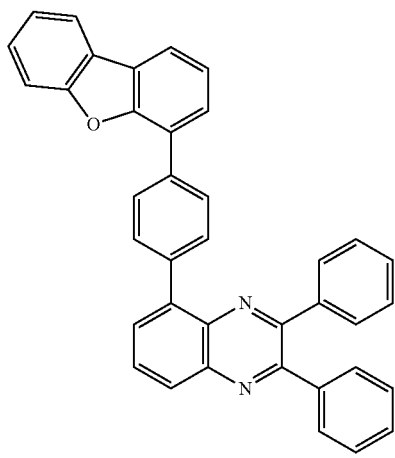
E-77
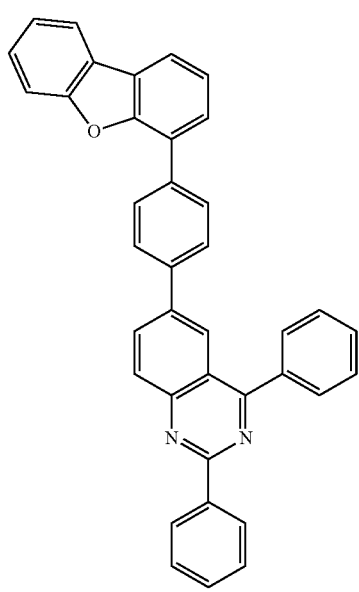
E-78
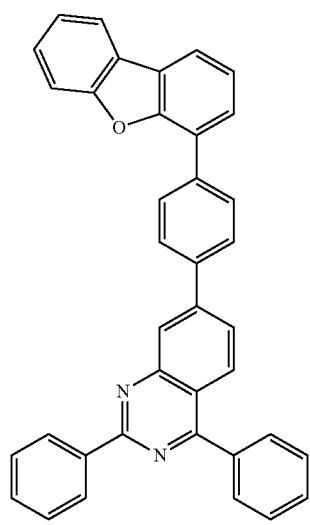
E-79
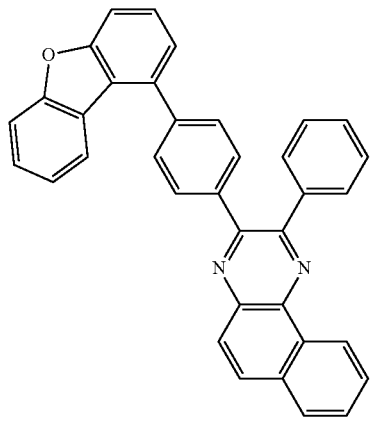
E-80
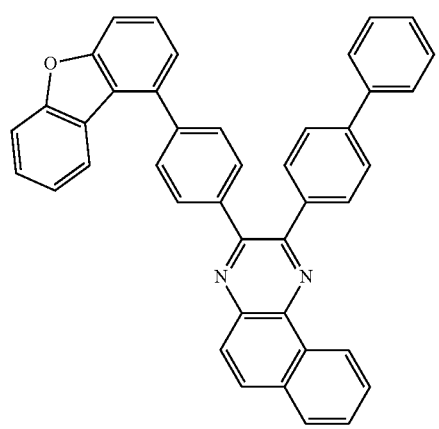
E-81
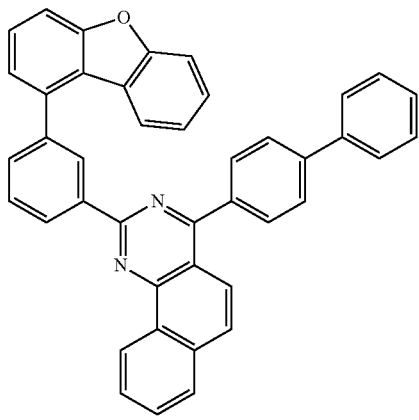

E-82
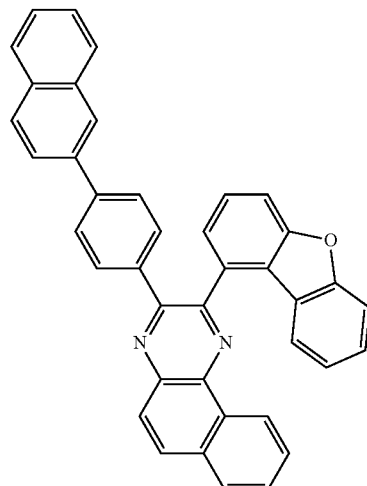
E-83
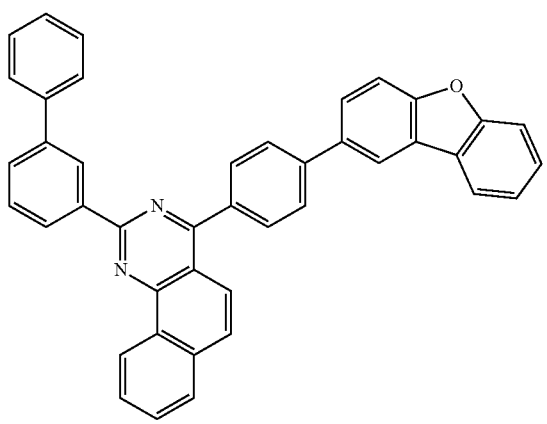
E-84
E-85
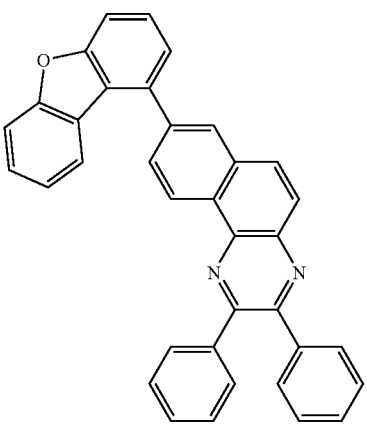
E-86
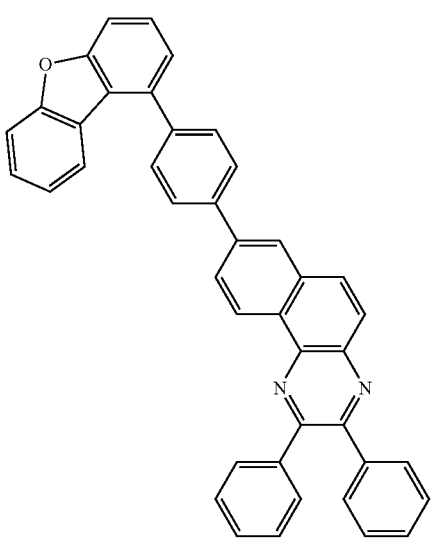
E-87
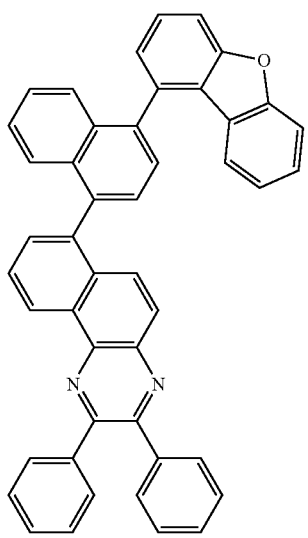

E-88
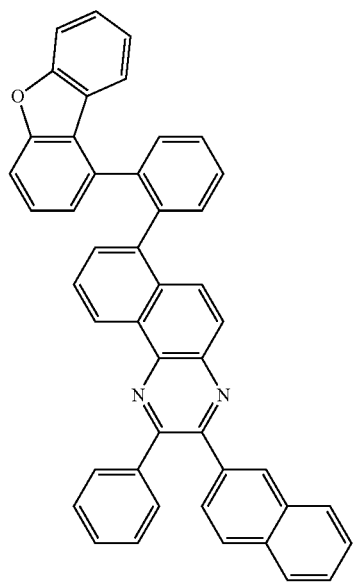
E-89
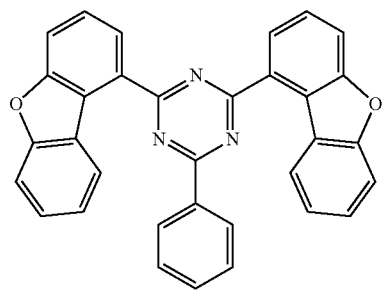
E-90
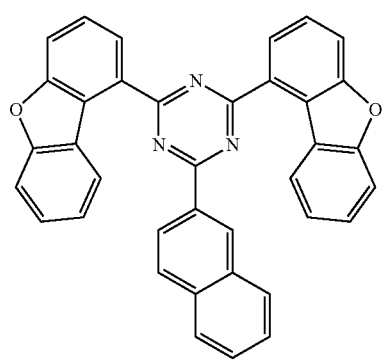
E-91
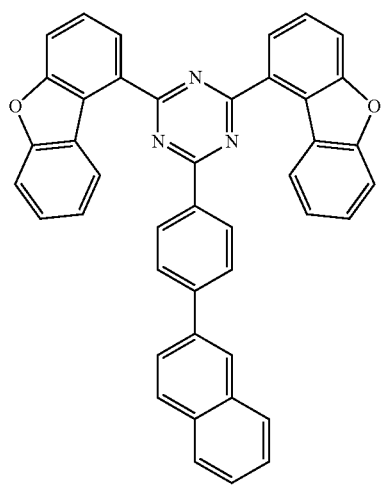
E-92
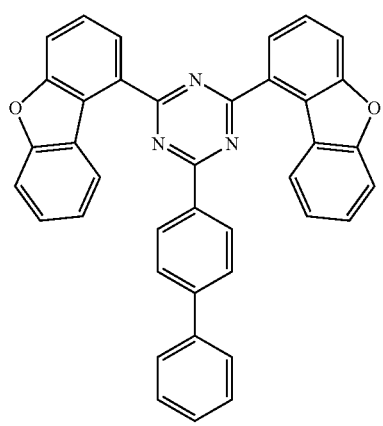
E-93
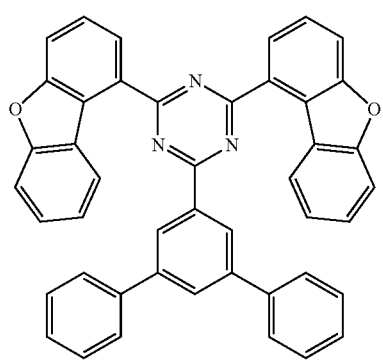

-continued
E-94
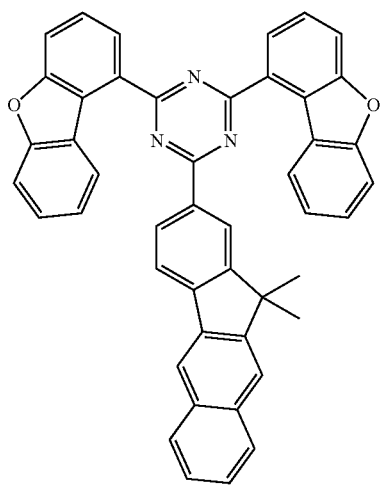
E-95
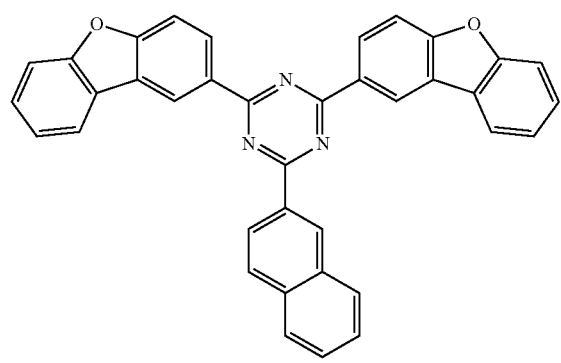
E-96
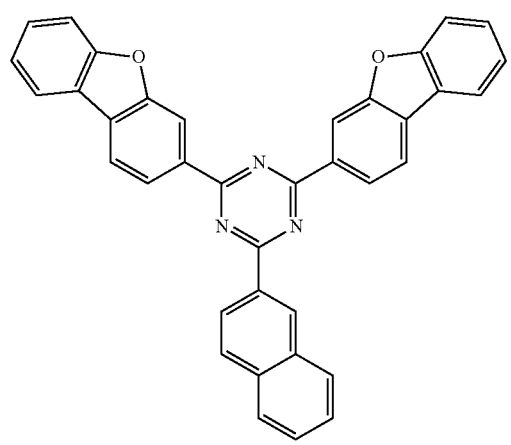
-continued
E-97
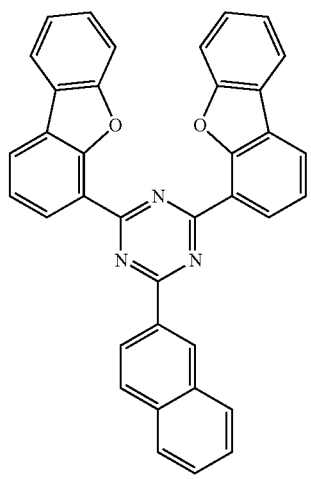
E-98
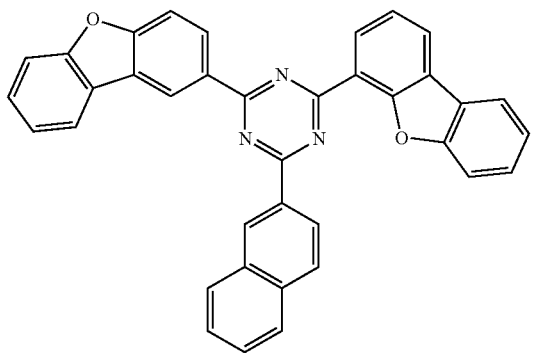
E-99
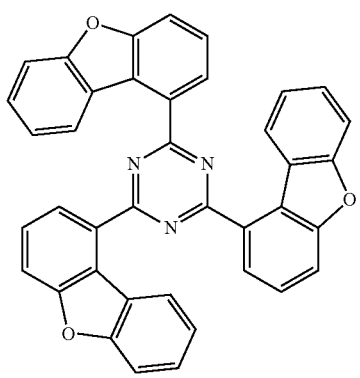
E-100
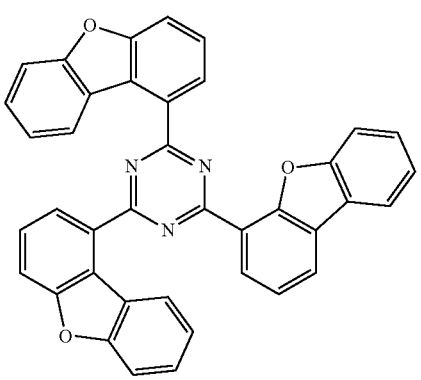

E-101
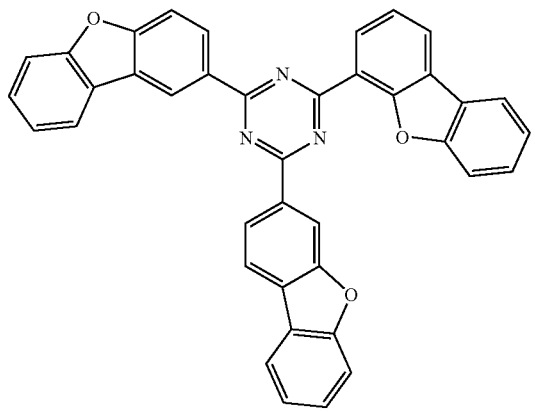
E-102
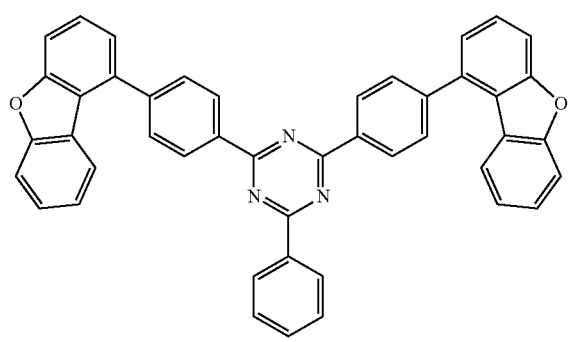
E-103
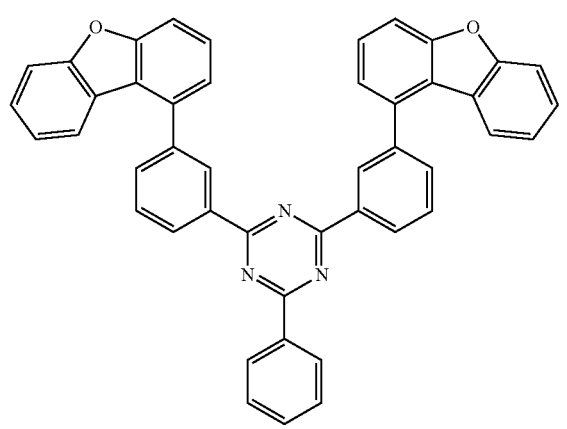
E-104
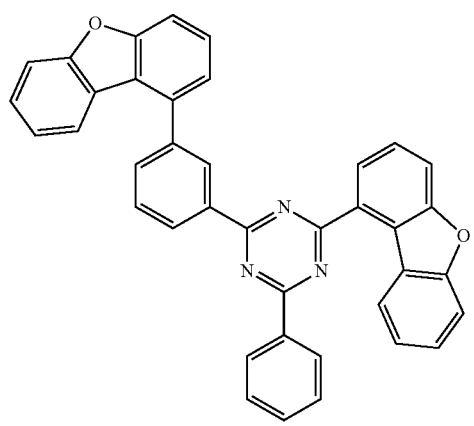
E-105
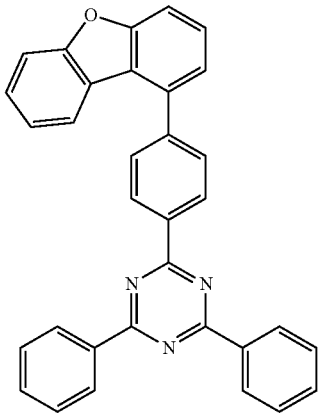
E-106
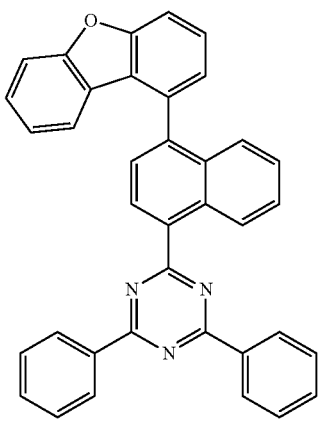
E-107
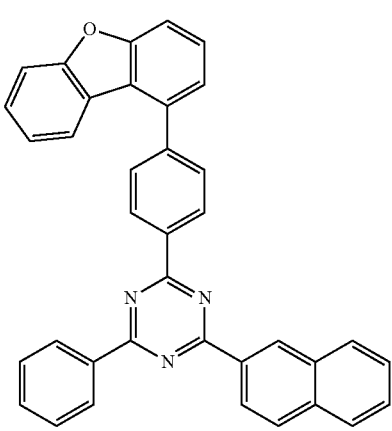

E-108
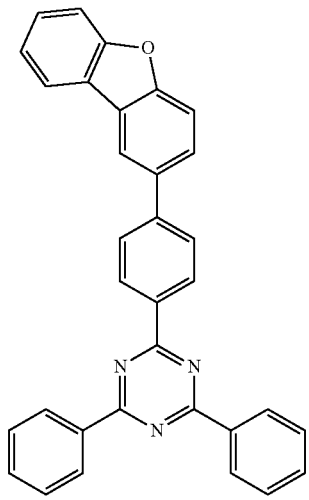
E-109
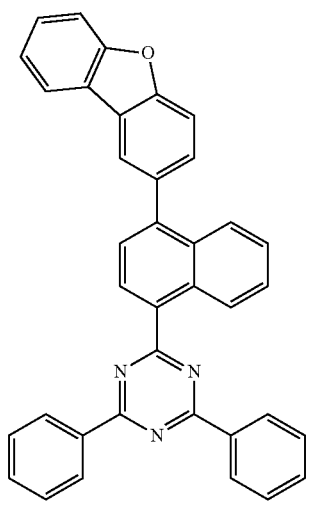
E-110
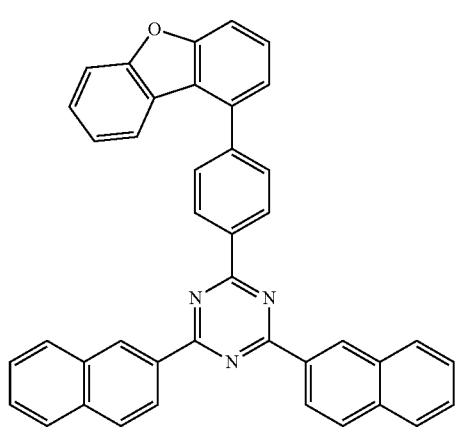
E-111
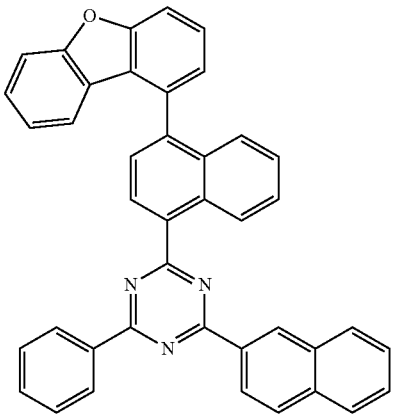
E-112
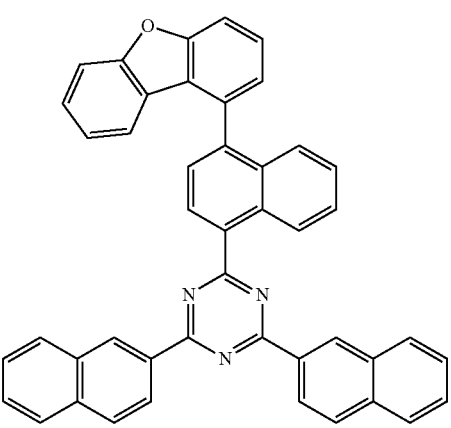
E-113
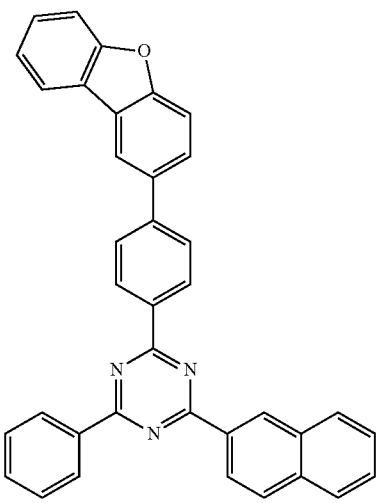

E-114
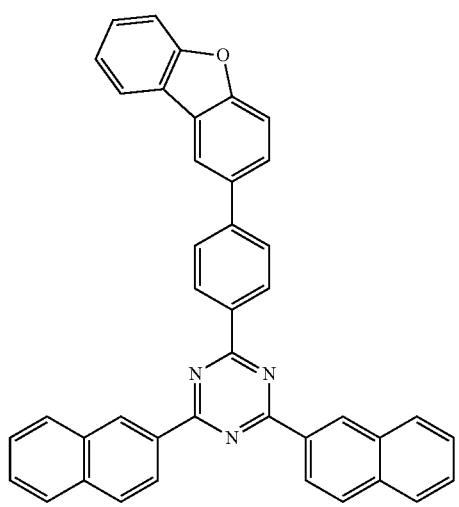
E-115
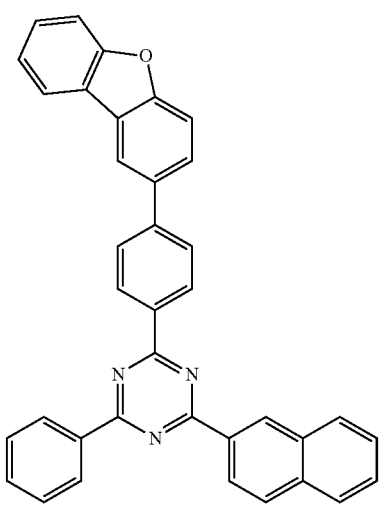
E-116
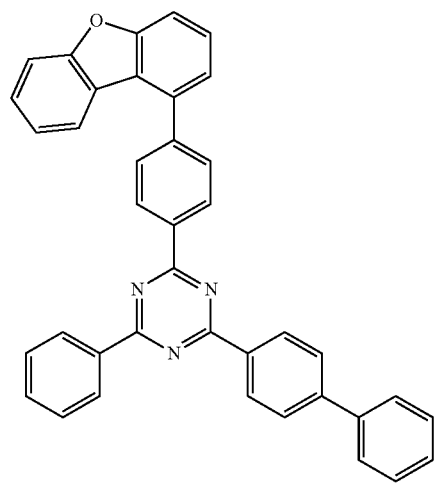
E-117
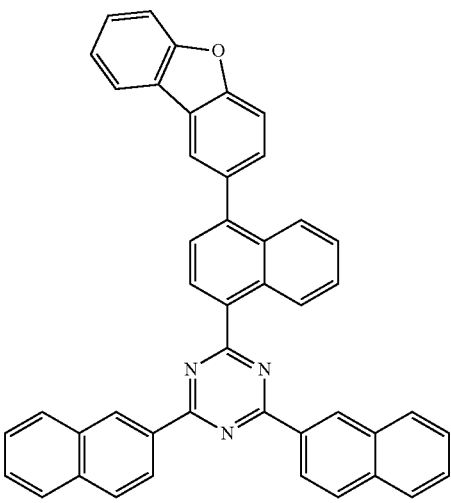
E-118
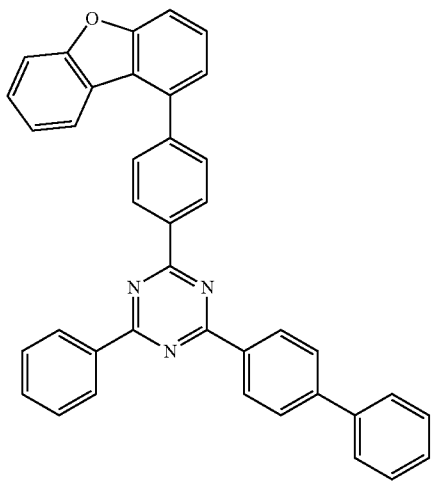
E-119

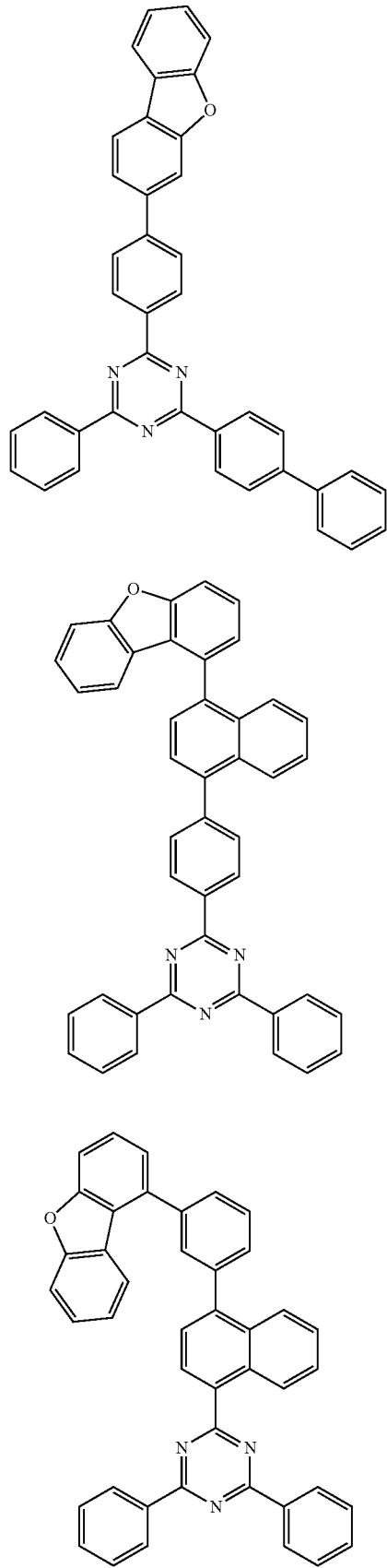

E-125
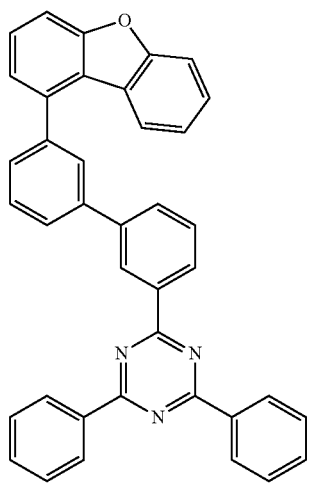
E-126
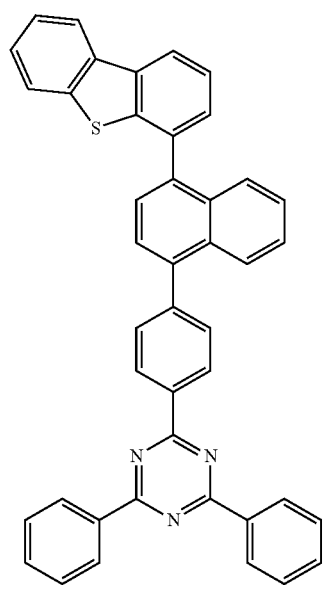
E-127
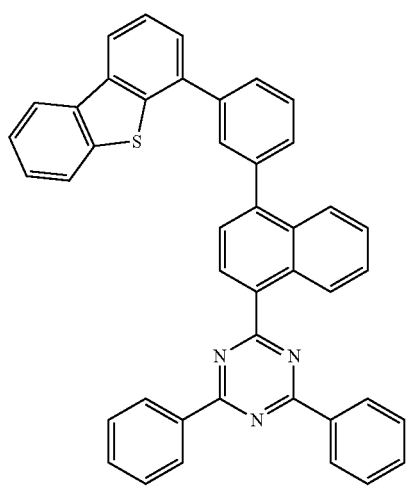
E-128
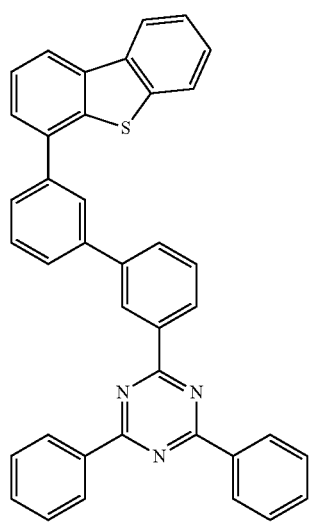
E-129
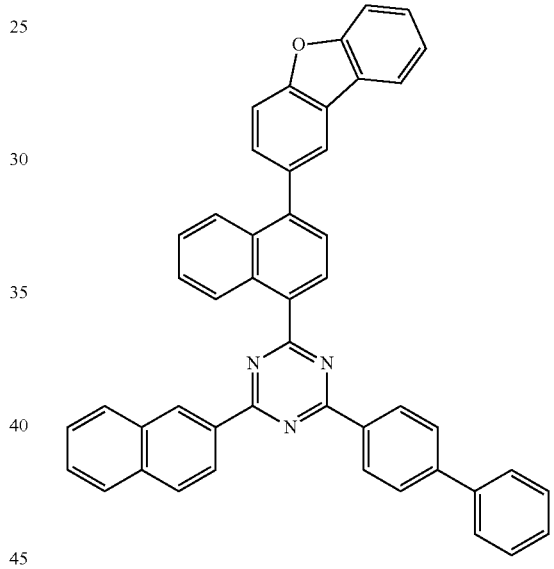
E-130
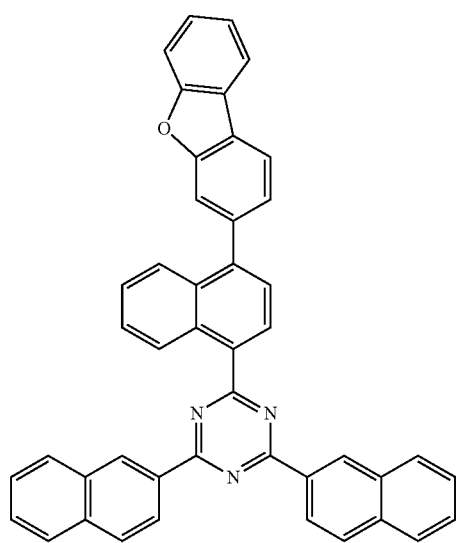

E-131
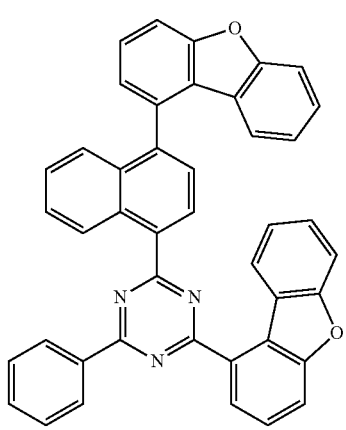
E-132
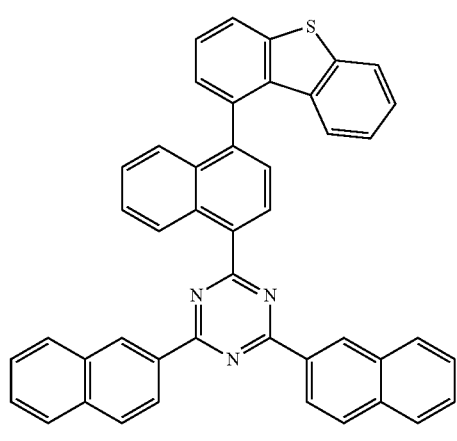
E-133
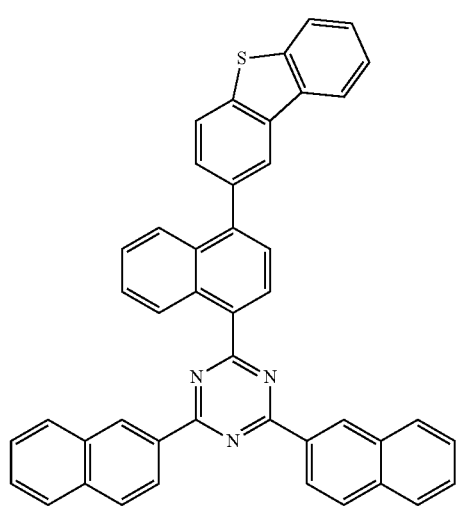
E-134
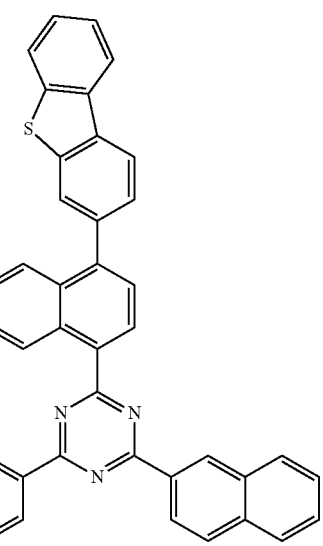
E-135
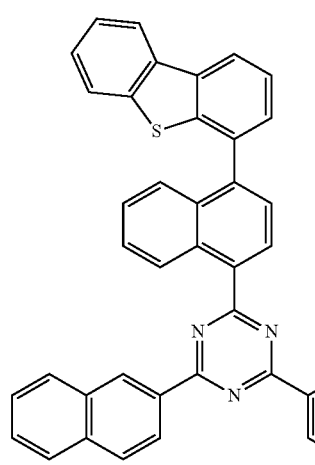
E-136
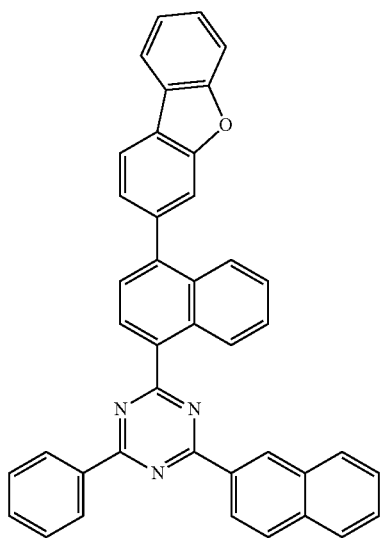

E-137
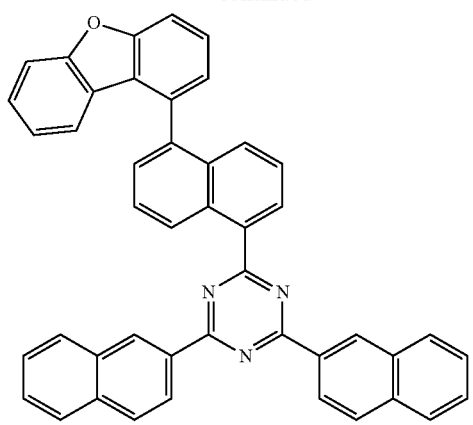
E-138
E-139
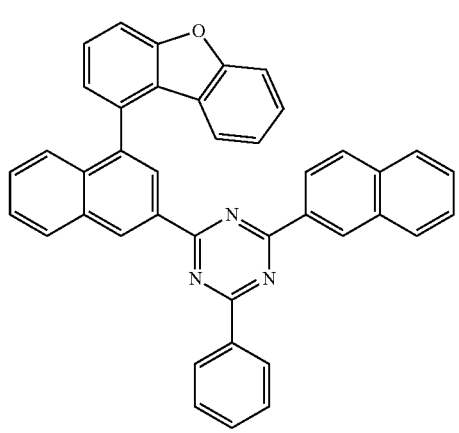
E-140
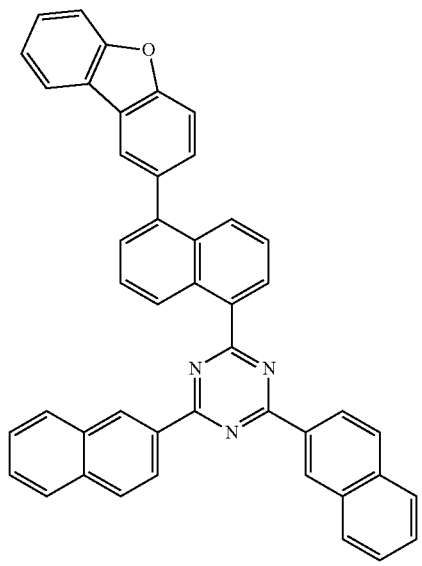
E-141
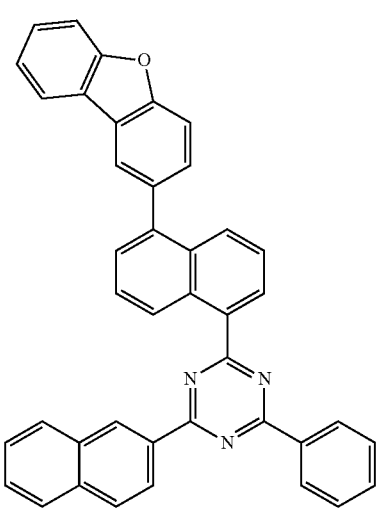
E-142
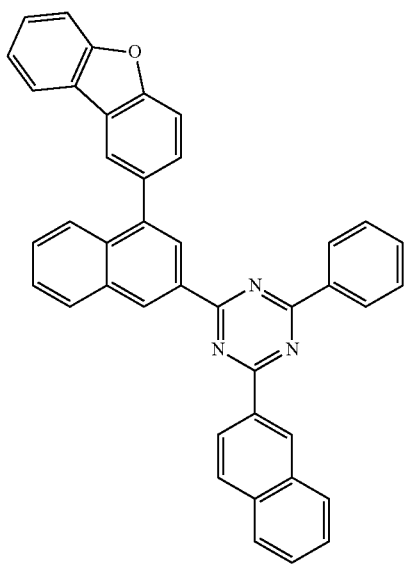

E-143
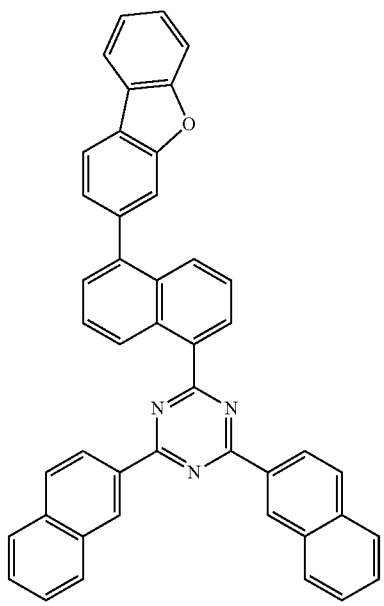
E-144
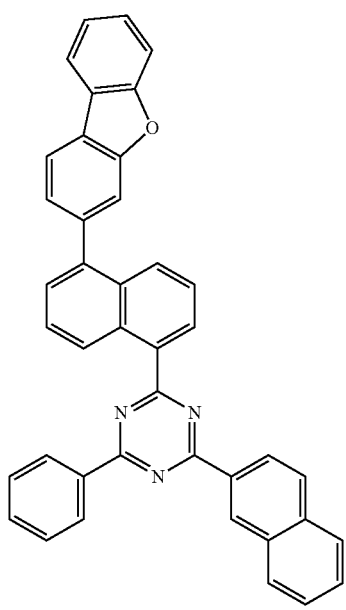
E-145
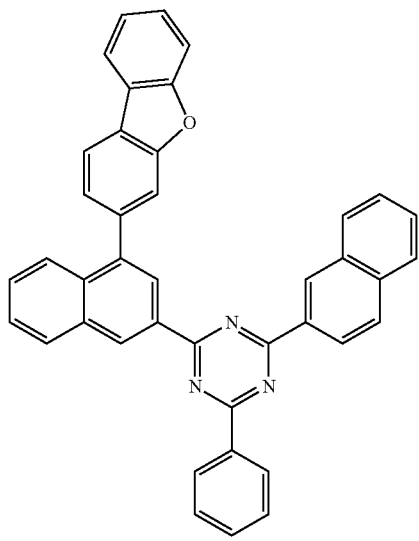
The compound represented by formula 2 includes the following compounds, but is not limited thereto.
H-1
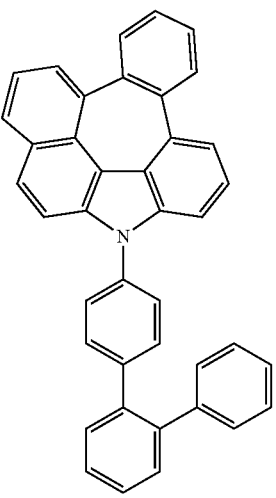
H-2
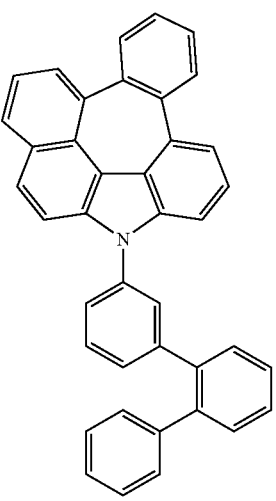

H-3
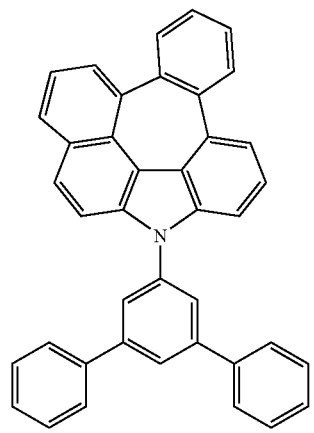
H-4
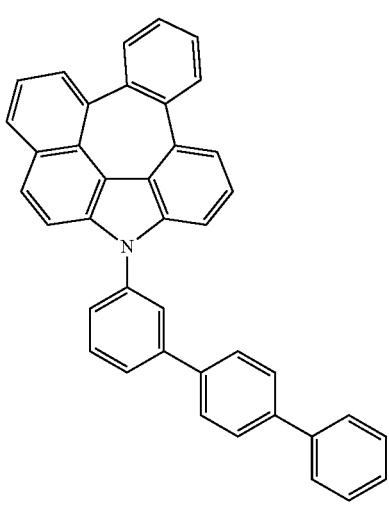
H-5
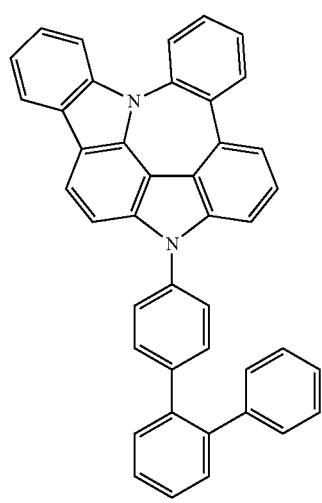
H-6
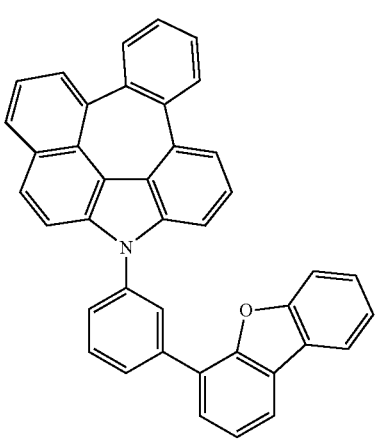
H-7
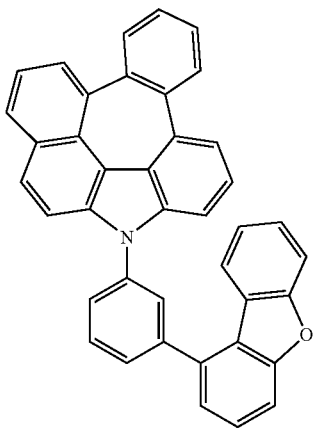
H-8
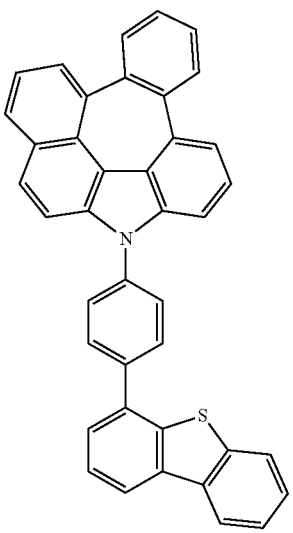

-continued
H-9
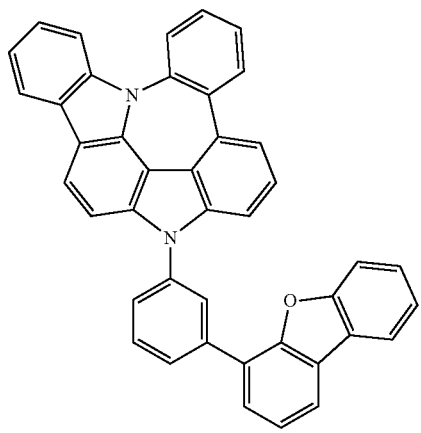
H-10
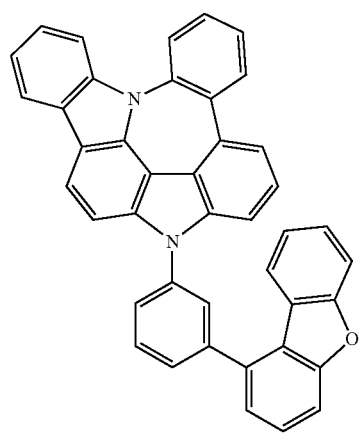
H-11
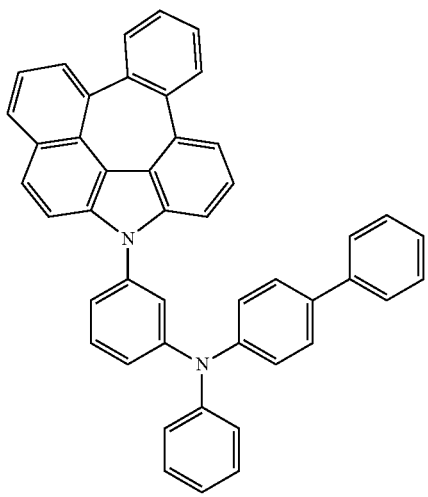
-continued
H-12
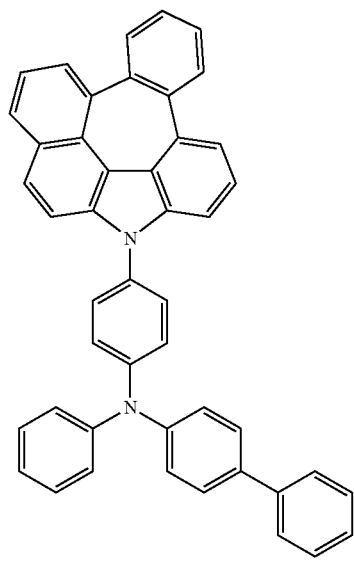
H-13
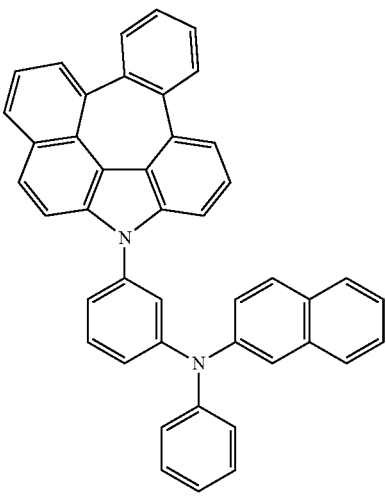
H-14
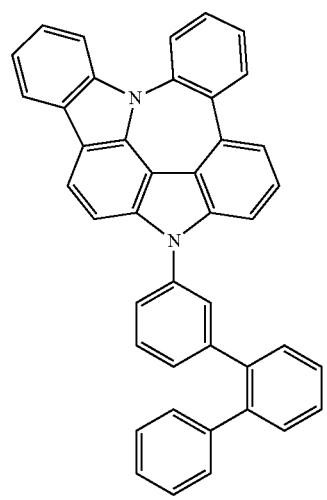

H-15
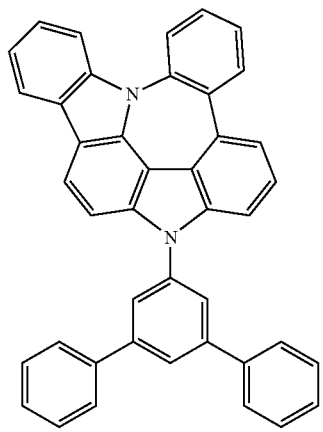
H-16
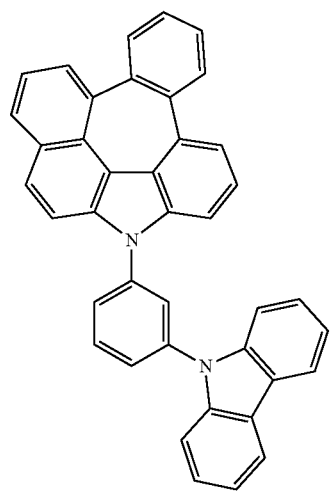
H-17
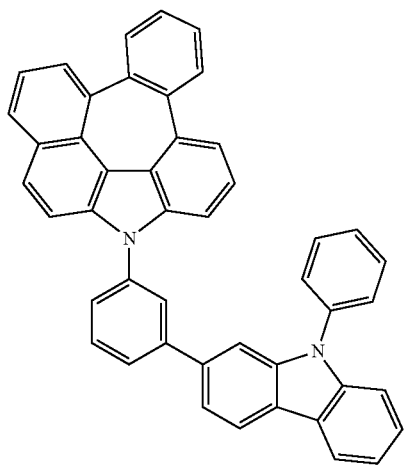
H-18
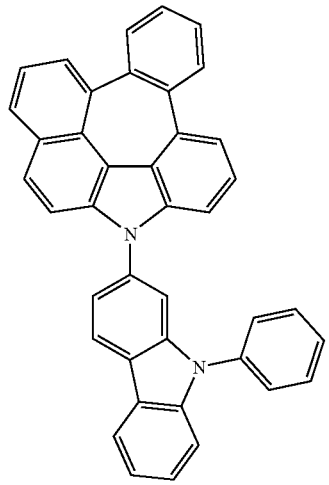
H-19
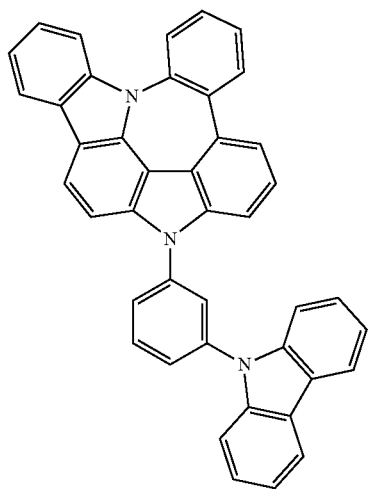
H-20
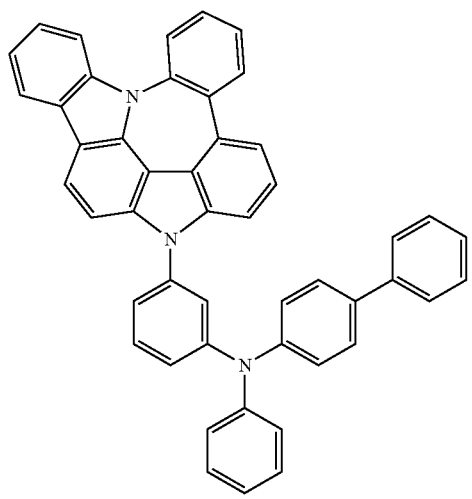

-continued
H-21
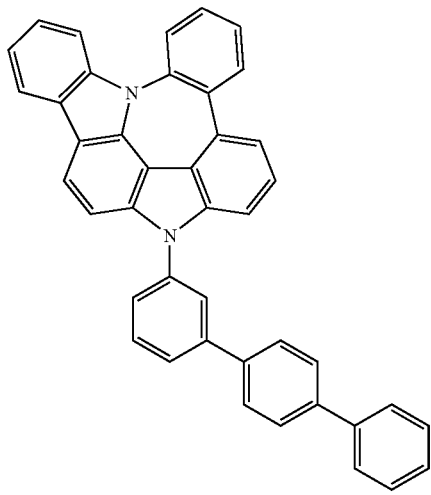
H-22
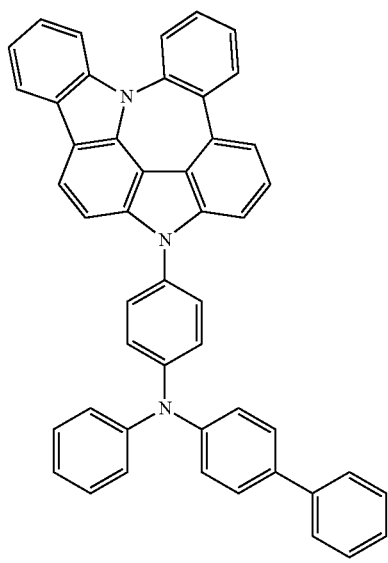
H-23
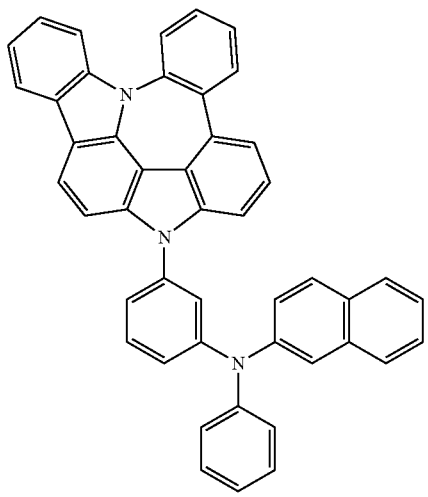
-continued
H-24
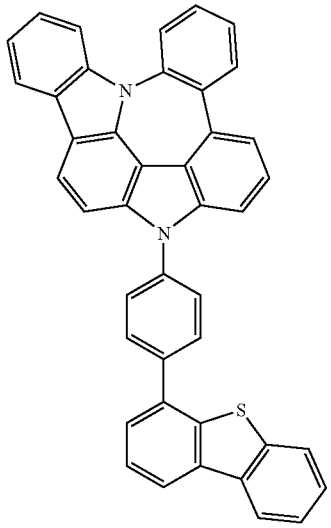
H-25
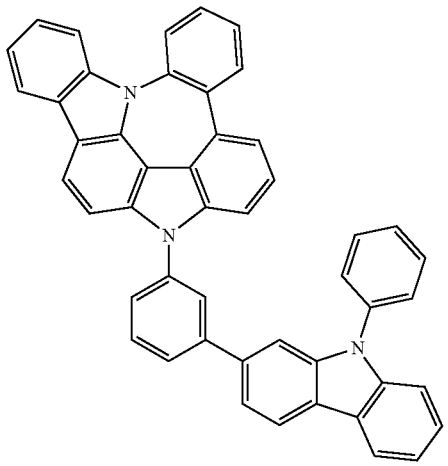
H-26
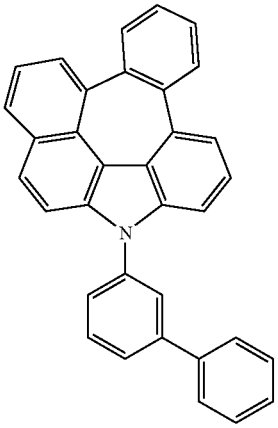

H-27
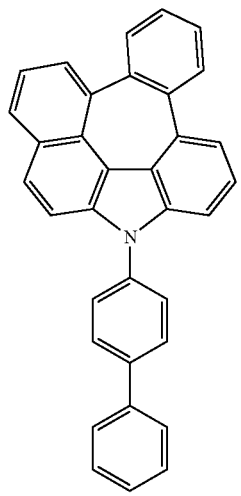
H-28
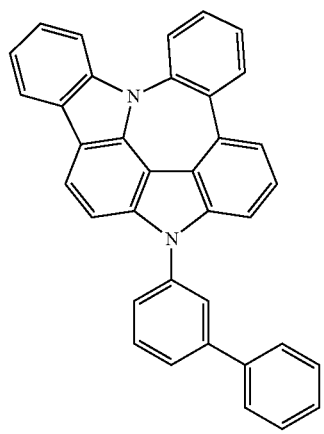
H-29
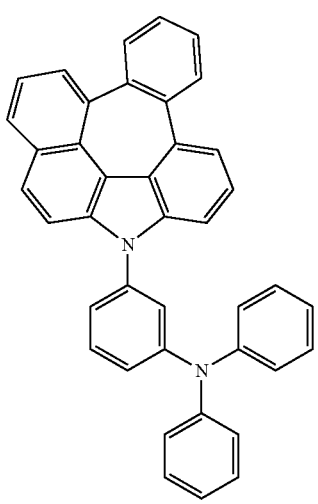
H-30
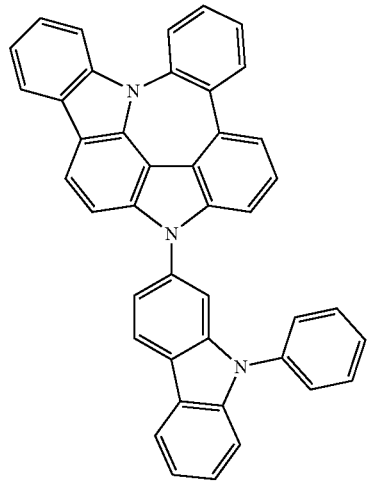
H-31
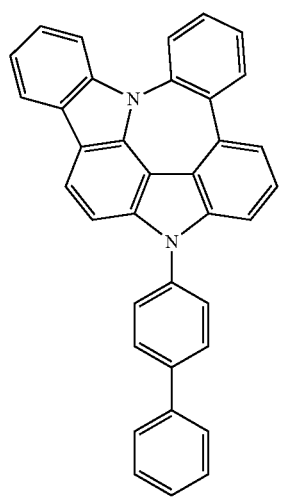
H-32
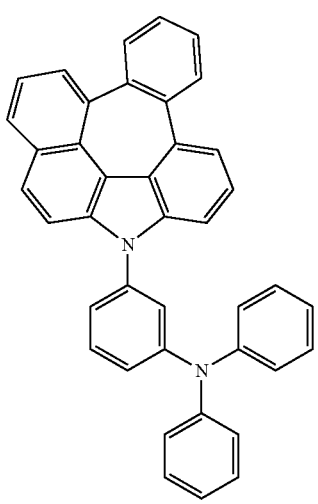

H-33
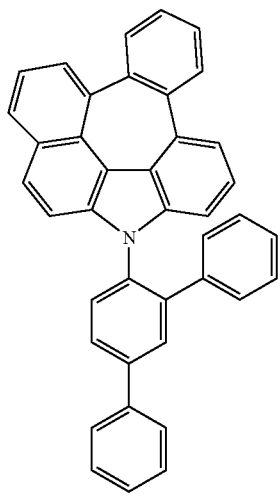
H-36
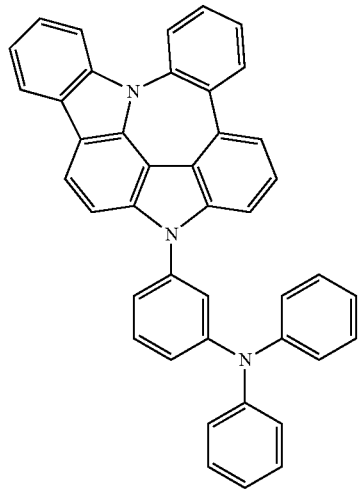
H-34
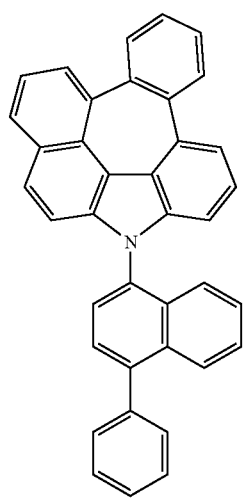
H-37
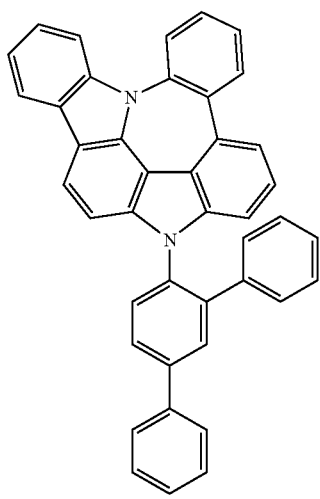
H-35
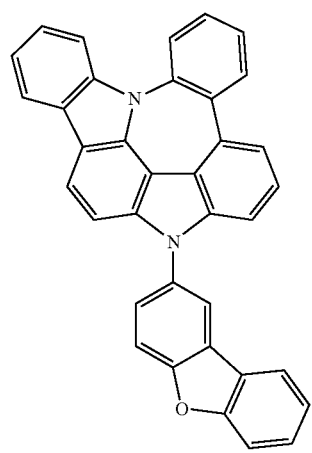
H-38
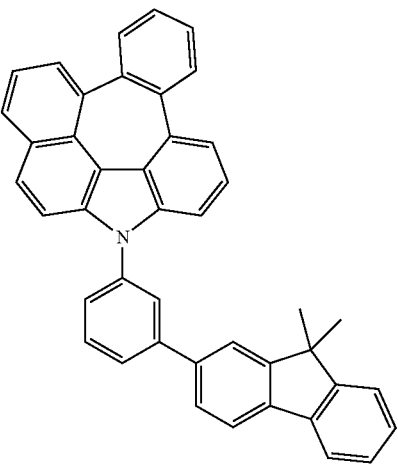

H-39
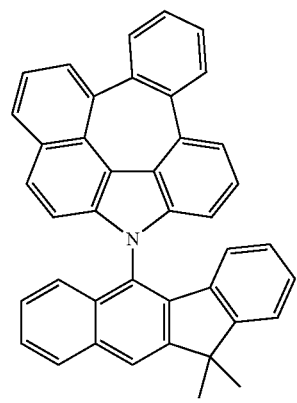
H-40
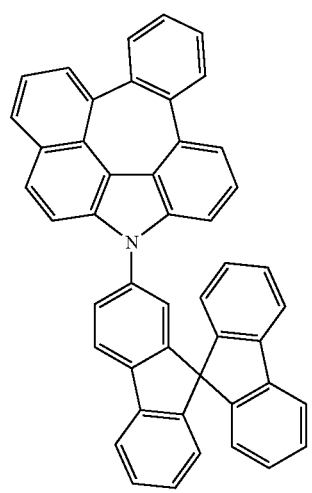
H-41
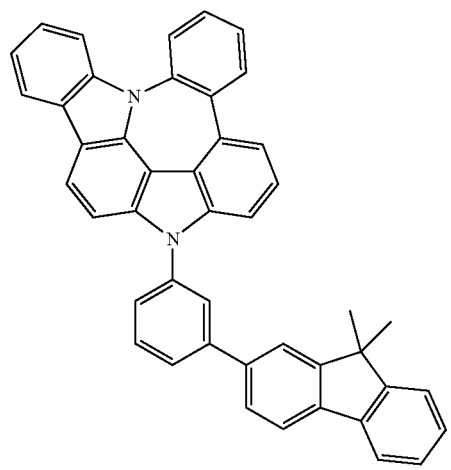
H-42
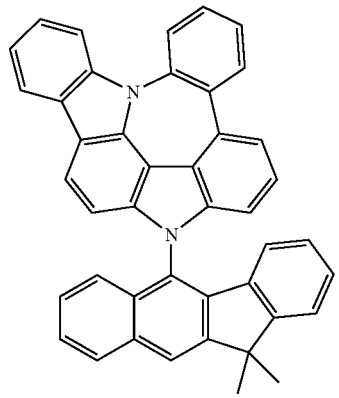
H-43
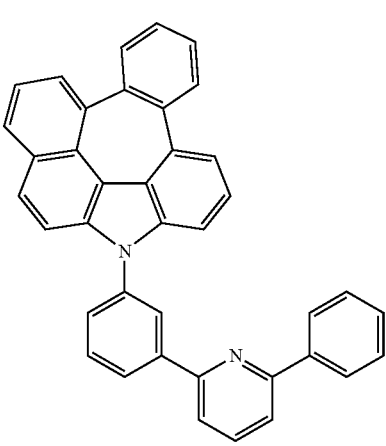
H-44
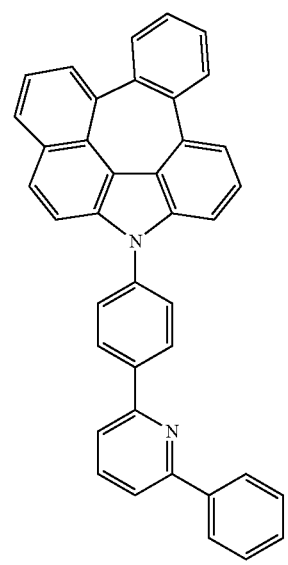

H-45
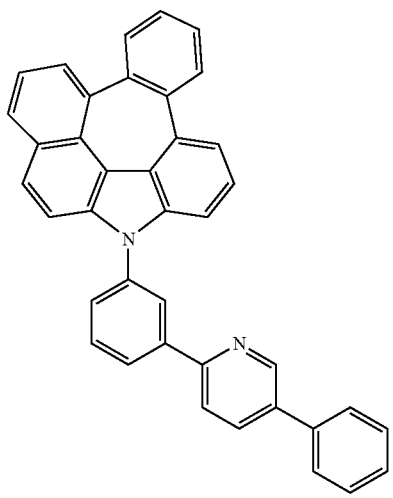
H-46
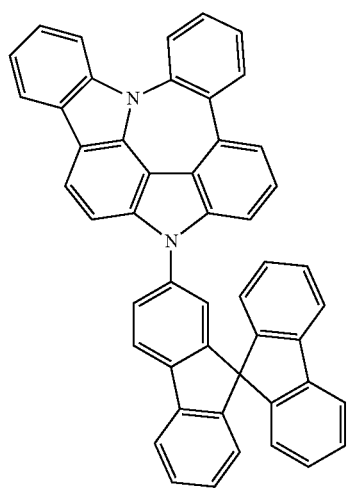
H-47
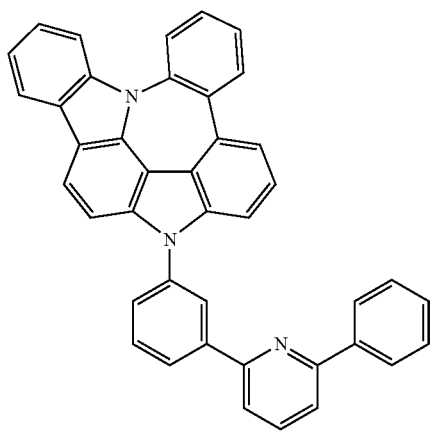
H-48
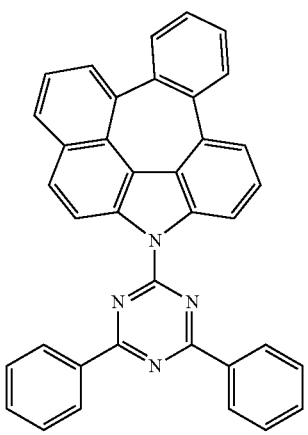
H-49
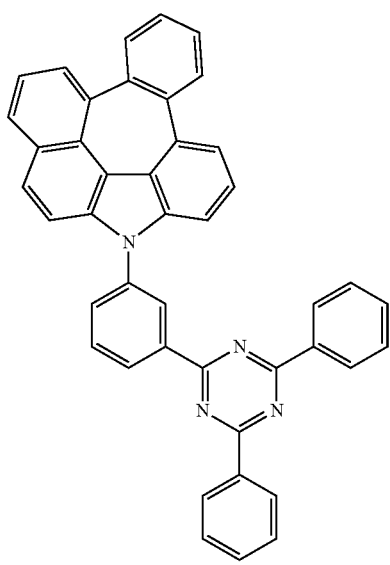
H-50
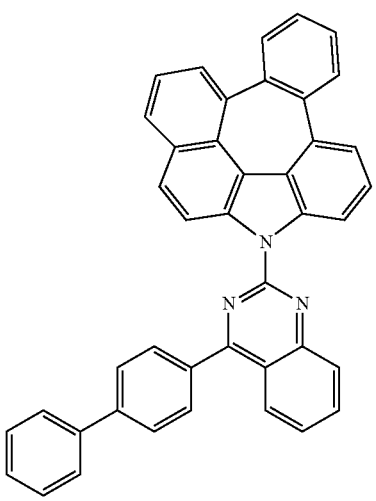

H-51
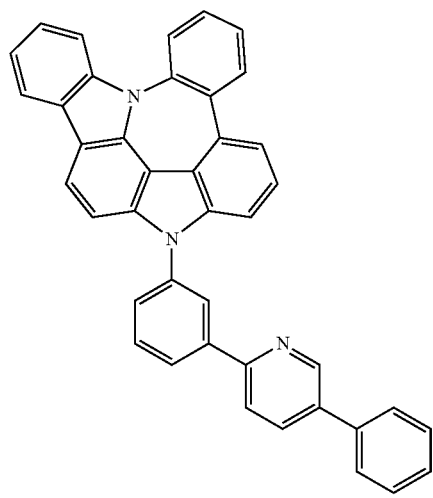
H-52
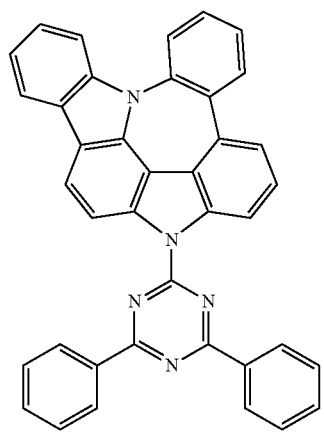
H-53
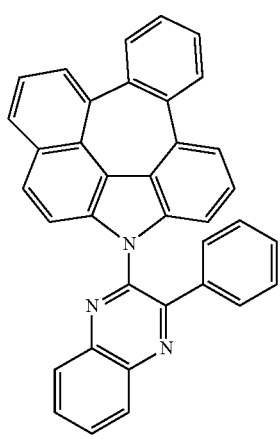
H-54
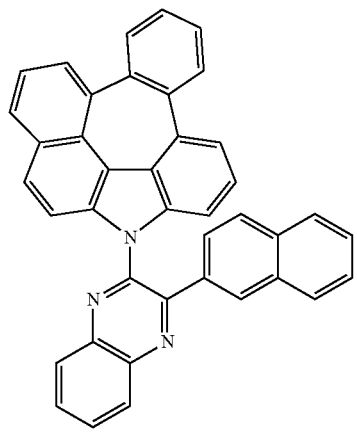
H-55
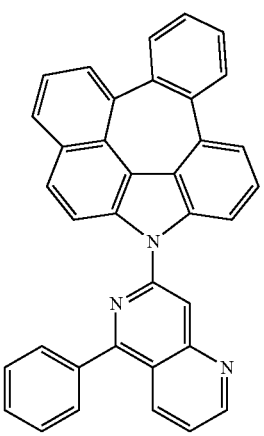
H-56
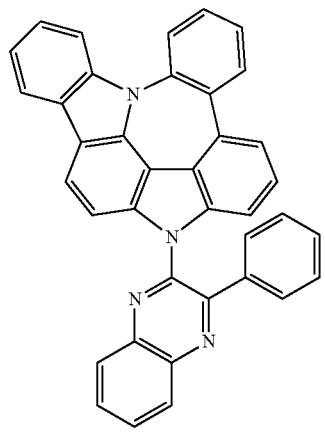

-continued
H-57
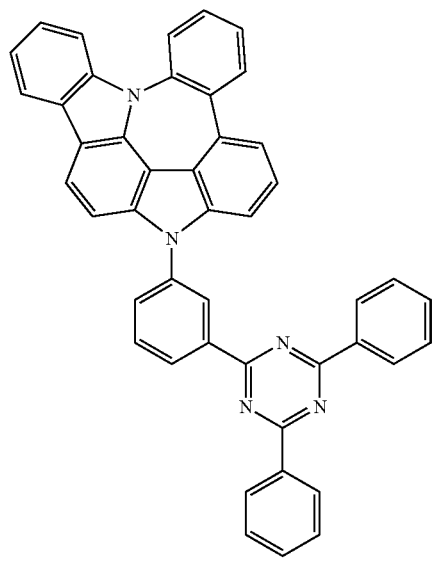
H-58
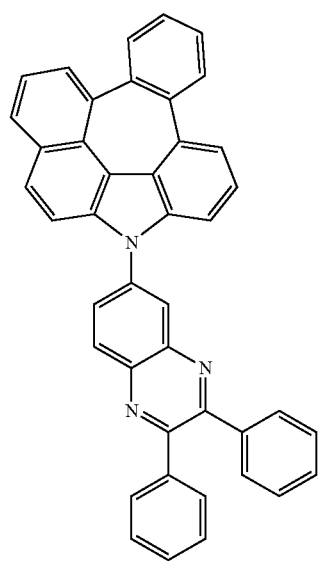
H-59
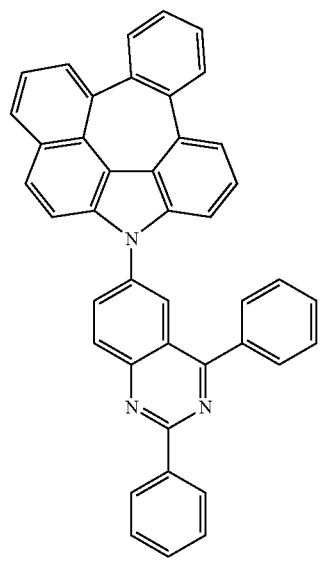
-continued
H-60
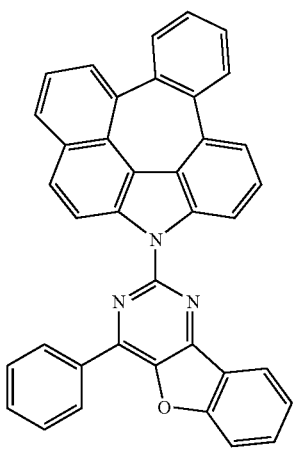
H-61
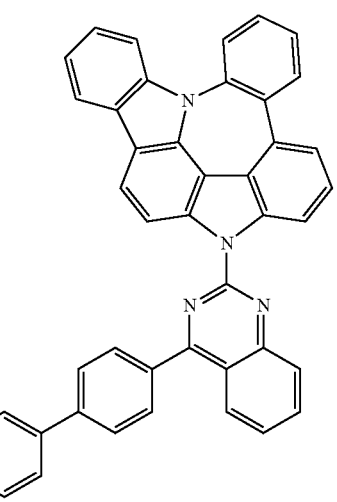
H-62
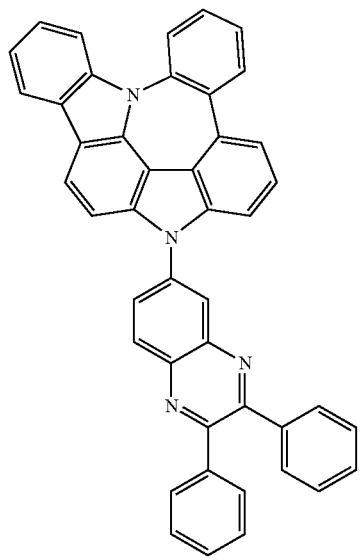

H-63
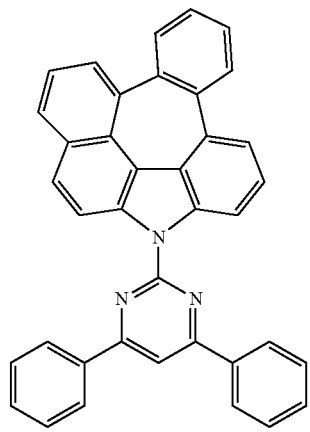
H-64
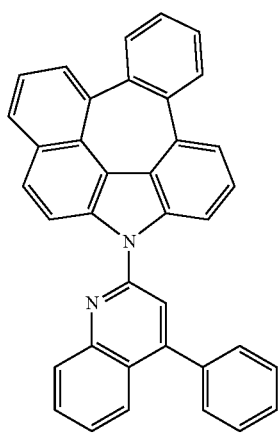
H-65
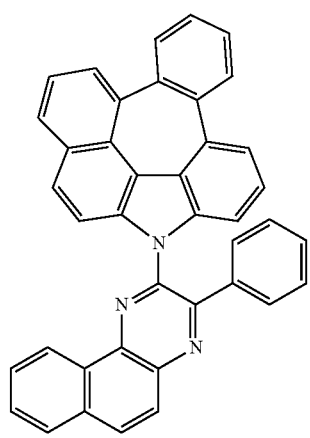
H-66
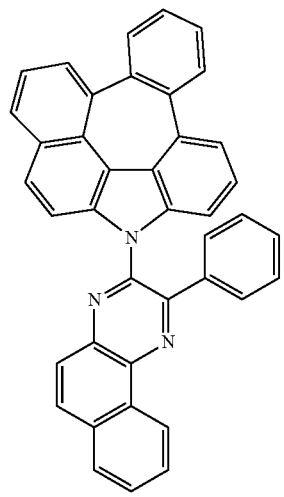
H-67
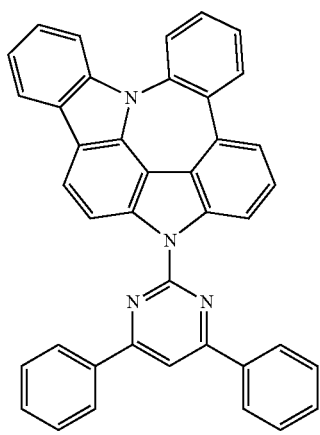
H-68
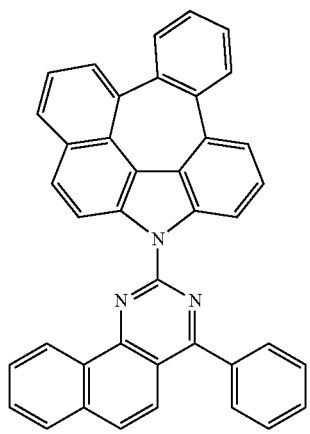

H-69
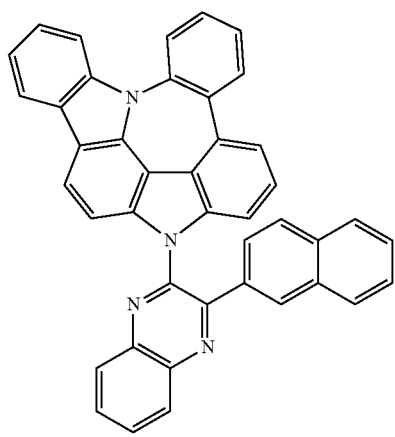
H-70
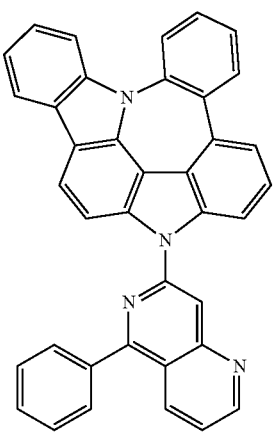
H-71
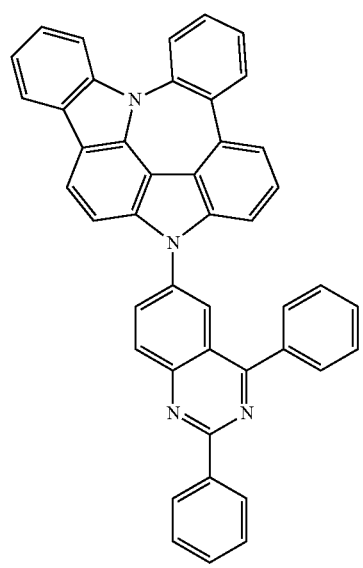
H-72
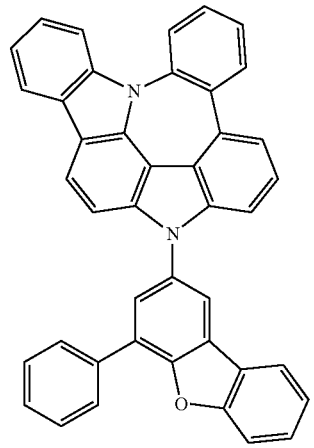
H-73
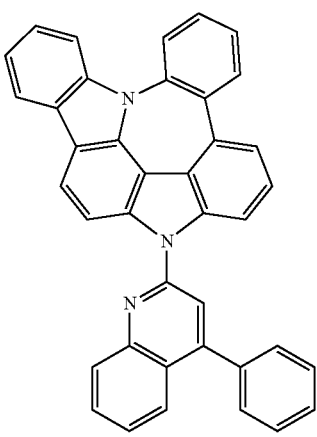
H-74
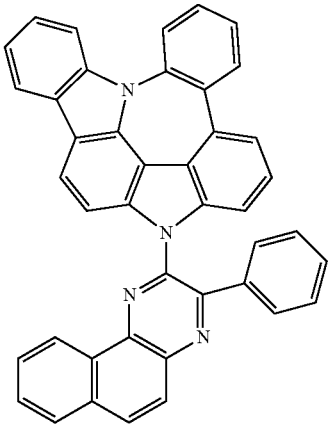

H-75
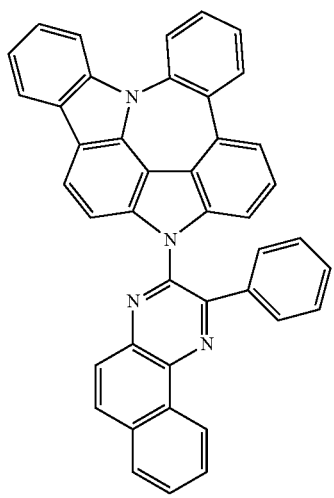
H-76
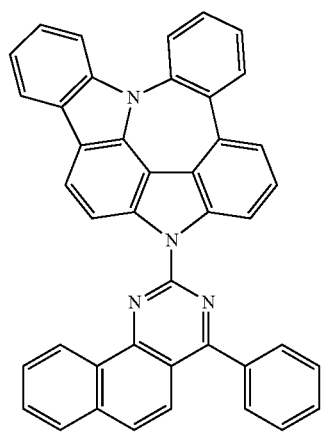
H-77
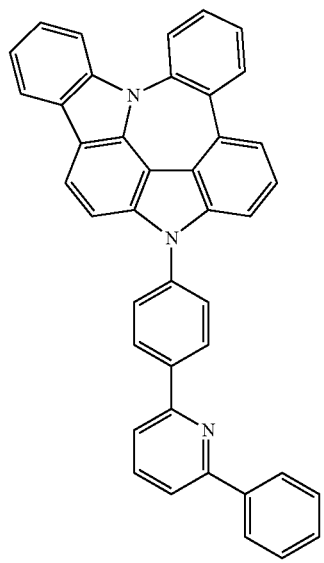
H-78
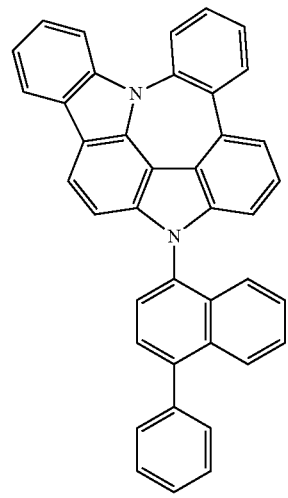
H-79
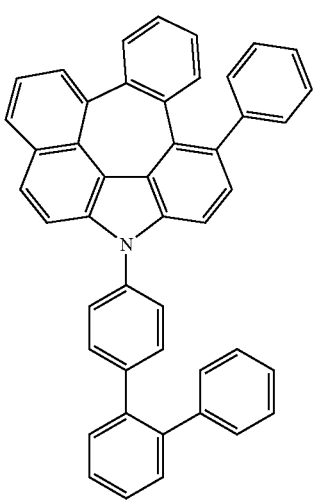
H-80
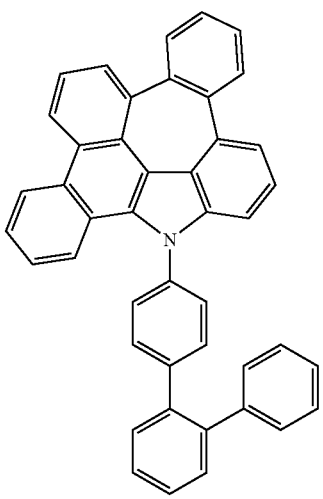

-continued
H-81
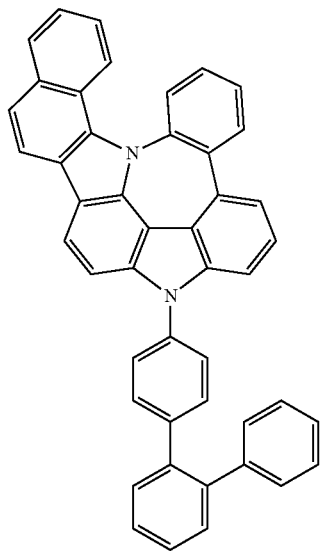
H-82
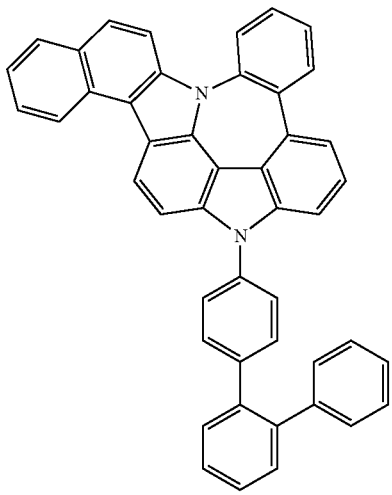
H-83
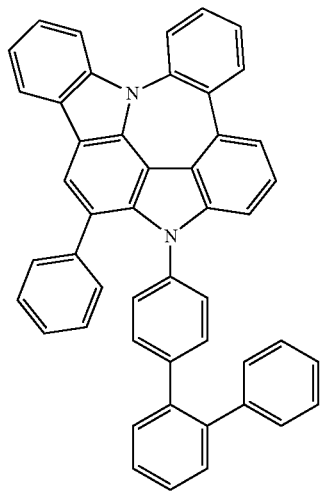
-continued
H-84
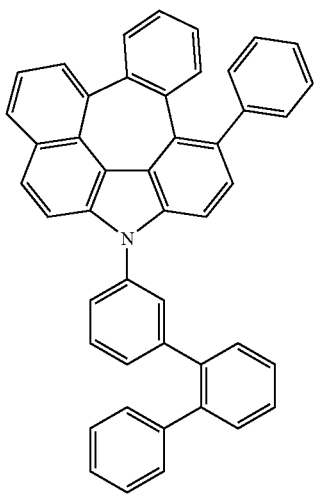
H-85
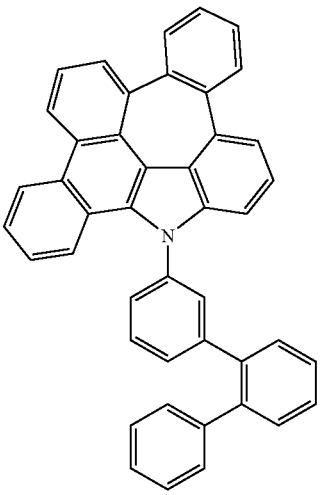
H-86
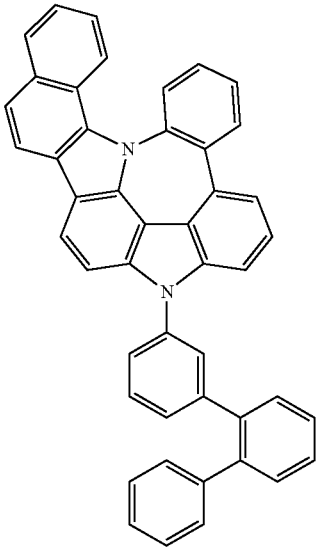

-continued
H-87
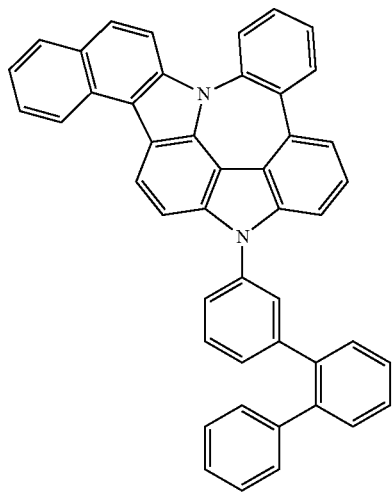
H-88
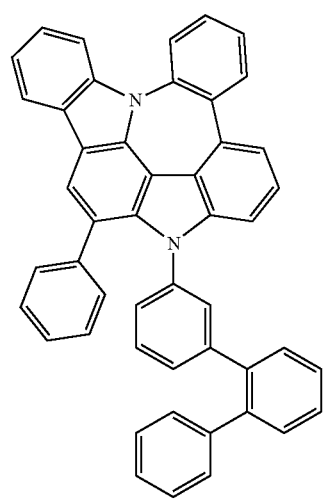
H-89
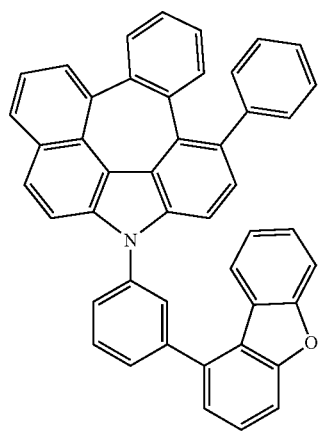
-continued
H-90
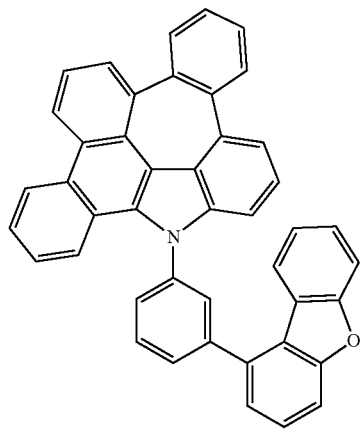
H-91
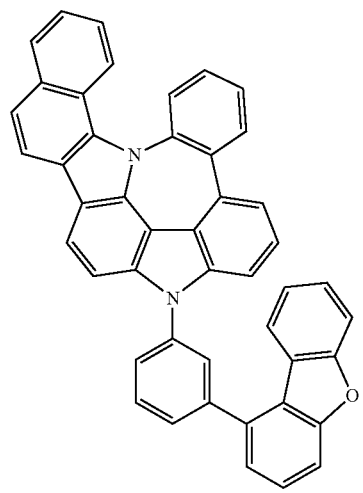
H-92
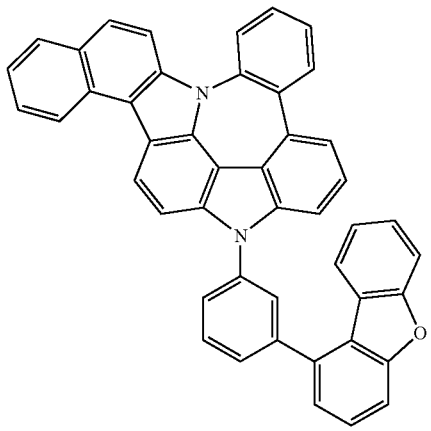

-continued
H-93
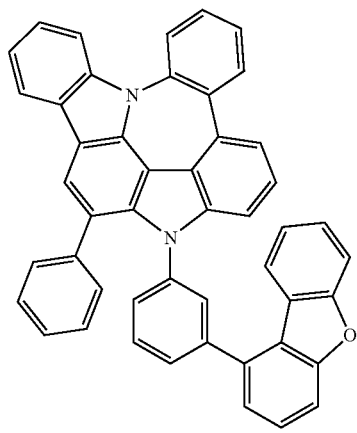
H-94
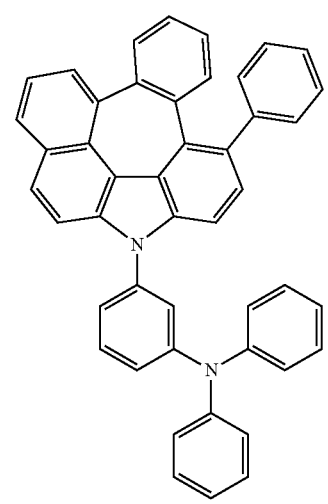
H-95
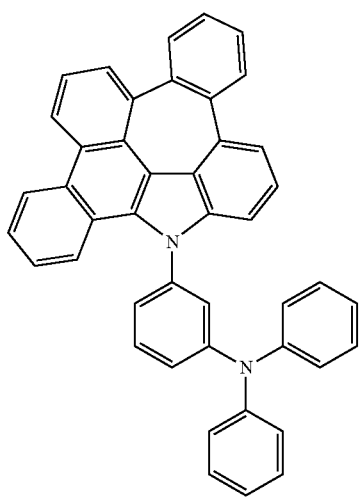
-continued
H-96
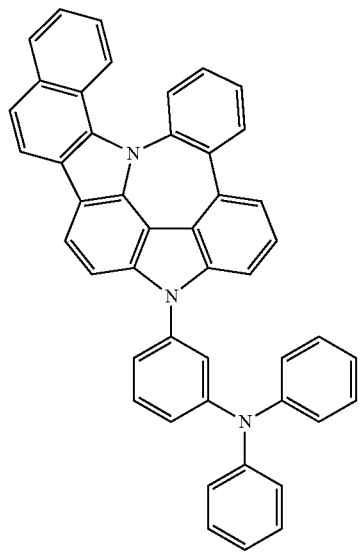
H-97
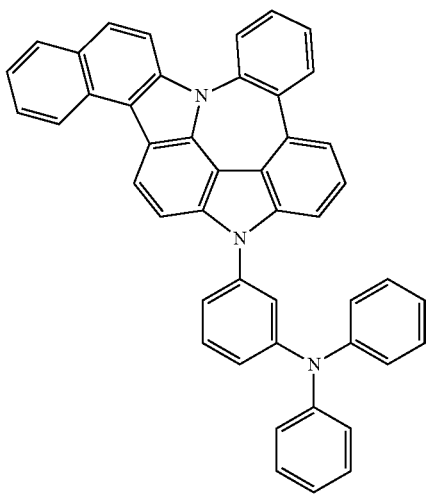
H-98
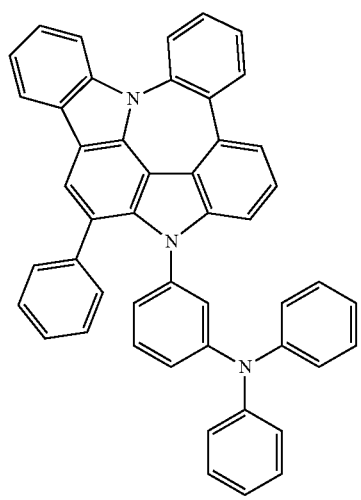

H-99
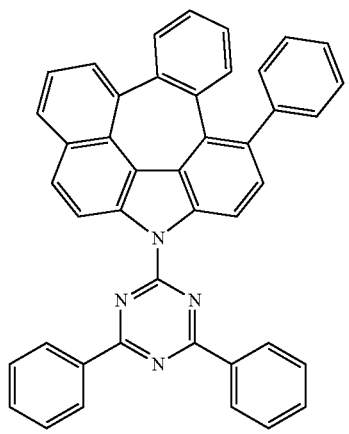
H-100
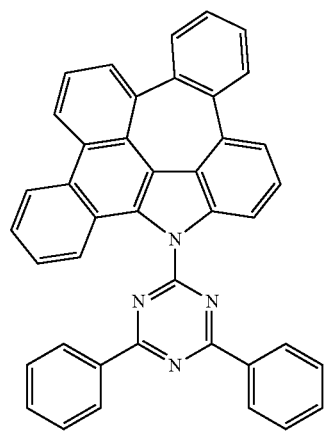
H-101
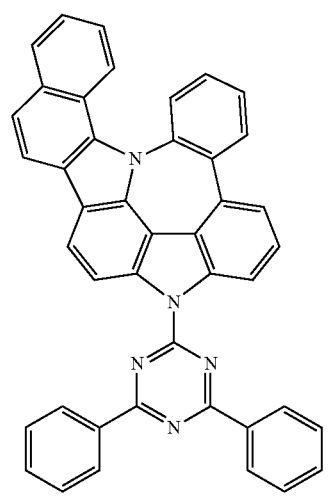
H-102
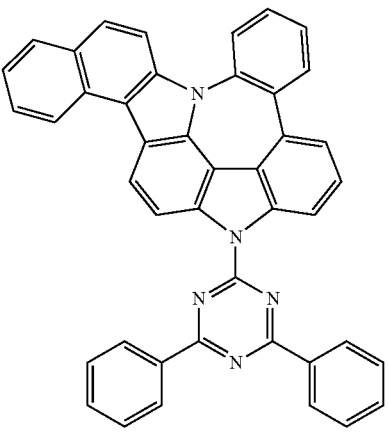
H-103
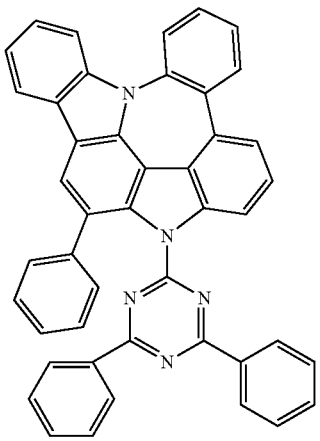
H-104
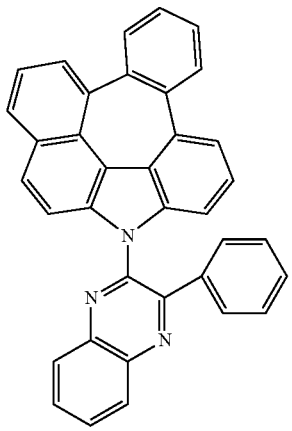

H-105
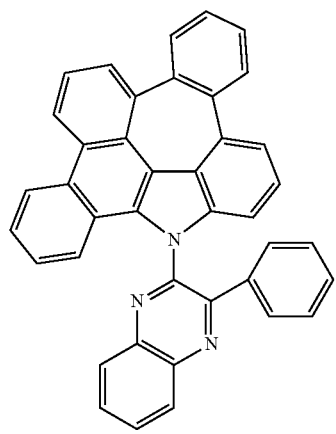
H-106
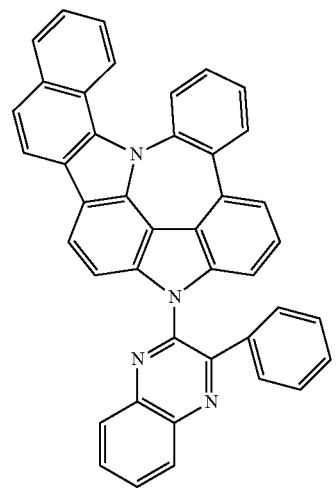
H-107
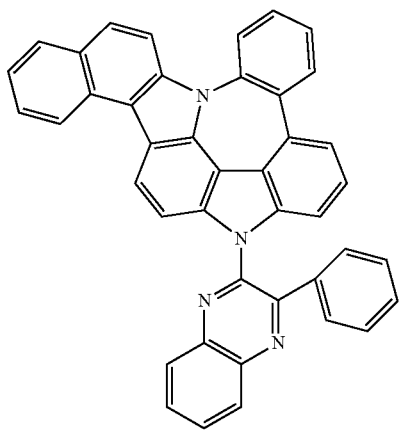
H-108
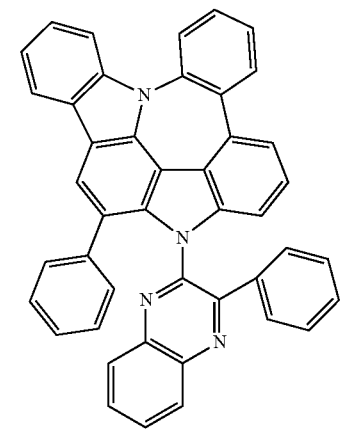
H-109
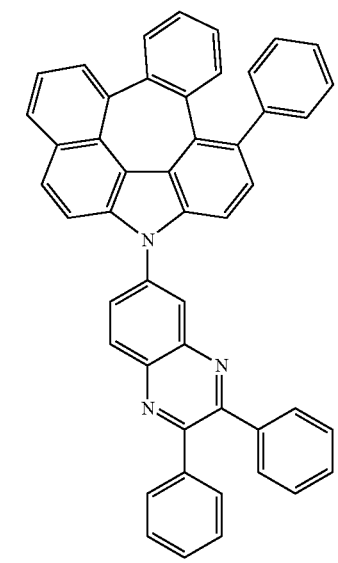
H-110
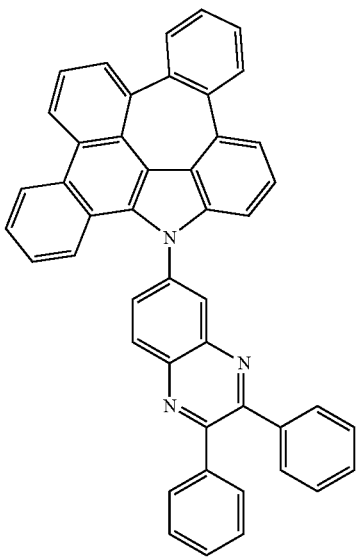

H-111
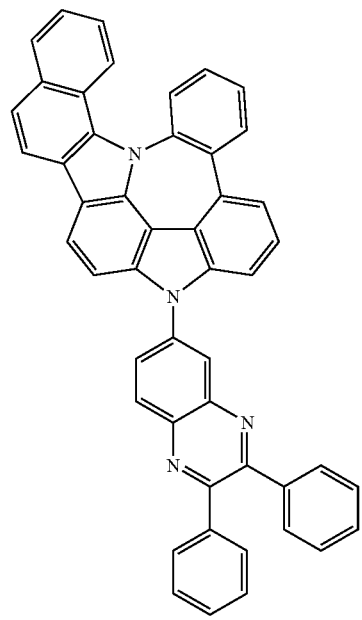
H-112
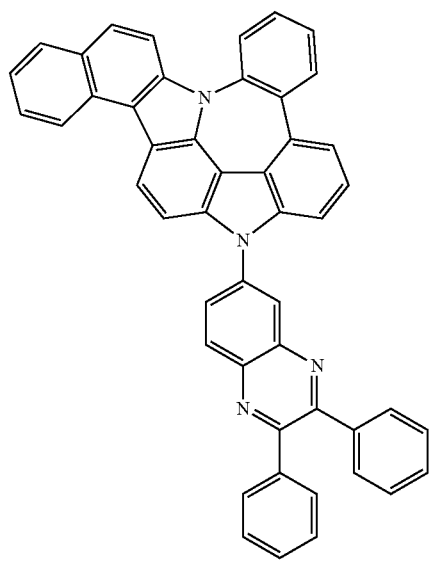
H-113
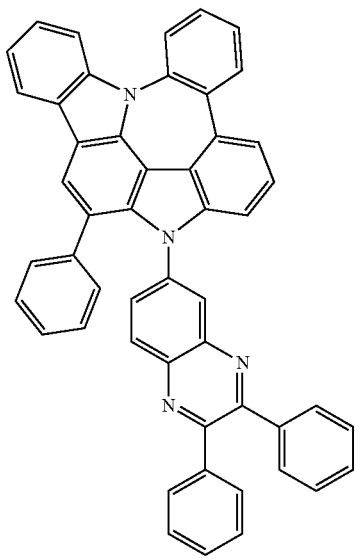
H-114
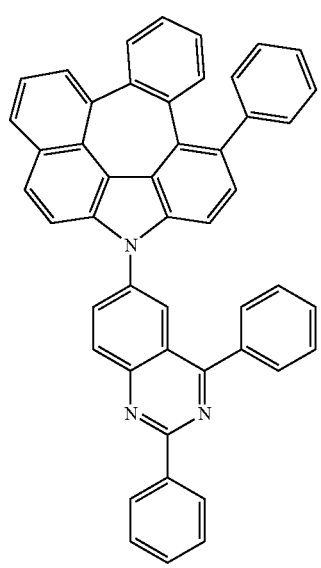
H-115

H-116
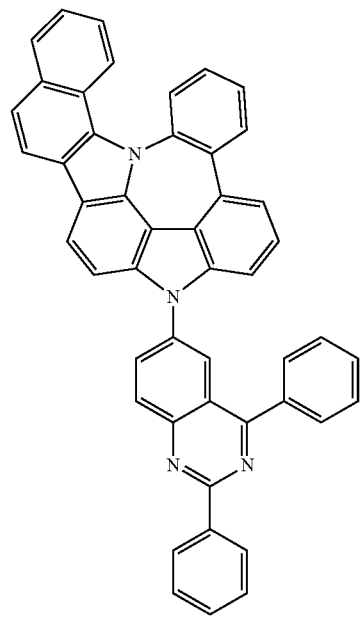
H-118
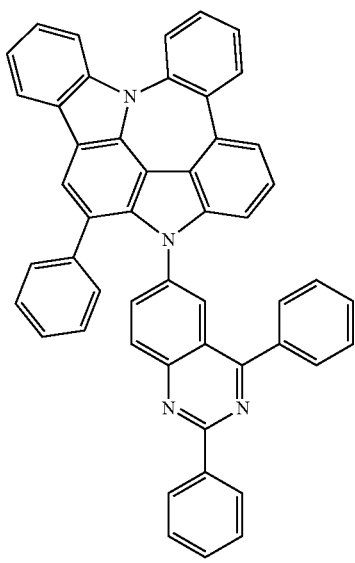
H-119
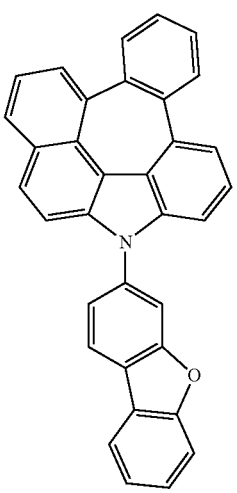
H-117
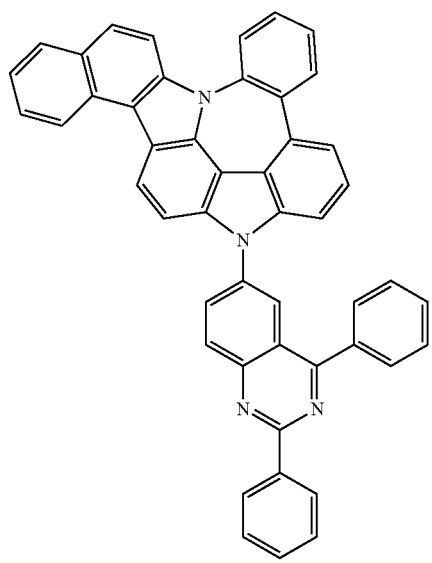
H-120
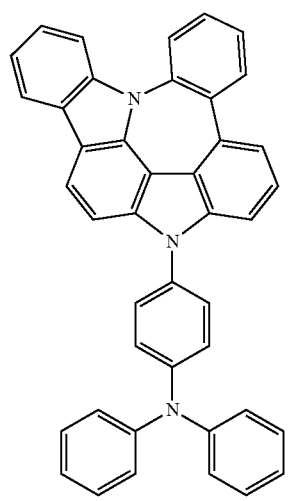

H-121

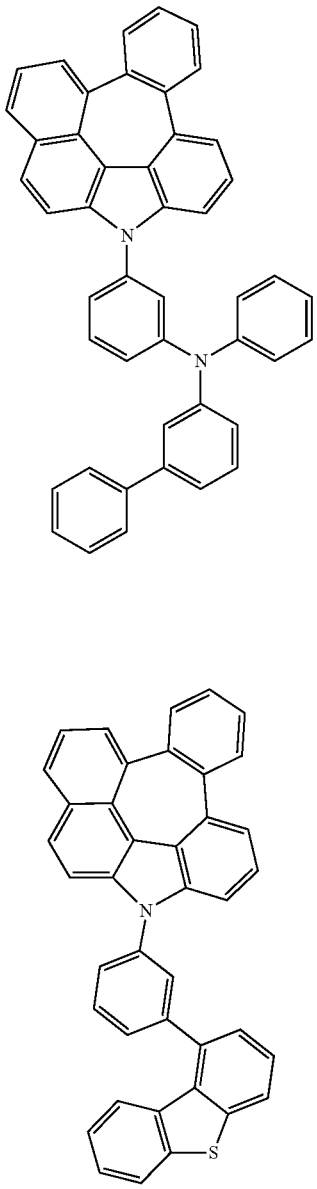

H-122

One or more of compounds E-1 to E-135 and one or more of compounds H-1 to H-122 may be combined and used in an organic electroluminescent device.

The compound represented by formula 1 according to the present disclosure may be prepared by a synthetic method known to one skilled in the art. For example, it may be prepared by referring to Korean Patent Application Laying-Open Nos. 2012-0033017, 2013-0128322, 2016-0038006, 2015-0122343, and 2016-0049083; U.S. Patent Application Publication No. 2016/0233436; International Publication No. WO 2017/178311, etc., but is not limited thereto.

The compound represented by formula 2 according to the present disclosure may be prepared by a synthetic method known to a person skilled in the art. For example, it may be prepared by referring to the following reaction scheme 1, Korean Patent Application Laying-Open No. 2018-0012709, etc., but is not limited thereto.

[Reaction Scheme 1]

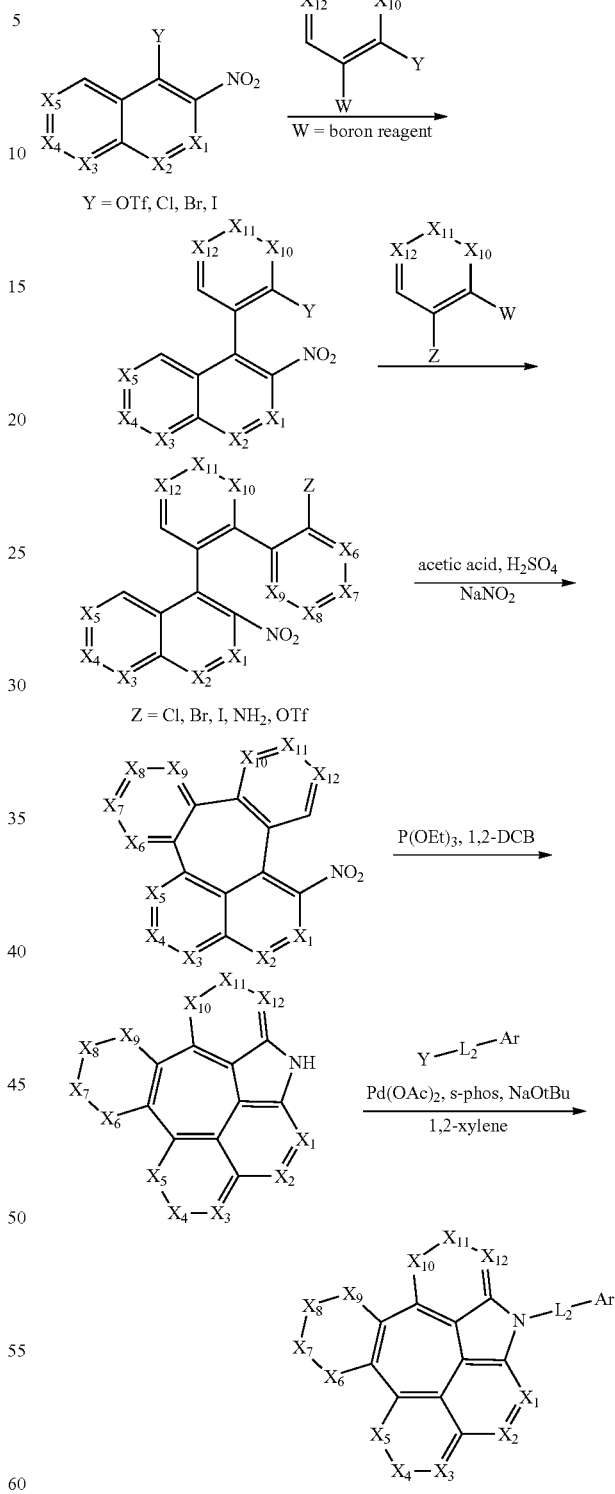

wherein $X_1$ to $X_{12}$, $L_2$, and Ar as defined as in formulas 2 and 3, and OTf represents trifluoromethanesulfonate.

The organic electroluminescent device according to the present disclosure comprises a first electrode; a second electrode; and at least one organic layer between the first and second electrodes.

One of the first and second electrodes may be an anode, and the other may be a cathode. The organic layer comprises a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Herein, the second electrode may be a transflective electrode or a reflective electrode, and may be a top emission, bottom emission, or both-sides emission type according to the material used. In addition, the hole injection layer may be further doped with a p-dopant, and the electron injection layer may be further doped with an n-dopant.

The organic electroluminescent device according to the present disclosure may comprise an anode, a cathode, and at least one organic layer between the anode and cathode, in which the organic layer may comprise a plurality of organic electroluminescent materials including a compound represented by formula 1 as the first organic electroluminescent material and a compound represented by formula 2 as the second organic electroluminescent material. The organic electroluminescent device according to the present disclosure may comprise an anode, a cathode, and at least one light-emitting layer between the anode and cathode, in which the light-emitting layer may comprise a compound represented by formula 1 and a compound represented by formula 2.

The light-emitting layer comprises a host and a dopant, and the host comprises the plurality of host materials. The compound represented by formula 1 may be comprised as a first host compound of the plurality of host materials and the compound represented by formula 2 may be comprised as a second host compound of the plurality of host materials. Herein, the weight ratio of the first host compound to the second host compound is in the range of about 1:99 to about 99:1, preferably about 10:90 to about 90:10, more preferably about 30:70 to about 70:30, even more preferably about 40:60 to about 60:40, and further more preferably about 50:50.

The light-emitting layer is a layer from which light is emitted, and can be a single layer or a multi-layer of which two or more layers are stacked. In the plurality of host materials according to the present disclosure, the first and second host materials may both be comprised in one layer or may be respectively comprised in different light-emitting layers. According to one embodiment of the present disclosure, the doping concentration of the dopant compound with respect to the host compound of the light-emitting layer may be less than 20 wt %.

The organic electroluminescent device of the present disclosure may further comprise at least one layer selected from a hole injection layer, a hole transport layer, a hole auxiliary layer, a light-emitting auxiliary layer, an electron transport layer, an electron injection layer, an interlayer, an electron buffer layer, a hole blocking layer, and an electron blocking layer. In one embodiment of the present disclosure, the organic electroluminescent device of the present disclosure may further comprise an amine-based compound, in addition to the plurality of host materials of the present disclosure, as at least one of a hole injection material, a hole transport material, a hole auxiliary material, a light-emitting material, a light-emitting auxiliary material, and an electron blocking material. In addition, in one embodiment of the present disclosure, the organic electroluminescent device of the present disclosure may further comprise an azine-based compound, in addition to the plurality of host materials of the present disclosure, as at least one of an electron transport material, an electron injection material, an electron buffer material, and a hole blocking material.

The dopant comprised in the organic electroluminescent device according to the present disclosure may be at least one phosphorescent or fluorescent dopant, and preferably phosphorescent dopant. The phosphorescent dopant material applied to the organic electroluminescent device of the present disclosure is not particularly limited, but may be selected from metallated complex compounds of iridium (Ir), osmium (Os), copper (Cu), and platinum (Pt), preferably selected from ortho-metallated complex compounds of iridium (Ir), osmium (Os), copper (Cu), and platinum (Pt), and more preferably ortho-metallated iridium complex compounds.

The dopant comprised in the organic electroluminescent device of the present disclosure may include the compound represented by the following formula 101, but is not limited thereto.

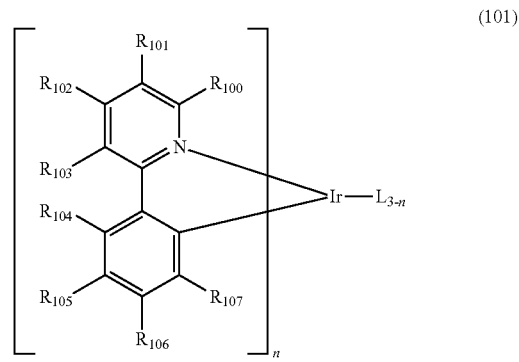

(101)

In formula 101, L is selected from the following structures 1 and 2:

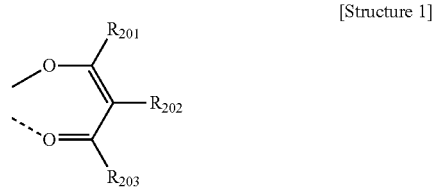

[Structure 1]

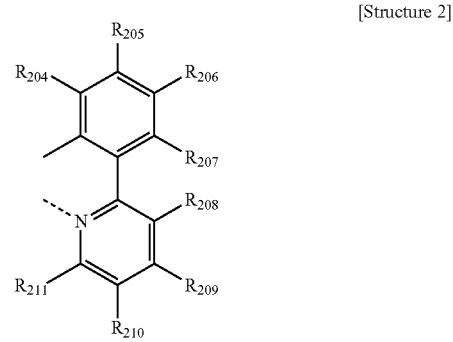

[Structure 2]

$R_{10}$ to $R_{103}$, each independently, represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent to form a ring, e.g., a substituted or unsubstituted, quinoline, benzofuropyridine, benzothienopyridine, benzothienoquinoline, or indenoquinoline ring, together with pyridine;

$R_{104}$ to $R_{107}$, each independently, represent hydrogen, deuterium, a halogen, a (C1-C30)alkyl unsubstituted or substituted with a halogen(s), a substituted or unsubstituted (C3-C30)cycloalkyl, a substituted or unsubstituted (C6-C30)aryl, a substituted or unsubstituted (3- to 30-membered) heteroaryl, a cyano, or a substituted or unsubstituted (C1-C30)alkoxy; or may be linked to an adjacent substituent to form a ring, e.g., a substituted or unsubstituted, naphthyl, fluorene, dibenzothiophene, dibenzofuran, indenopyridine, benzofuropyridine or benzothienopyridine ring, together with benzene;

$R_{201}$ to $R_{211}$, each independently, represent hydrogen, deuterium, a halogen, a (C1-C30)alkyl unsubstituted or substituted with a halogen(s), a substituted or unsubstituted (C3-C30)cycloalkyl, or a substituted or unsubstituted (C6-C30)aryl; or may be linked to an adjacent substituent to form a ring; and n represents an integer of 1 to 3.

The specific examples of the dopant compound are as follows, but are not limited thereto D-1
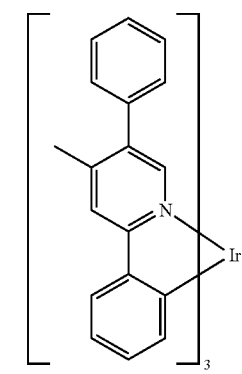

D-2
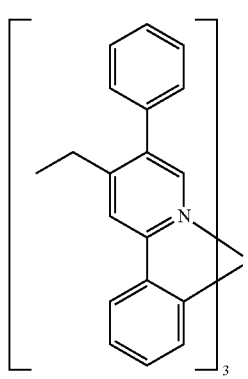

D-3
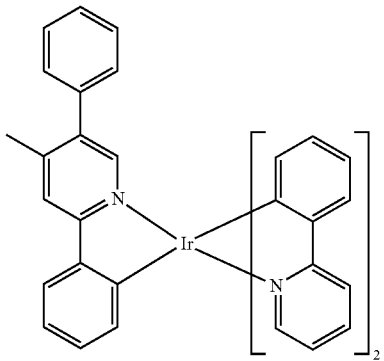

D-4
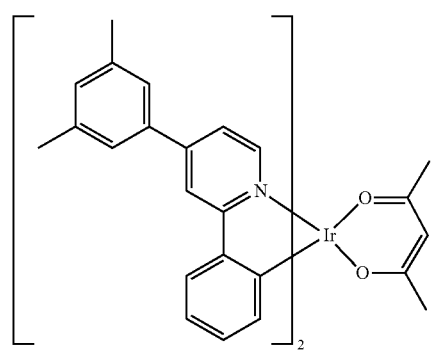

D-5
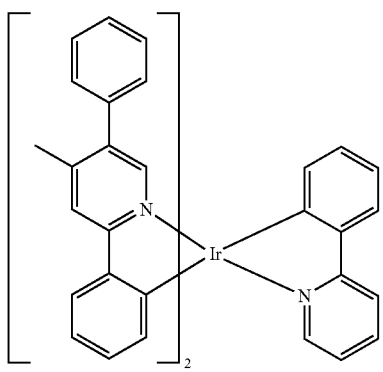

D-6
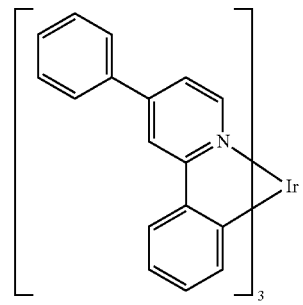

-continued
D-7
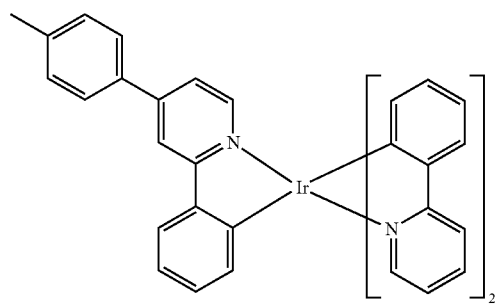
D-8
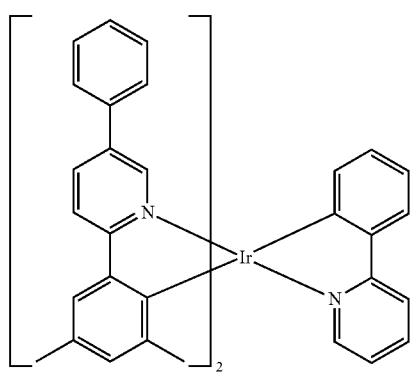
D-9
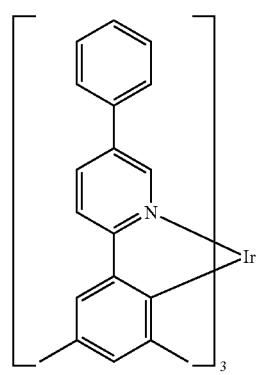
D-10
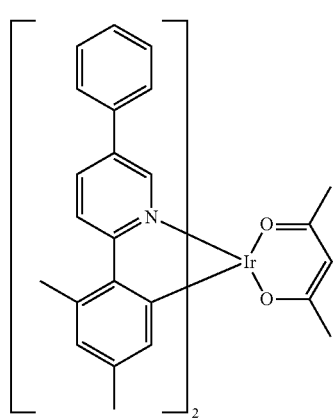
-continued
D-11
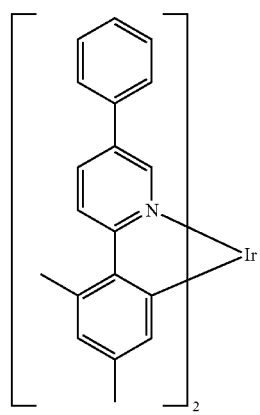
D-12
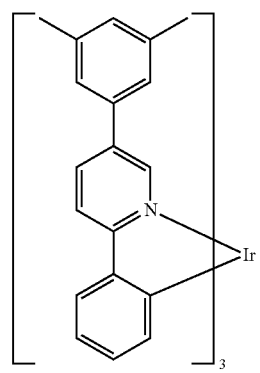
D-13
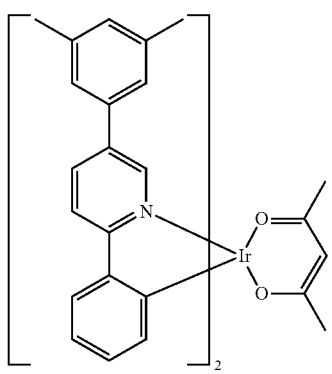
D-14
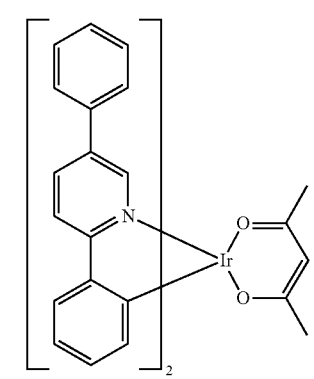

D-15 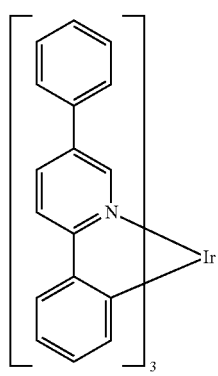
D-19 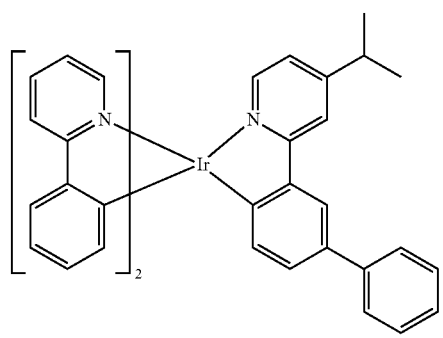
D-16 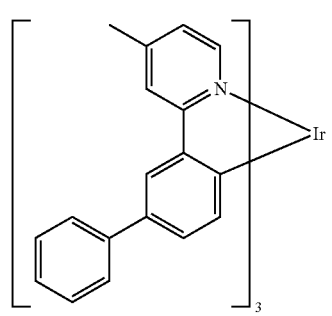
D-20 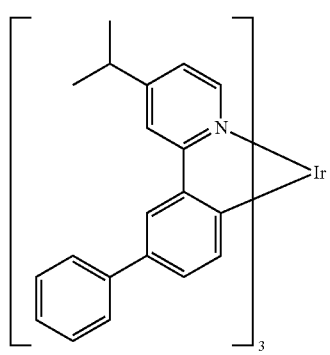
D-17 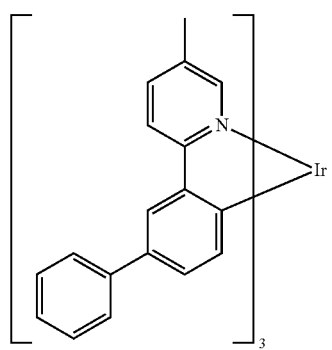
D-21 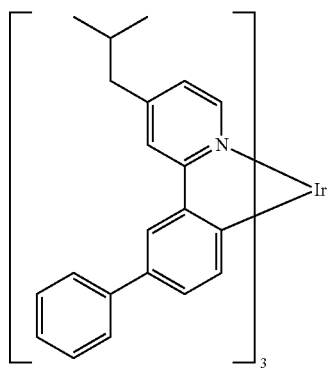
D-18 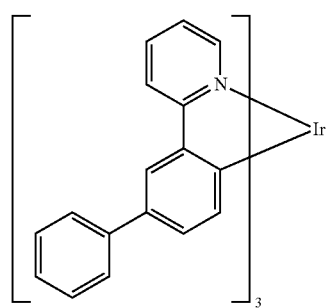
D-22 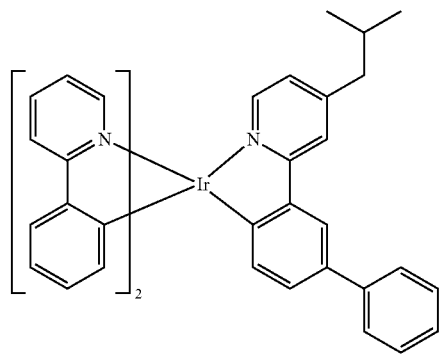

D-23
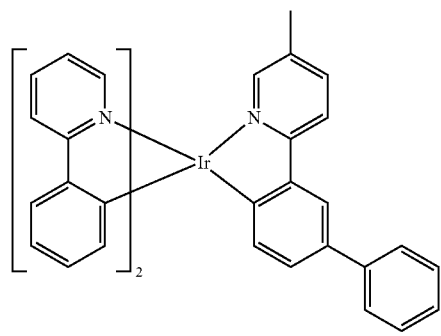
D-27
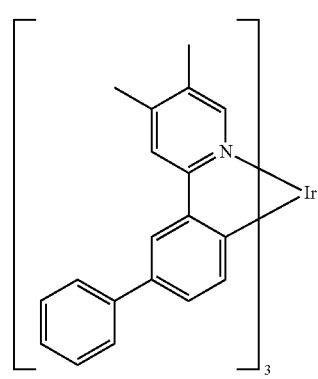
D-24
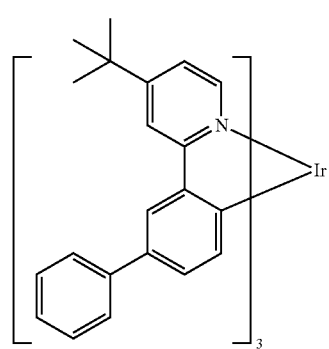
D-28
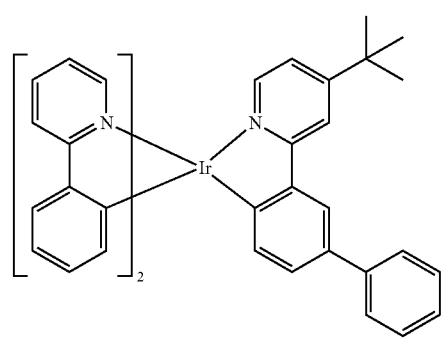
D-25
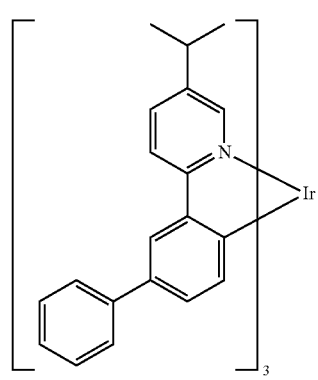
D-29
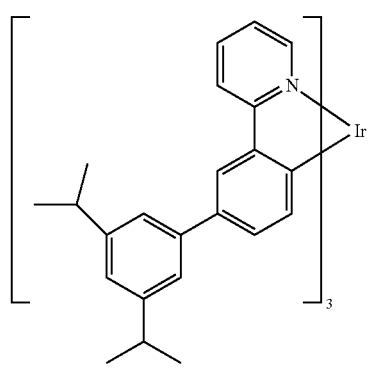
D-26
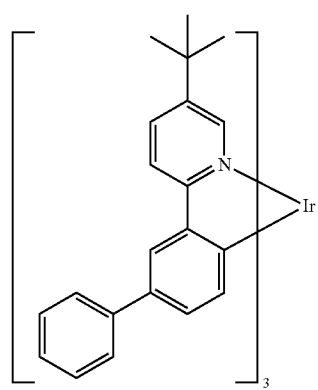
D-30
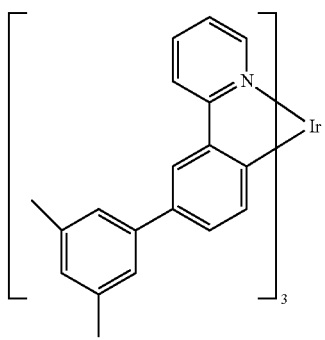

D-31 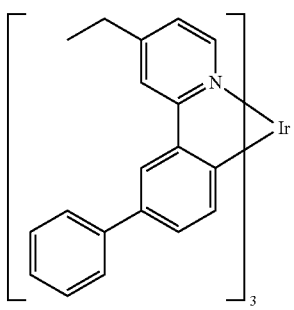
D-32 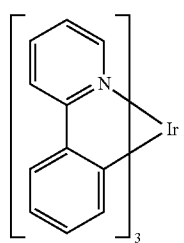
D-33 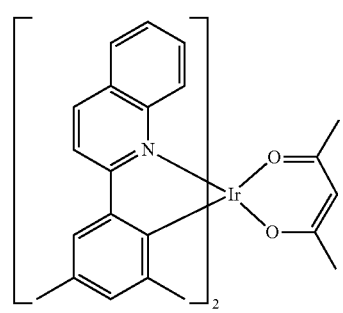
D-34 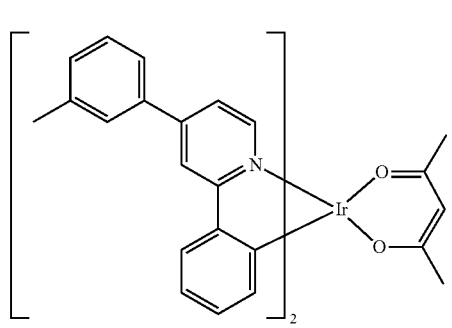
D-35 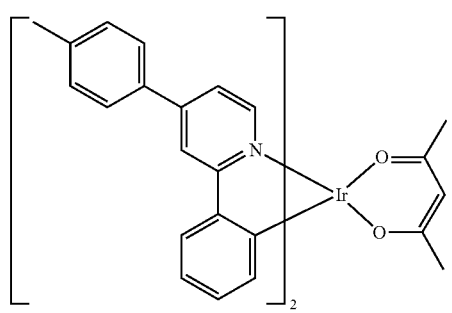
D-36 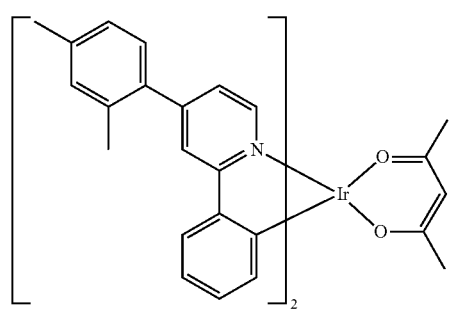
D-37 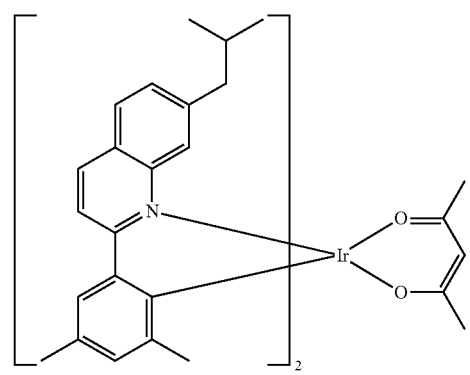
D-38 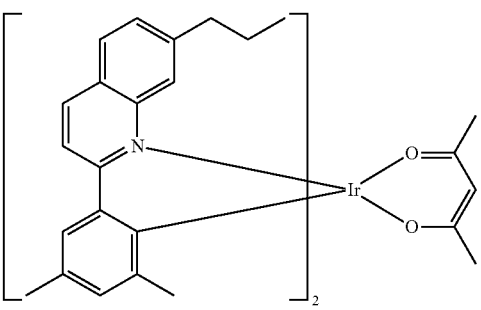
D-39 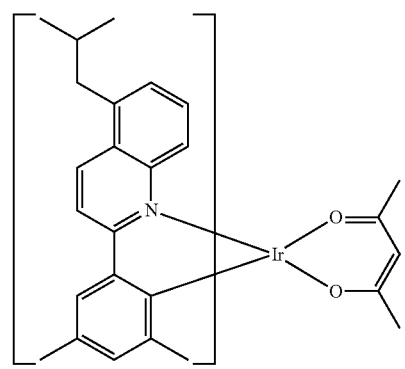

D-40
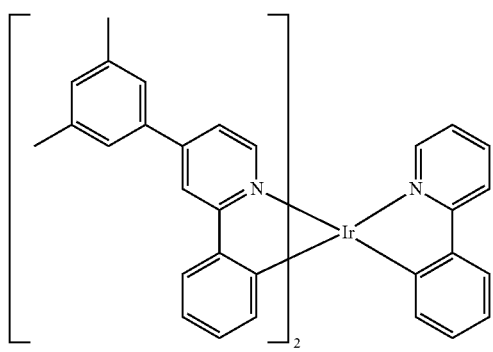
D-41
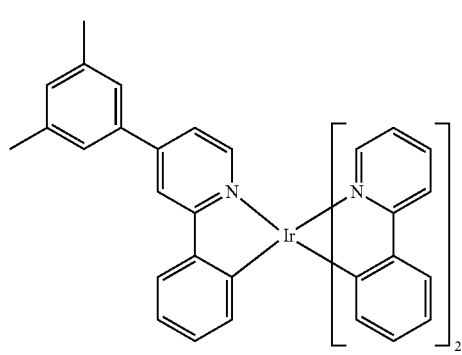
D-42
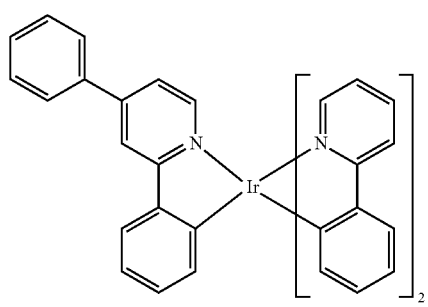
D-43
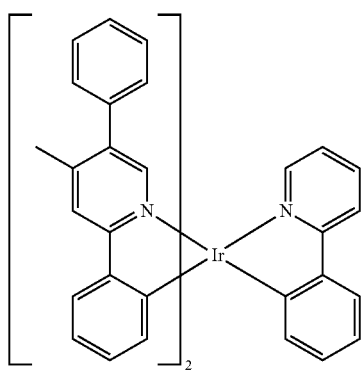
D-44
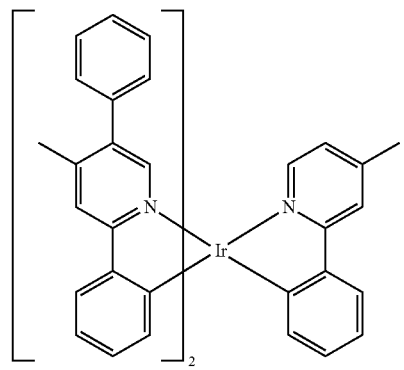
D-45
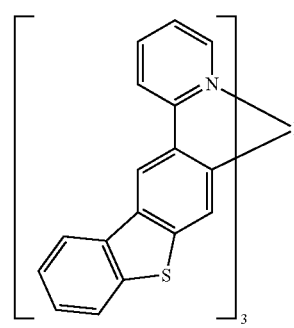
D-46
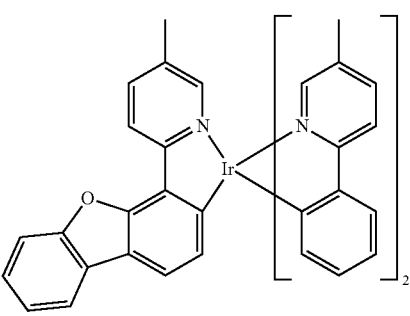
D-47
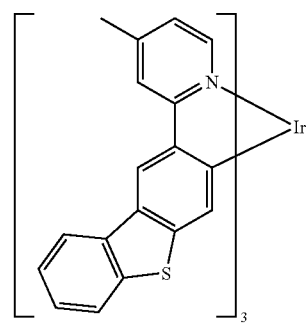
D-48
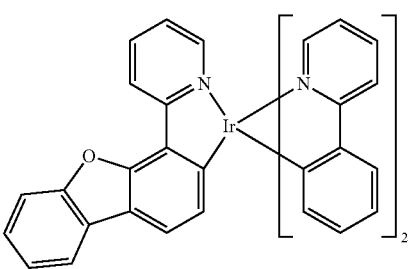

D-49
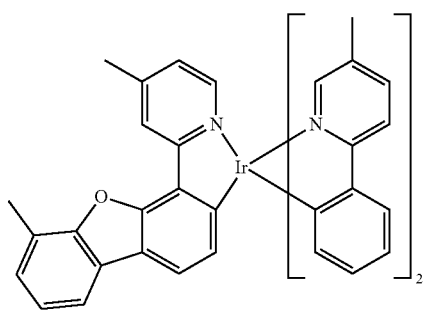
D-50
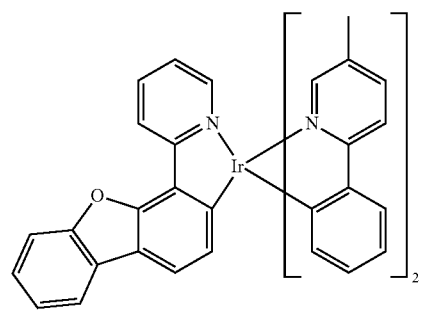
D-51
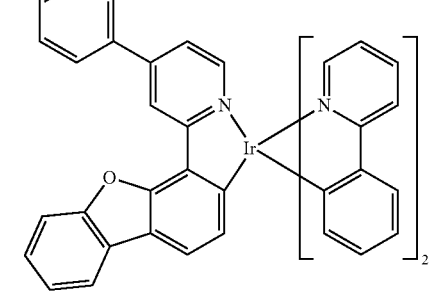
D-52
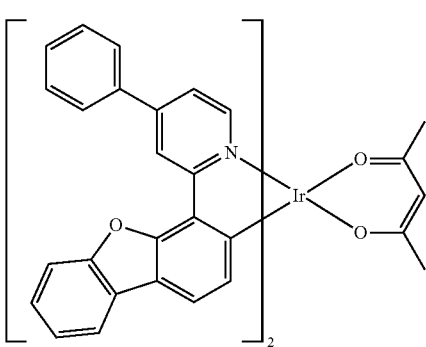
D-53
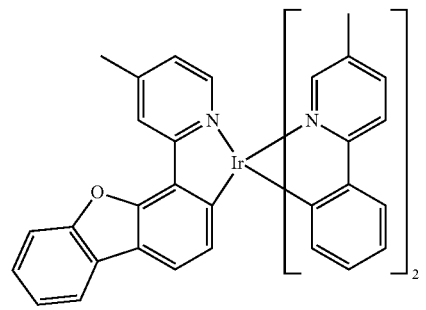
D-54
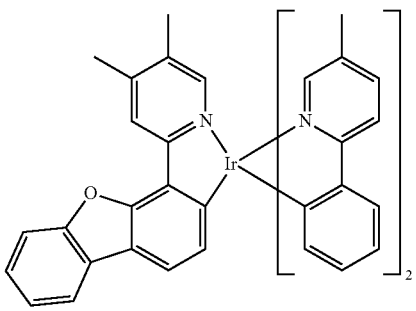
D-55
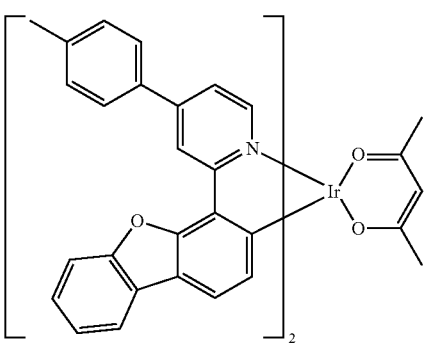
D-56
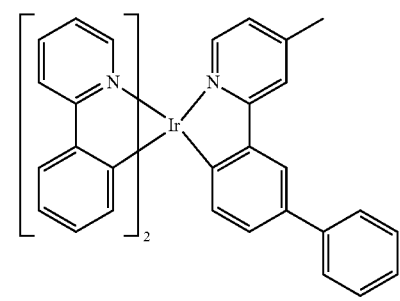
D-57
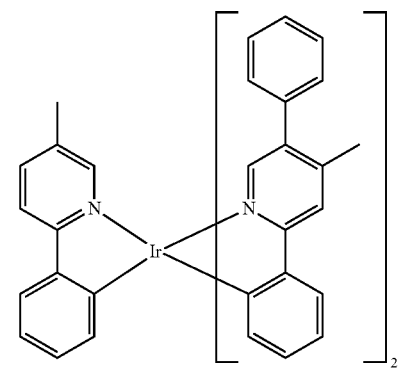

-continued
D-58
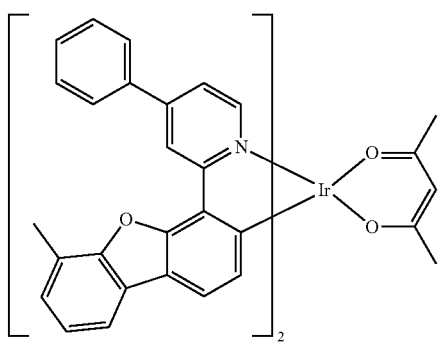
D-59
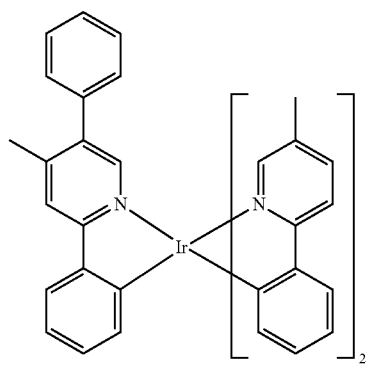
D-60
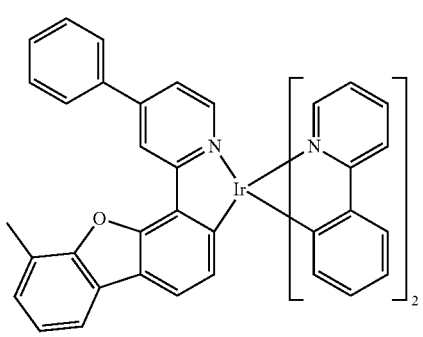
D-61
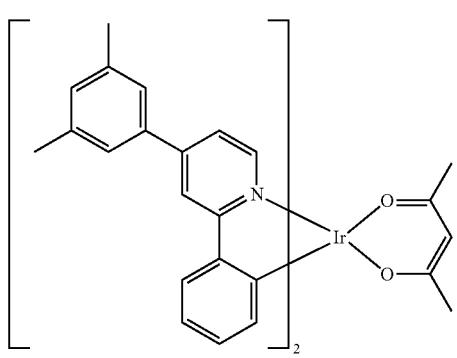
-continued
D-62
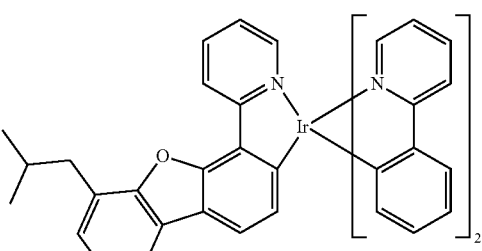
D-63
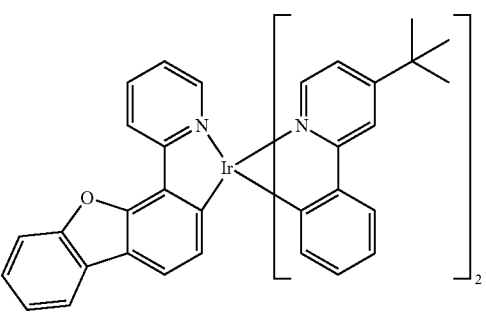
D-64
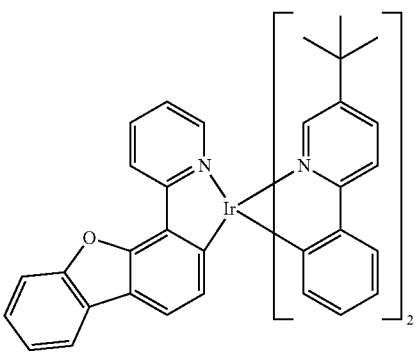
D-65
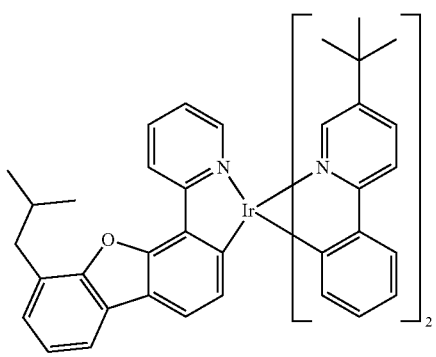

D-66
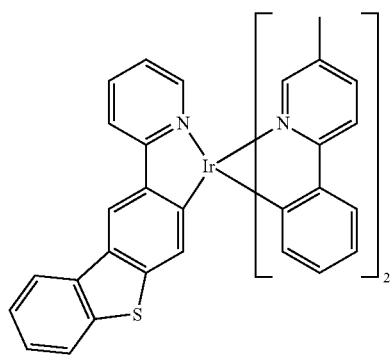
D-67
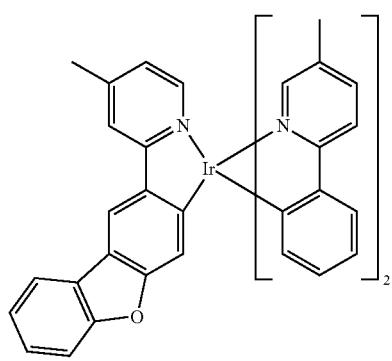
D-68
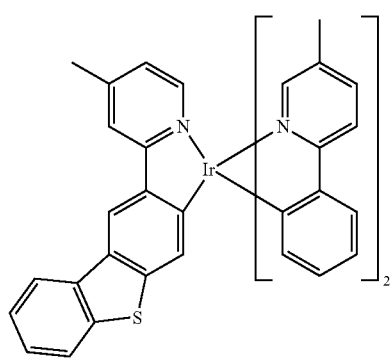
D-69
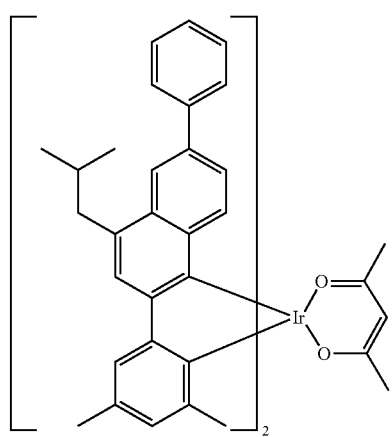
D-70
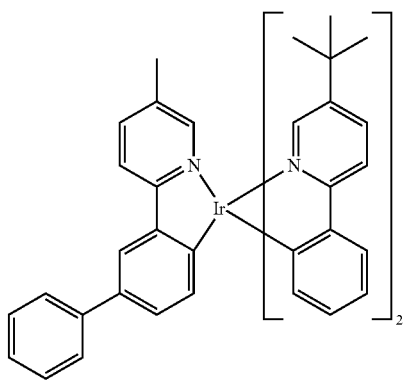
D-71
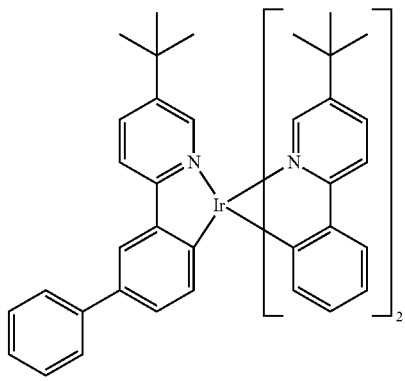
D-72
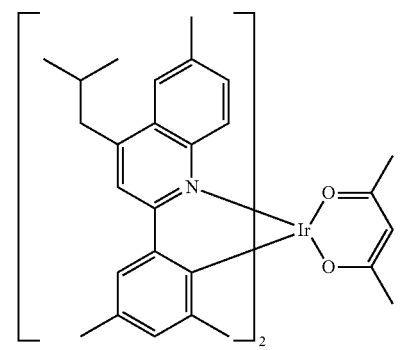
D-73
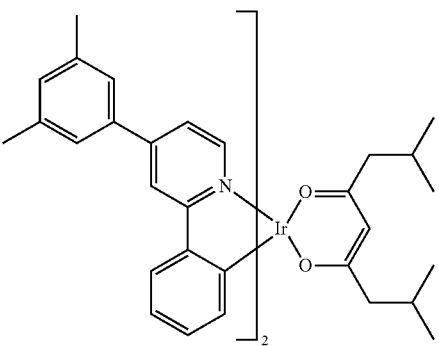

-continued
D-74
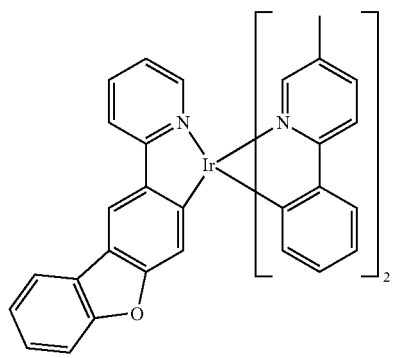
D-75
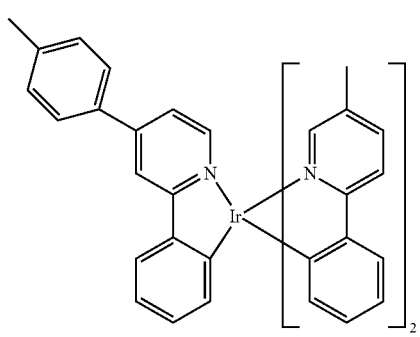
D-76
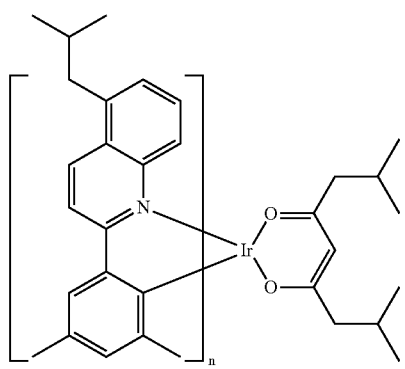
D-77
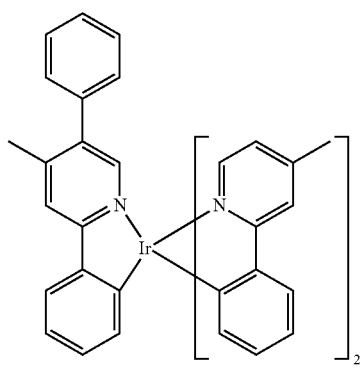
-continued
D-78
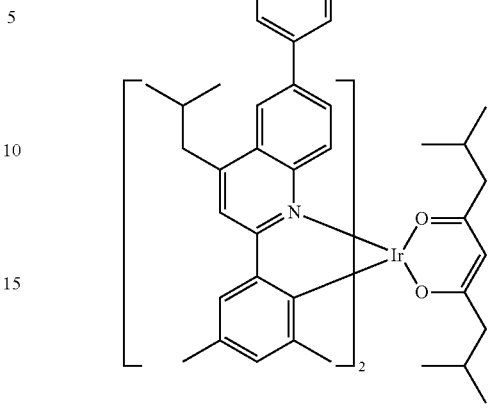
D-79
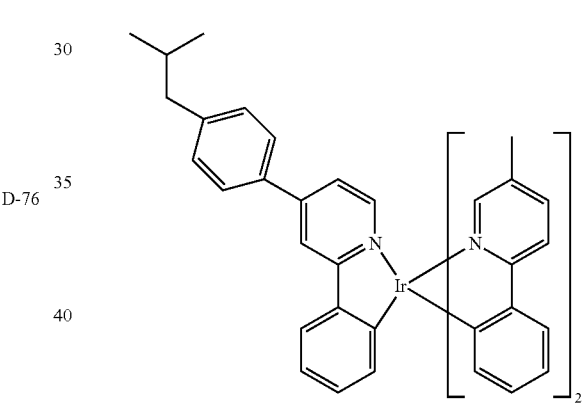
D-80
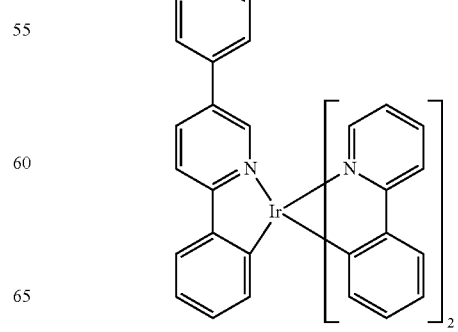

-continued
D-81
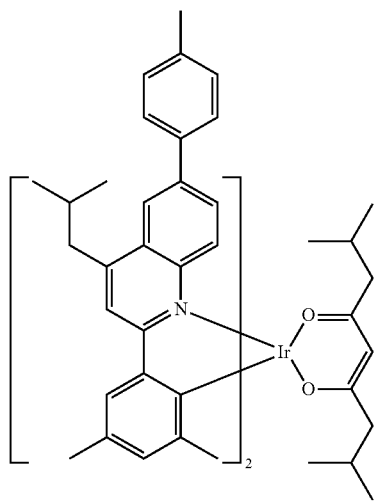
D-82
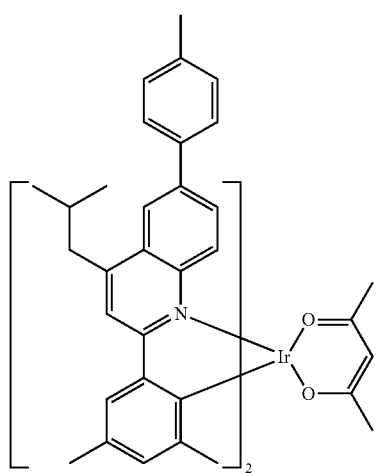
D-83
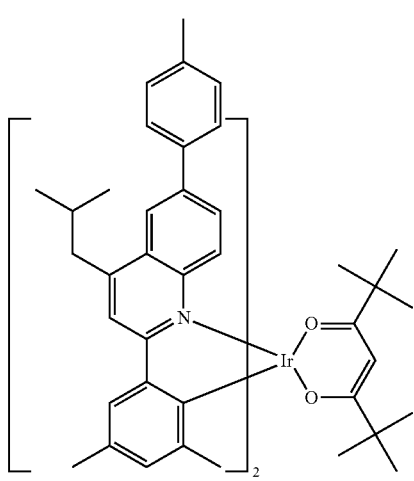
-continued
D-84
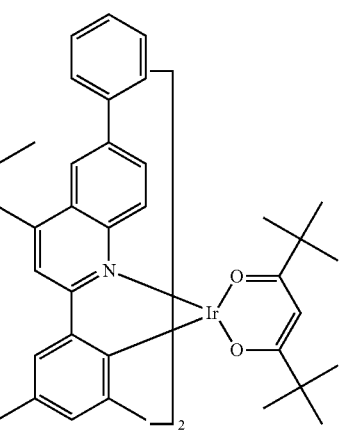
D-85
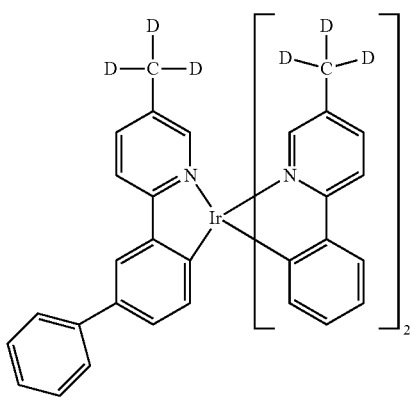
D-86
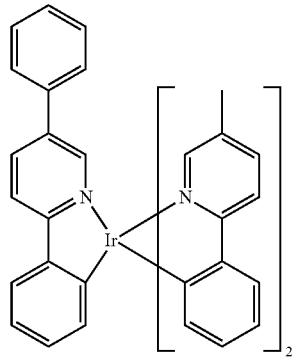
D-87
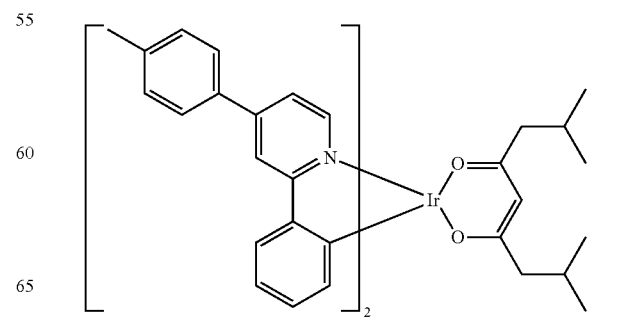

D-88
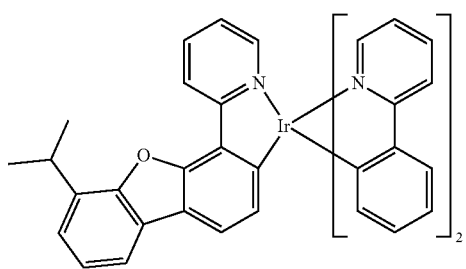
D-89
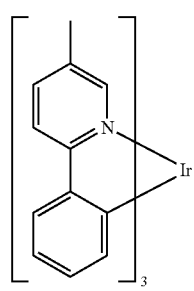
D-90
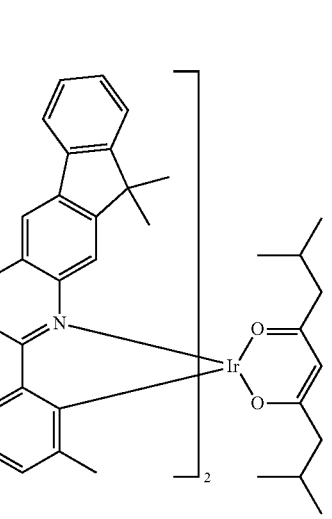
D-91
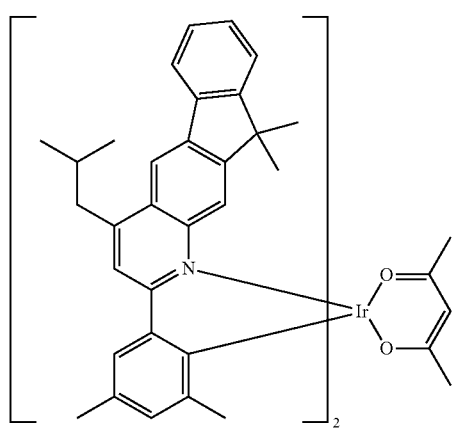
D-92
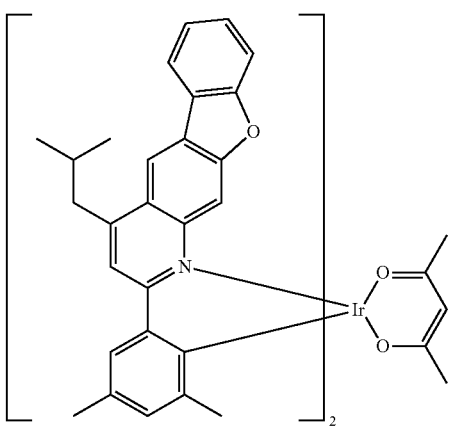
D-93
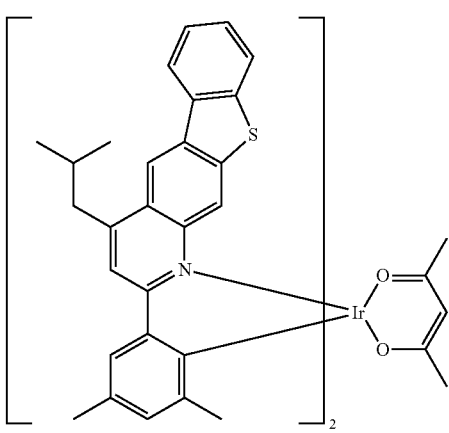
D-94
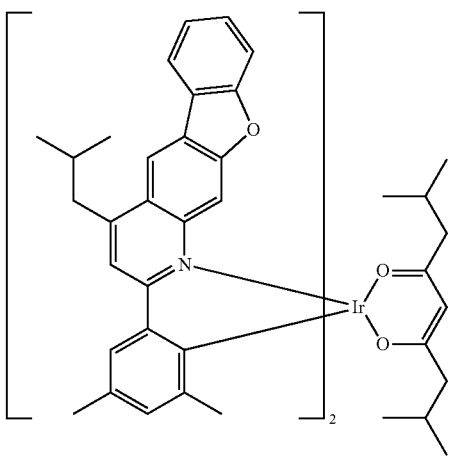

-continued
D-95
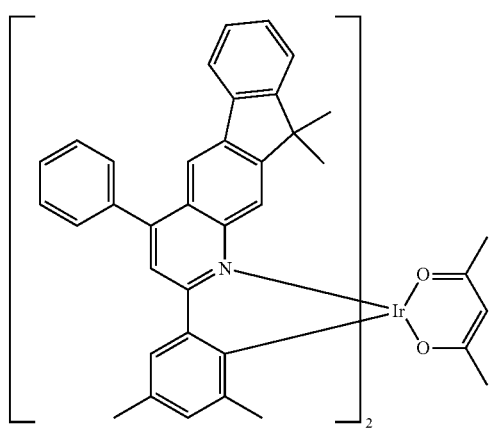
D-96
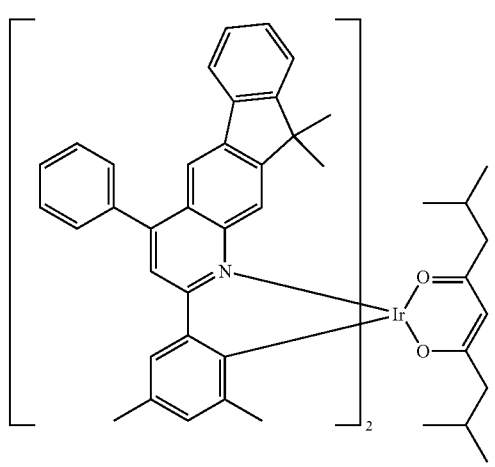
D-97
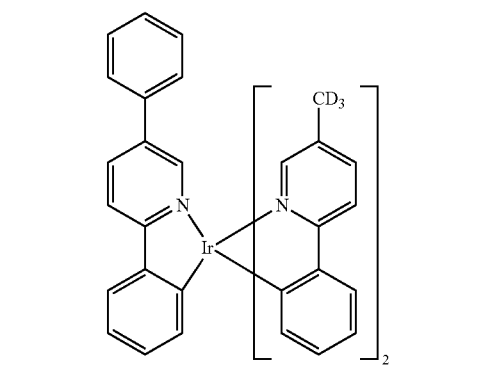
D-98
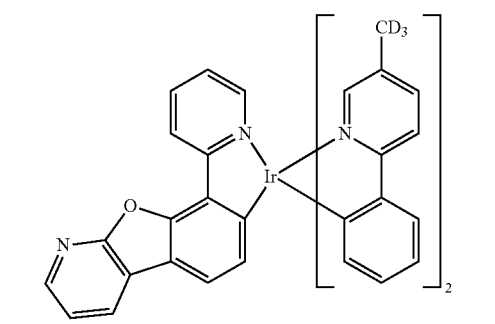
-continued
D-99
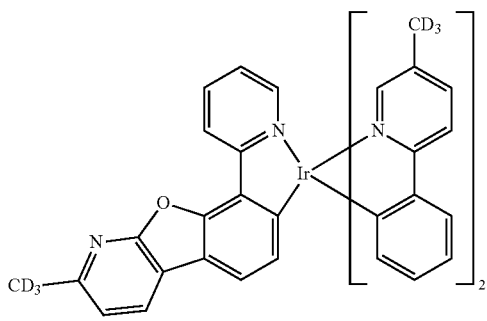
D-100
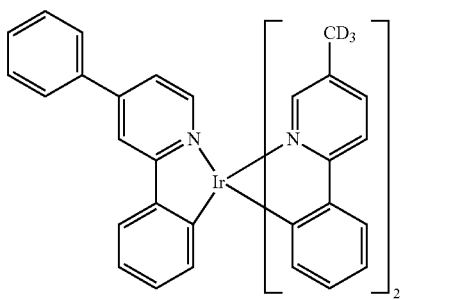
D-101
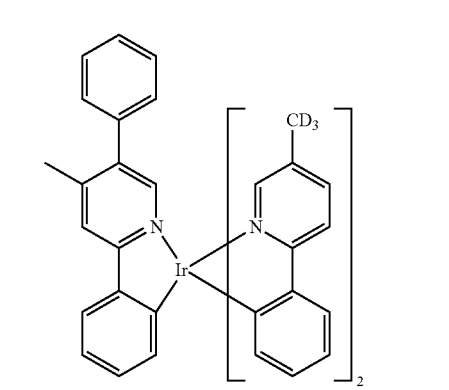
D-102
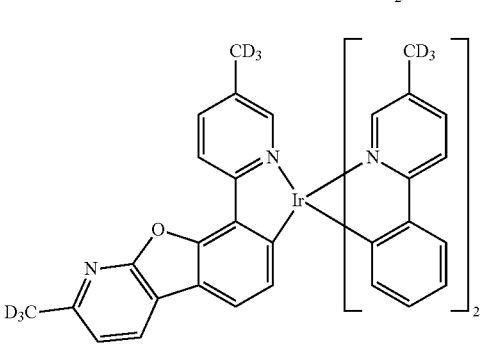
D-103
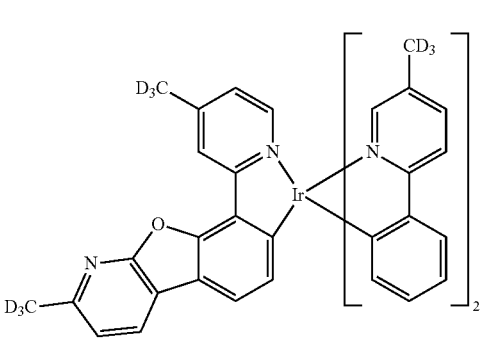

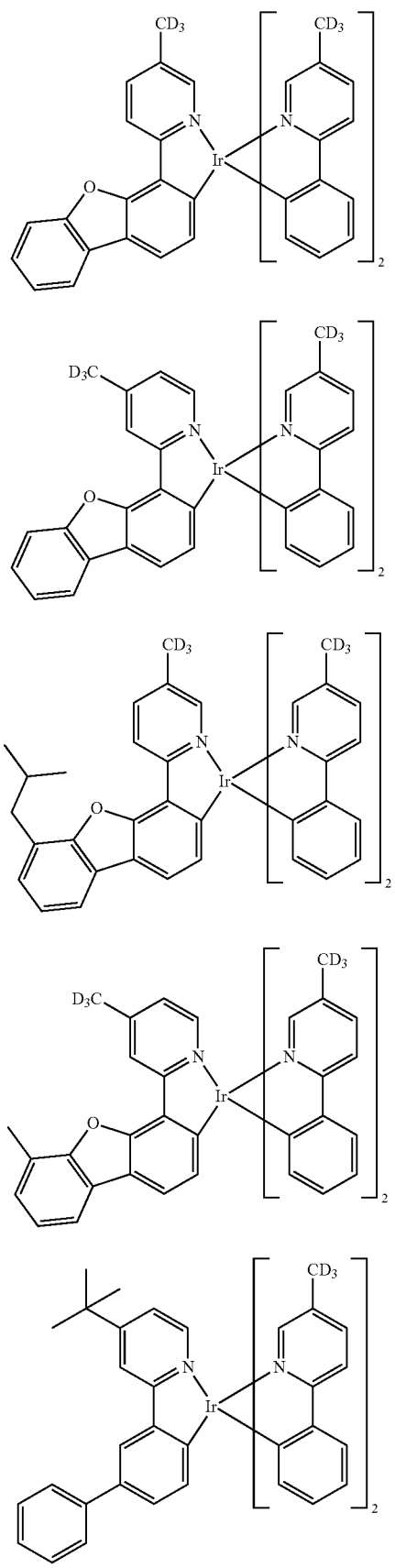
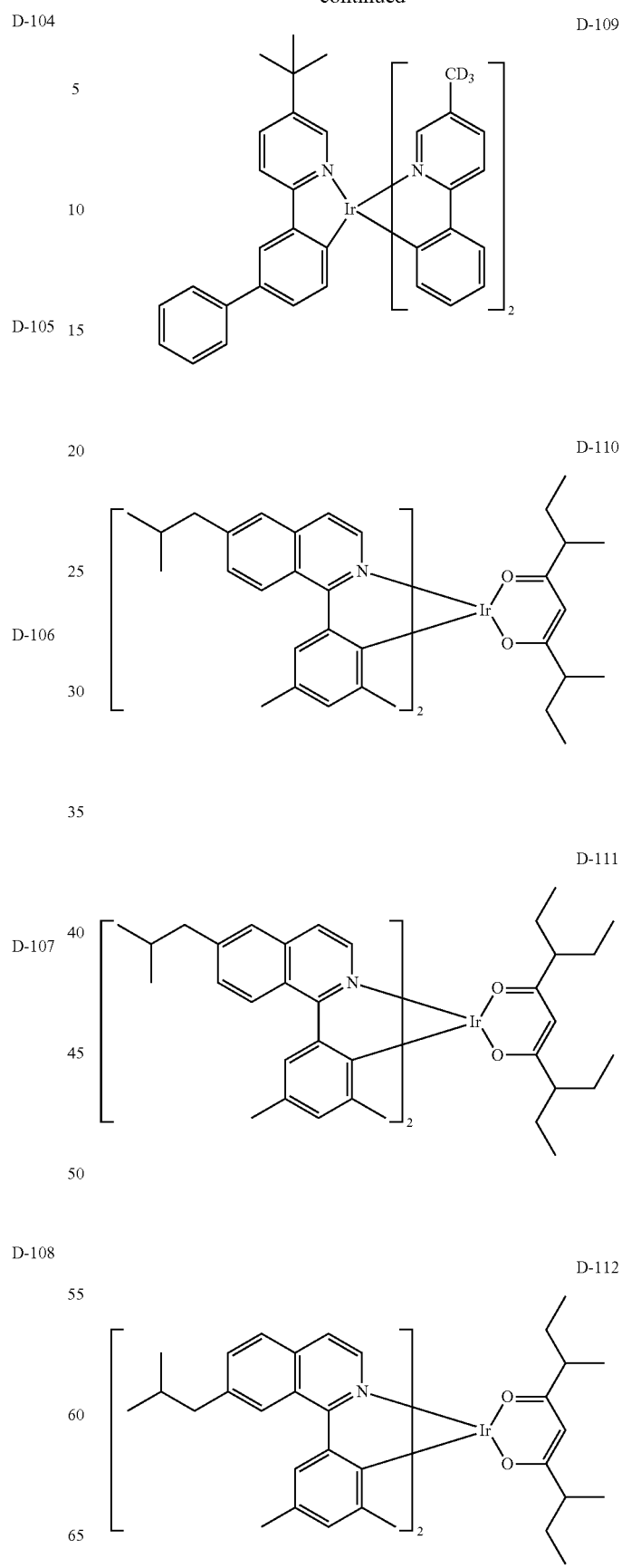

D-113

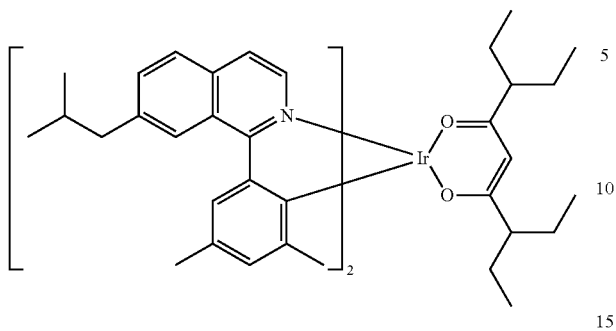

D-117

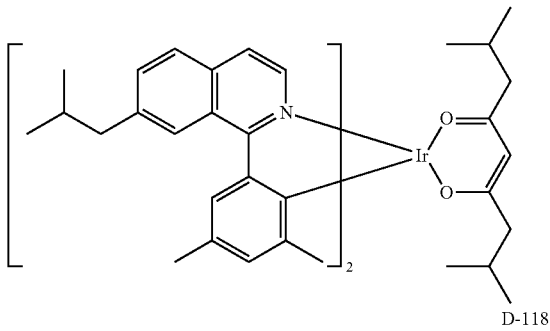

D-114

D-118

D-115

D-119

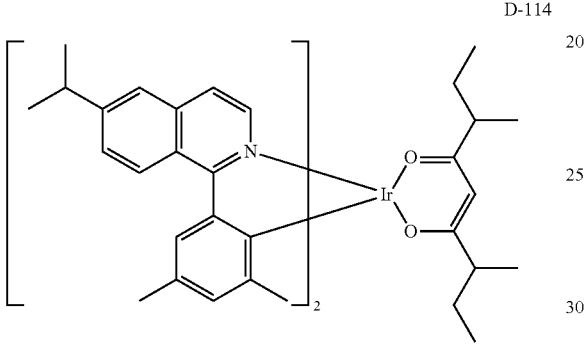

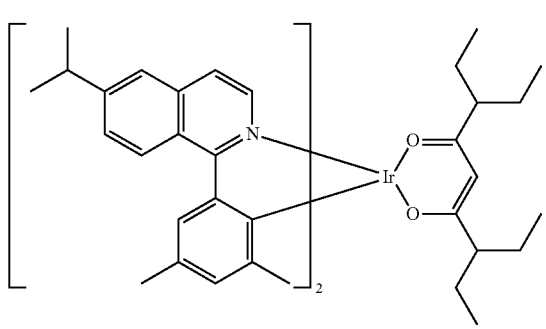

D-116

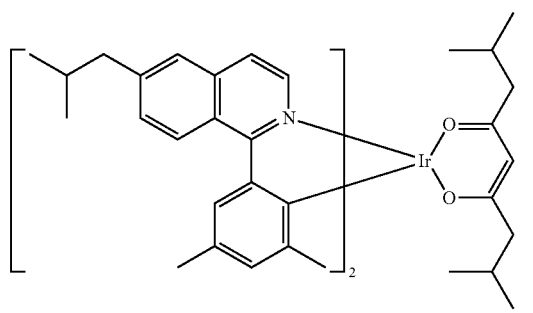

In the organic electroluminescent device of the present disclosure, between the anode and the light-emitting layer, a hole injection layer, a hole transport layer, an electron blocking layer, or a combination thereof can be used. Multiple hole injection layers can be used in order to lower the hole injection barrier (or hole injection voltage) from the anode to the hole transport layer or the electron blocking layer. Two compounds can be simultaneously used in each layer. The hole transport layer or the electron blocking layer can also be formed of multi-layers.

In addition, between the light-emitting layer and the cathode, an electron buffer layer, a hole blocking layer, an electron transport layer, an electron injection layer, or a combination thereof can be used. Multiple electron buffer layers can be used in order to control the injection of the electrons and enhance the interfacial characteristics between the light-emitting layer and the electron injection layer. Two compounds can be simultaneously used in each layer. The hole blocking layer or the electron transport layer can also be formed of multi-layers, and each layer can comprise two or more compounds.

In addition, the organic electroluminescent compound or the plurality of host materials according to the present disclosure can also be used in an organic electroluminescent device comprising a quantum dot (QD).

In order to form each layer of the organic electroluminescent device of the present disclosure, dry film-forming methods such as vacuum evaporation, sputtering, plasma and ion plating methods, or wet film-forming methods such as ink jet printing, nozzle printing, slot coating, spin coating, dip coating, and flow coating methods can be used.

When using a solvent in a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

In addition, the first and the second host compounds of the present disclosure may be film-formed in the above-listed methods, commonly by a co-evaporation process or a mixture-evaporation process. The co-evaporation is a mixed deposition method in which two or more materials are placed in a respective individual crucible source and a current is applied to both cells at the same time to evaporate the materials. The mixture-evaporation is a mixed deposition method in which two or more materials are mixed in one crucible source before evaporating them, and a current is applied to the cell to evaporate the materials. Further, if the first and the second host compounds are present in the same layer or different layers in an organic electroluminescent device, the two host compounds may individually form films. For example, the second host compound may be deposited after depositing the first host compound.

The present disclosure may provide a display device by using the plurality of host materials comprising the compound represented by formula 1 and the compound represented by formula 2. That is, it is possible to manufacture a display system or a lighting system by using the plurality of host materials of the present disclosure. Specifically, it is possible to produce a display system, e.g., a display system for smartphones, tablets, notebooks, PCs, TVs, or cars, or a lighting system, e.g., an outdoor or indoor lighting system, by using the plurality of host materials of the present disclosure.

Hereinafter, the preparation method of the compound of the present disclosure and the properties thereof, and the properties of an organic electroluminescent device comprising the plurality of host materials of the present disclosure will be explained in detail with reference to the representative compounds of the present disclosure. However, the present disclosure is not limited by the following examples.

Synthesis Example 1: Preparation of Compound H-49

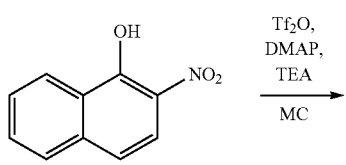

-continued

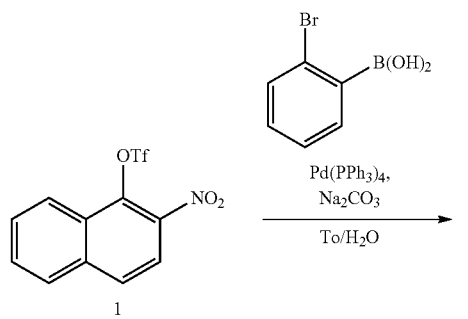

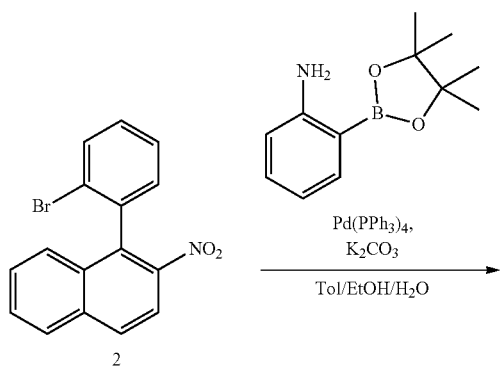

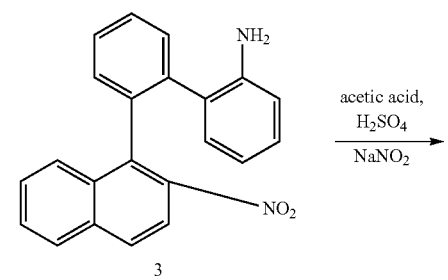

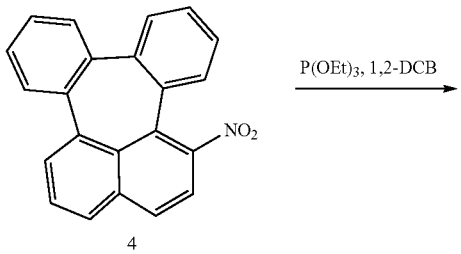

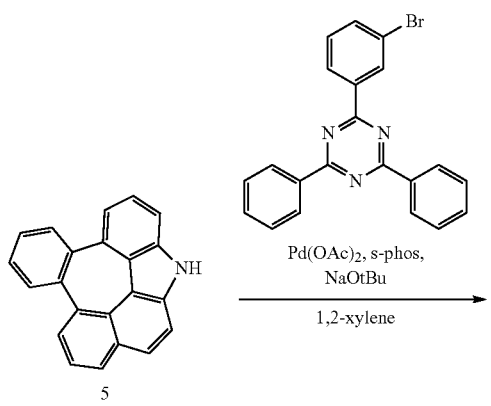

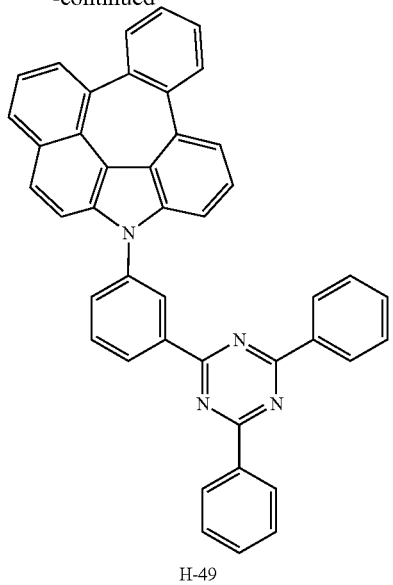

H-49

Synthesis of Compound 1

70 g of 2-nitro-1-naphthol (370 mmol) and 4.5 g of dimethylaminopyridine (DMAP) (37 mmol) were dissolved in 1800 mL of methylene chloride (MC) in a flask, 62 mL of triethylamine (TEA) (444 mmol) were added dropwise at 0° C. and stirred for 20 minutes, 125.3 g of trifluoromethane sulfonic anhydride (444 mmol) was slowly added dropwise to the reactant at the same temperature and stirred for 1 hour. After the reaction was completed, an organic layer was extracted with MC, and residual moisture was removed by using magnesium sulfate. The residue was dried and separated by column chromatography to obtain 96.2 g of compound 1 (yield: 81%).

Synthesis of Compound 2

96.2 g of compound 1 (299 mmol), 72.1 g of 2-bromophenylboronic acid (359 mmol), 17.3 g of tetrakis(triphenylphosphine)palladium(0) (15 mmol), and 79.3 g of sodium carbonate (749 mmol) were dissolved in 1400 mL of toluene, 350 mL of ethanol, and 350 mL of water in a flask and refluxed for 1 hour. After the reaction was completed, an organic layer was extracted with ethyl acetate, and residual moisture was removed by using magnesium sulfate. The residue was dried and separated by column chromatography to obtain 98 g of compound 2 (yield: 99%).

Synthesis of Compound 3

98 g of compound 2 (299 mmol), 78.5 g of 2-aminophenylboronic acid pinacol ester (358 mmol), 17.2 g of tetrakis(triphenylphosphine)palladium(0) (15 mmol), and 103 g of potassium carbonate (747 mmol) were dissolved in 1300 mL of toluene, 350 mL of ethanol, and 350 mL of water in a flask and refluxed for 20 hours. After the reaction was completed, an organic layer was extracted with ethyl acetate, and residual moisture was removed by using magnesium sulfate. The residue was dried and separated by column chromatography to obtain 54 g of compound 3 (yield: 53%).

Synthesis of Compound 4

25 g of compound 3 (73 mmol) was dissolved in 250 mL of acetic acid and 25 mL of sulfuric acid in a flask, 6.5 g of sodium nitrite (95 mmol) was slowly added dropwise at 0° C. and stirred for 40 minutes. After the reaction was completed, the reaction product was added dropwise to water and filtered to remove moisture. The residue was dried and separated by column chromatography to obtain 2 g of compound 4 (yield: 8.4%).

Synthesis of Compound 5

4.7 g of compound 4 (15 mmol) was dissolved in 48 mL of triethylphosphite and 48 mL of 1,2-dichlorobenzene in a flask and refluxed for 3 hours. After the reaction was completed, an organic layer was extracted with ethyl acetate after distillation under reduced pressure, and residual moisture was removed by using magnesium sulfate. The residue was dried and separated by column chromatography to obtain 2.7 g of compound 5 (yield: 63%).

Synthesis of Compound H-49

2.1 g of compound 5 (7 mmol), 3.1 g of 2-(3-bromophenyl)-4,6-diphenyl-1,3,5-triazine (8 mmol), 0.81 g of palladium (II) acetate (0.36 mmol), 0.3 g of 2-dicyclohexylphosphino-2',6'-dimethoxybiphenyl (S-Phos) (0.7 mmol), and 1.7 g of sodium tert-butoxide (18 mmol) were dissolved in 72 mL of 1,2-xylene in a flask and refluxed for 4 hours. After the reaction was completed, an organic layer was extracted with ethyl acetate after distillation under reduced pressure, and residual moisture was removed by using magnesium sulfate. The residue was dried and separated by column chromatography to obtain 2.5 g of compound H-49 (yield: 58%).

| Compound | MW | UV | PL | M.P. | Tg |
| --- | --- | --- | --- | --- | --- |
| H-49 | 598.71 | 308 nm | 495 nm | 285° C. | 132.37° C. |

Synthesis Example 2: Preparation of Compound H-6

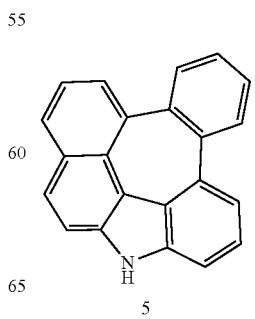 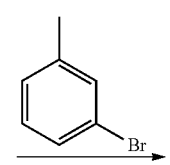

139

-continued

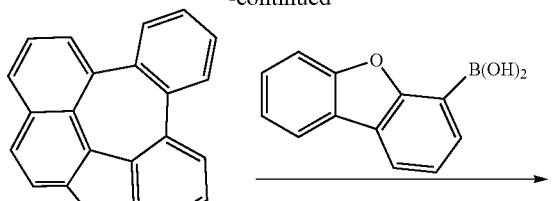

6

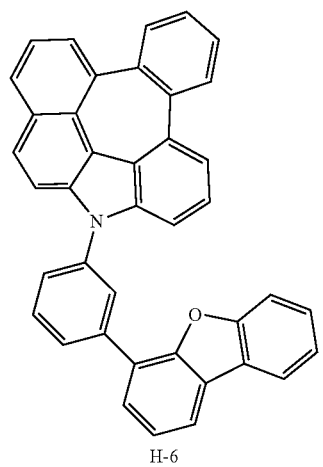

H-6

Synthesis of Compound 6

155 mL of toluene was added to 9 g of compound 5 (30.89 mmol), 10.6 g of 1-bromo-3-iodobenzene (61.78 mmol), 3 g of CuI (15.44 mmol), 1.8 g of ethylenediamine (EDA) (30.89 mmol), and 16.4 g of $K_3PO4$ (77.22 mmol) and stirred under reflux for one day. After the reaction was completed, the reaction product was cooled to room temperature, and the resulting solid was filtered under reduced pressure. The solid was dissolved in $CHCl_3$ and separated by column chromatography using MC/Hex to obtain 10 g of compound 6 (yield: 75%).

Synthesis of Compound H-6

50 mL of toluene, 13 mL of EtOH, and 13 mL of purified water were added to 5.7 g of compound 6 (12.77 mmol), 0.73 g of $Pd(PPh_3)_4$ (0.638 mmol), and 3.5 g of $K_2CO_3$ (25.54 mmol) and stirred under reflux for 2 hours. After the reaction was completed, the reaction product was cooled to room temperature, and the resulting solid was filtered under reduced pressure. The solid was dissolved in $CHCl_3$ and separated by column chromatography using MC/Hex to obtain 2.9 g of compound H-6 (yield: 43%).

$^1$H NMR (600 MHz, DMSO-$d_6$,δ) 8.232-8.206 (m, 3H), 8.111-8.098 (d, 1H), 7.962-7.946 (m, 1H), 7.929-7.903 (m, 3H), 7.896-7.882 (d, 1H), 7.806-7.802 (d, 2H), 7.783-7.759 (t, 2H), 7.738-7.723 (d, 1H), 7.635-7.620 (m, 1H), 7.581-7.548 (m, 2H), 7.513-7.440 (m, 6H)

140

| Compound | MW | Tg | M.P. |
|---|---|---|---|
| H-6 | 533.6 | 119° C. | 208° C. |

Synthesis Example 3: Preparation of Compound H-7

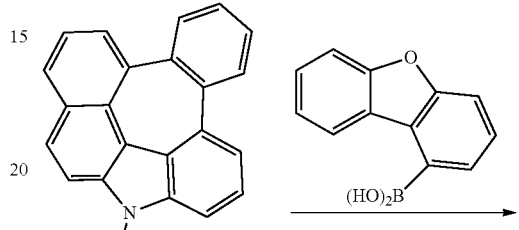

6

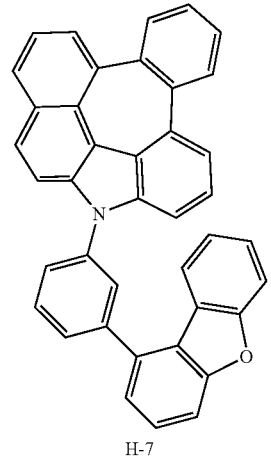

H-7

6.6 g of compound 6 (14.78 mmol), 3.4 g of dibenzo[b,d]furan-1-yl boronic acid (16.24 mmol), 0.85 g of $Pd(PPh_3)_4$ (0.739 mmol), and 4 g of $K_2CO_3$ (29.57 mmol) were added to 60 mL of toluene, 15 mL of ethanol, and 15 mL of purified water and stirred under reflux for one day. After the reaction was completed, the reaction product was cooled to room temperature, and the resulting solid was filtered under reduced pressure. The filtered solid was dissolved in $CHCl_3$, extracted with MC/Hex, and separated by column chromatography to obtain 3.5 g of compound H-7 (yield: 45%).

$^1$H NMR (600 MHz, DMSO,δ) 7.953-7.927 (m, 2H), 7.896-7.872 (t, 2H), 7.848-7.810 (m, 3H), 7.793-7.746 (m, 4H), 7.656-7.601 (m, 4H), 7.539-7.511 (t, 1H), 7.485-7.443 (m, 4H), 7.419-7.393 (t, 1H), 7.369-7.356 (d, 1H), 7.294-7.269 (t, 1H)

Synthesis Example 4: Preparation of Compound H-1

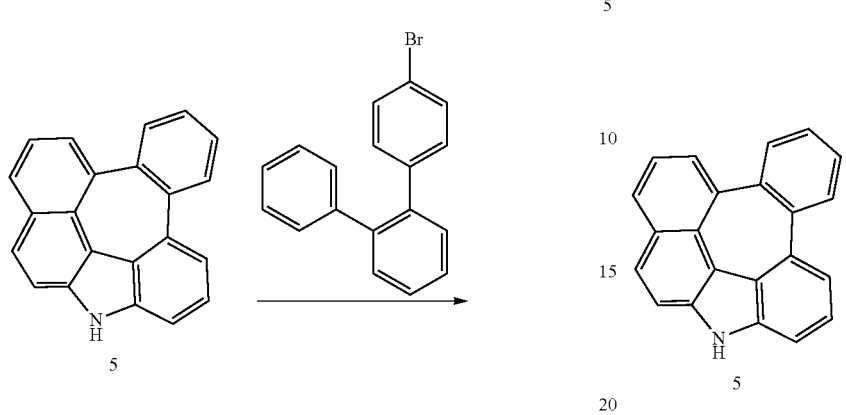

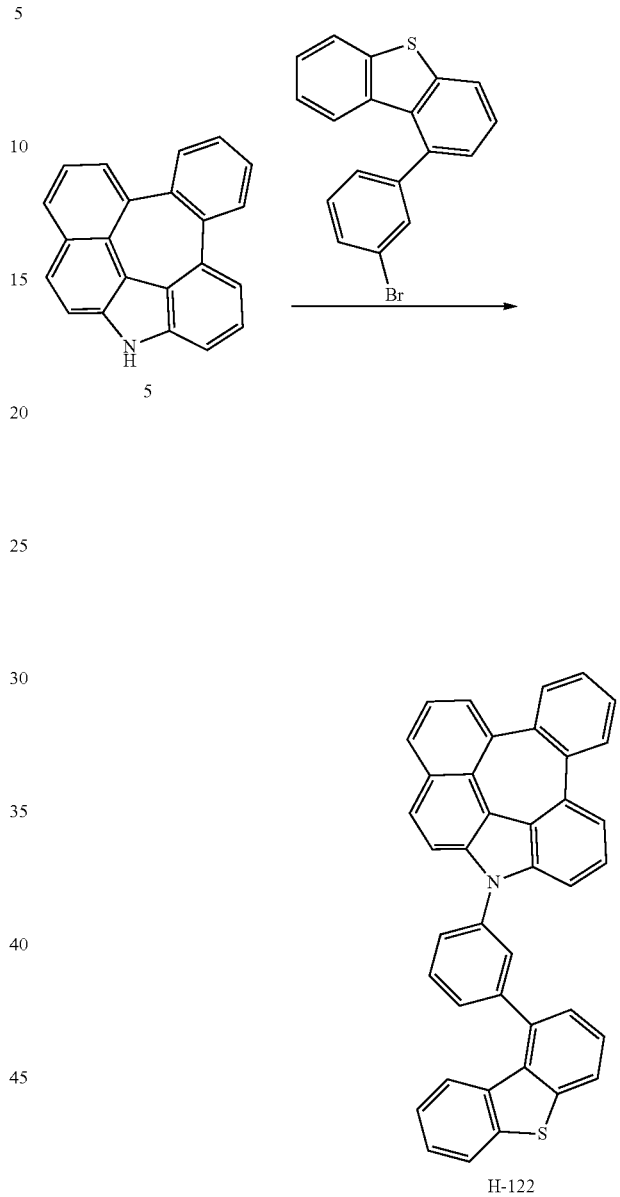

86 mL of o-xylene was added to 5 g of compound 5 (17.16 mmol), 5.3 g of 4-bromo-1,1':2',1''-terphenyl (17.16 mmol), 0.8 g of Pd$_2$(dba)$_3$ (0.858 mmol), 0.7 g of 2-dicyclohexylphosphino-2',6'-dimethoxybiphenyl (s-phos) (1.716 mmol), and 5 g of NaOt-Bu (51.48 mmol) and stirred under reflux for 2 hours. After the reaction was completed, the reaction product was cooled to room temperature, and the resulting solid was filtered under reduced pressure. The filtered solid was dissolved in CHCl$_3$, extracted with MC/Hex, and separated by column chromatography to obtain 2.4 g of compound H-1 (yield: 26%).

$^1$H NMR (DMSO-d$_6$) δ: 7.92-7.88 (m, 1H), 7.87-7.83 (m, 1H), 7.79 (d, J=9.1 Hz, 1H), 7.74 (t, J=8.3 Hz, 2H), 7.59-7.54 (m, 2H), 7.53-7.49 (m, 2H), 7.48-7.41 (m, 6H), 7.38 (d, J=2.3 Hz, 1H), 7.36 (d, J=2.1 Hz, 2H), 7.34-7.31 (m, 2H), 7.30-7.25 (m, 2H), 7.21-7.17 (m, 2H), 7.12 (dd, J=8.1, 0.6 Hz, 1H)

Synthesis Example 5: Preparation of Compound H-122

90 mL of o-xylene was added to 5 g of compound 5 (17.16 mmol), 7 g of 1-(3-bromophenyl)dibenzo[b,d]thiophene (20.59 mmol), 0.16 g of CuI (0.858 mmol), 1 g of ethylenediamine (EDA) (17.16 mmol), and 9.1 g of K$_3$PO4 (42.90 mmol) and stirred under reflux for 2 hours. After the reaction was completed, the reaction product was cooled to room temperature, and the resulting solid was filtered under reduced pressure. The filtered solid was dissolved in CHCl$_3$, extracted with MC/Hex, and separated by column chromatography to obtain 2.2 g of compound H-122 (yield: 22%).

$^1$H NMR (DMSO-d$_6$) δ: 8.09 (dd, J=8.0, 1.1 Hz, 1H), 8.04 (ddd, J=8.0, 1.1, 0.7 Hz, 1H), 7.92-7.87 (m, 2H), 7.85-7.82 (m, 1H), 7.80 (ddd, J=8.0, 2.1, 1.2 Hz, 1H), 7.78-7.71 (m, 3H), 7.68-7.63 (m, 2H), 7.60-7.52 (m, 3H), 7.48-7.38 (m, 5H), 7.36-7.24 (m, 4H)

Synthesis Example 6: Preparation of Compound H-16

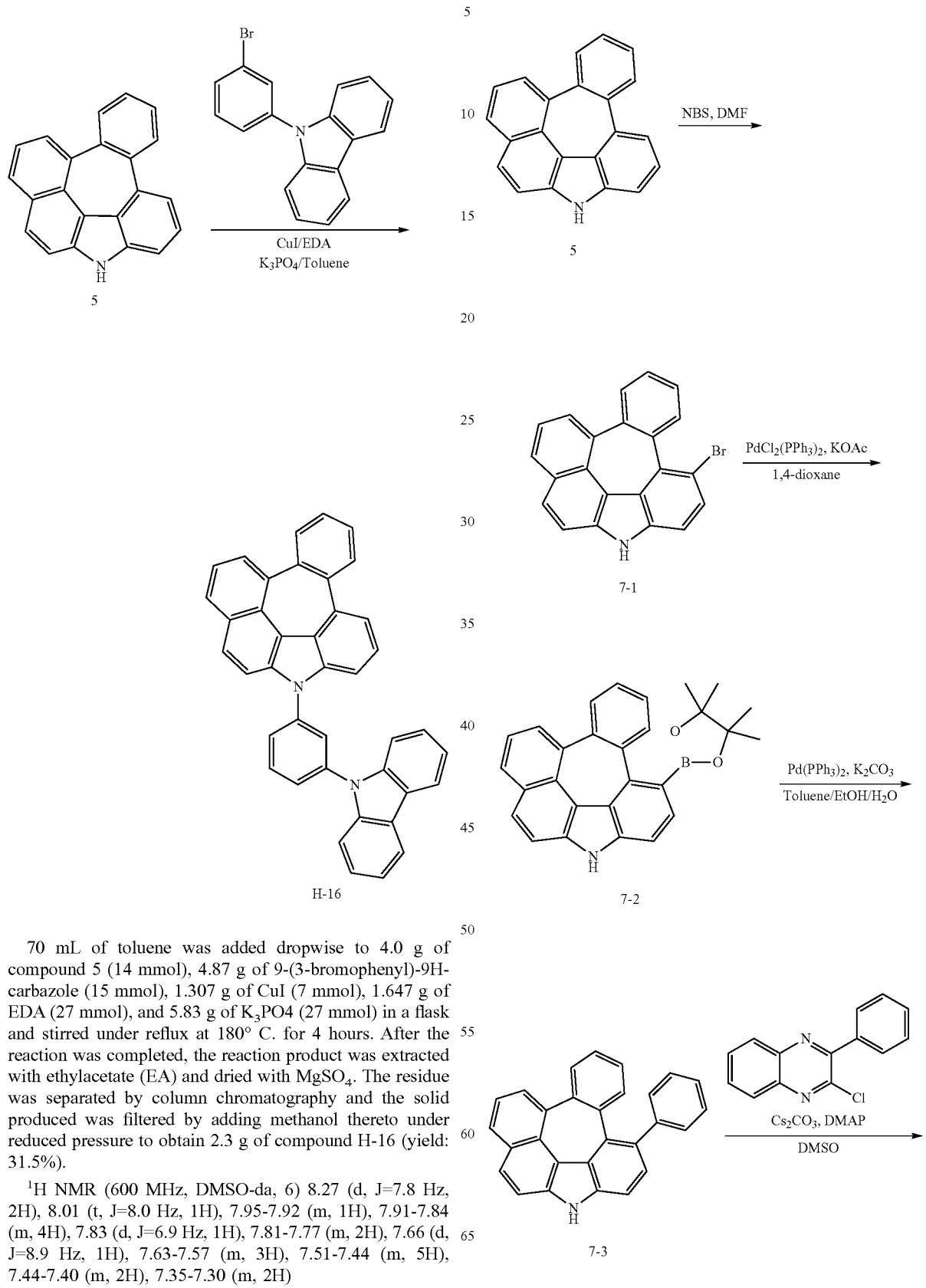

70 mL of toluene was added dropwise to 4.0 g of compound 5 (14 mmol), 4.87 g of 9-(3-bromophenyl)-9H-carbazole (15 mmol), 1.307 g of CuI (7 mmol), 1.647 g of EDA (27 mmol), and 5.83 g of $K_3PO_4$ (27 mmol) in a flask and stirred under reflux at 180° C. for 4 hours. After the reaction was completed, the reaction product was extracted with ethylacetate (EA) and dried with $MgSO_4$. The residue was separated by column chromatography and the solid produced was filtered by adding methanol thereto under reduced pressure to obtain 2.3 g of compound H-16 (yield: 31.5%).

$^1$H NMR (600 MHz, DMSO-d$_6$, δ) 8.27 (d, J=7.8 Hz, 2H), 8.01 (t, J=8.0 Hz, 1H), 7.95-7.92 (m, 1H), 7.91-7.84 (m, 4H), 7.83 (d, J=6.9 Hz, 1H), 7.81-7.77 (m, 2H), 7.66 (d, J=8.9 Hz, 1H), 7.63-7.57 (m, 3H), 7.51-7.44 (m, 5H), 7.44-7.40 (m, 2H), 7.35-7.30 (m, 2H)

Synthesis Example 7: Preparation of Compound H-104

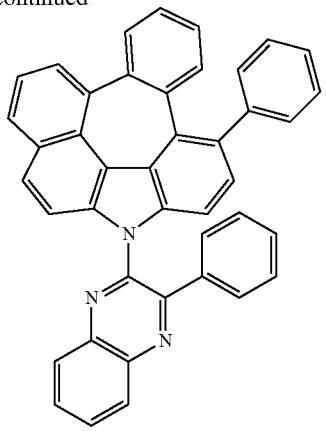

H-104

Synthesis of Compound 7-1

70 g of compound 5 (240 mmol) and 40.6 g of N-bromosuccinimide (255 mmol) were dissolved in 1200 mL of dimethylformamide in a flask, and stirred at 0° C. for 3 hours. After the reaction was completed, an organic layer was extracted with ethyl acetate, and residual moisture was removed by using magnesium sulfate. The residue was dried and separated by column chromatography to obtain 68 g of compound 7-1 (yield: 76%).

Synthesis of Compound 7-2

47.3 g of compound 7-1 (127 mmol), 42 g of bis(pinacolato)diboron (166 mmol), 4.5 g of bis(triphenylphosphine)palladium(II) dichloride (6.4 mmol), and 25 g of potassium acetate (255 mmol) were dissolved in 635 mL of 1,4-dioxane in a flask and refluxed for 4 hours. After the reaction was completed, an organic layer was extracted with ethyl acetate after distillation under reduced pressure, and residual moisture was removed by using magnesium sulfate. The residue was dried and separated by column chromatography to obtain 31.5 g of compound 7-2 (yield: 59%).

Synthesis of Compound 7-3

4.5 g of compound 7-2 (10.7 mmol), 1.9 g of 1-bromobenzene (11.85 mmol), 0.63 g of tetrakis(triphenylphosphine)palladium(0) (0.54 mmol), and 3.7 g of potassium carbonate (26.95 mmol) were dissolved in 54 mL of toluene, 13 mL of ethanol, and 13 mL of water in a flask and refluxed for 12 hours. After the reaction was completed, an organic layer was extracted with ethyl acetate, and residual moisture was removed by using magnesium sulfate. The residue was dried and separated by column chromatography to obtain 2.2 g of compound 7-3 (yield: 56%).

Synthesis of Compound H-104

2.2 g of compound 7-3 (5.9 mmol), 1.58 g of 2-chloro-3-phenylquinoxaline (6.57 mmol), 3.89 g of cesium carbonate (11.96 mmol), and 0.36 g of 4-dimethylaminopyridine (2.99 mmol) were dissolved in 30 mL of dimethyl sulfur monoxide in a flask and stirred at 100° C. for 4 hours. After the reaction was completed, the reaction product was cooled to room temperature, and distilled water was added thereto. An organic layer was extracted with ethyl acetate, and residual moisture was removed by using magnesium sulfate. The residue was dried and separated by column chromatography to obtain 2.9 g of compound H-104 (yield: 85%).

| Compound | MW | M.P. | Tg |
|---|---|---|---|
| H-104 | 571.68 | 210° C. | 167° C. |

Synthesis Example 8: Preparation of Compound H-11

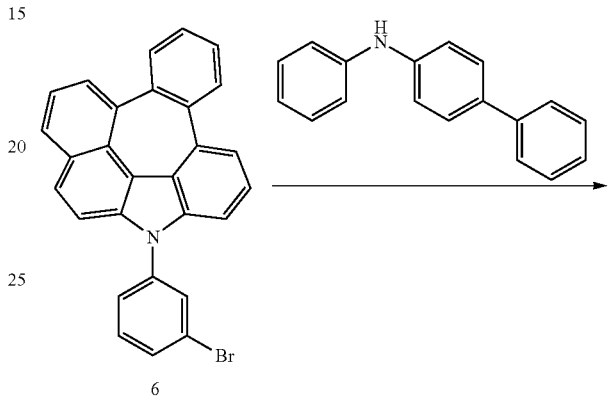

6

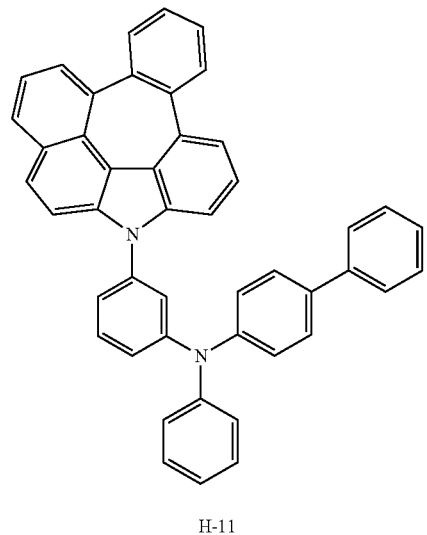

H-11

60 mL of toluene was added to 5.0 g of compound 6 (11.2 mmol), 3.0 g of N-phenyl-[1,1'-biphenyl]-4-amine (12.3 mmol), 0.5 g of $Pd_2(dba)_3$ (0.56 mmol), 0.46 g of s-phos (1.12 mmol), and 2.7 g of NaOtBu (28 mmol) in a flask and stirred under reflux for 6 hours. After the reaction was completed, the reaction mixture was cooled to room temperature and stirred at room temperature. A solid produced by adding MeOH thereto was filtered under reduced pressure, and separated by column chromatography using MC/Hex to obtain 2.3 g of compound H-11 (yield: 34%).

| Compound | MW | M.P. |
|---|---|---|
| H-11 | 610.8 | 132° C. |

Synthesis Example 9: Preparation of Compound H-120

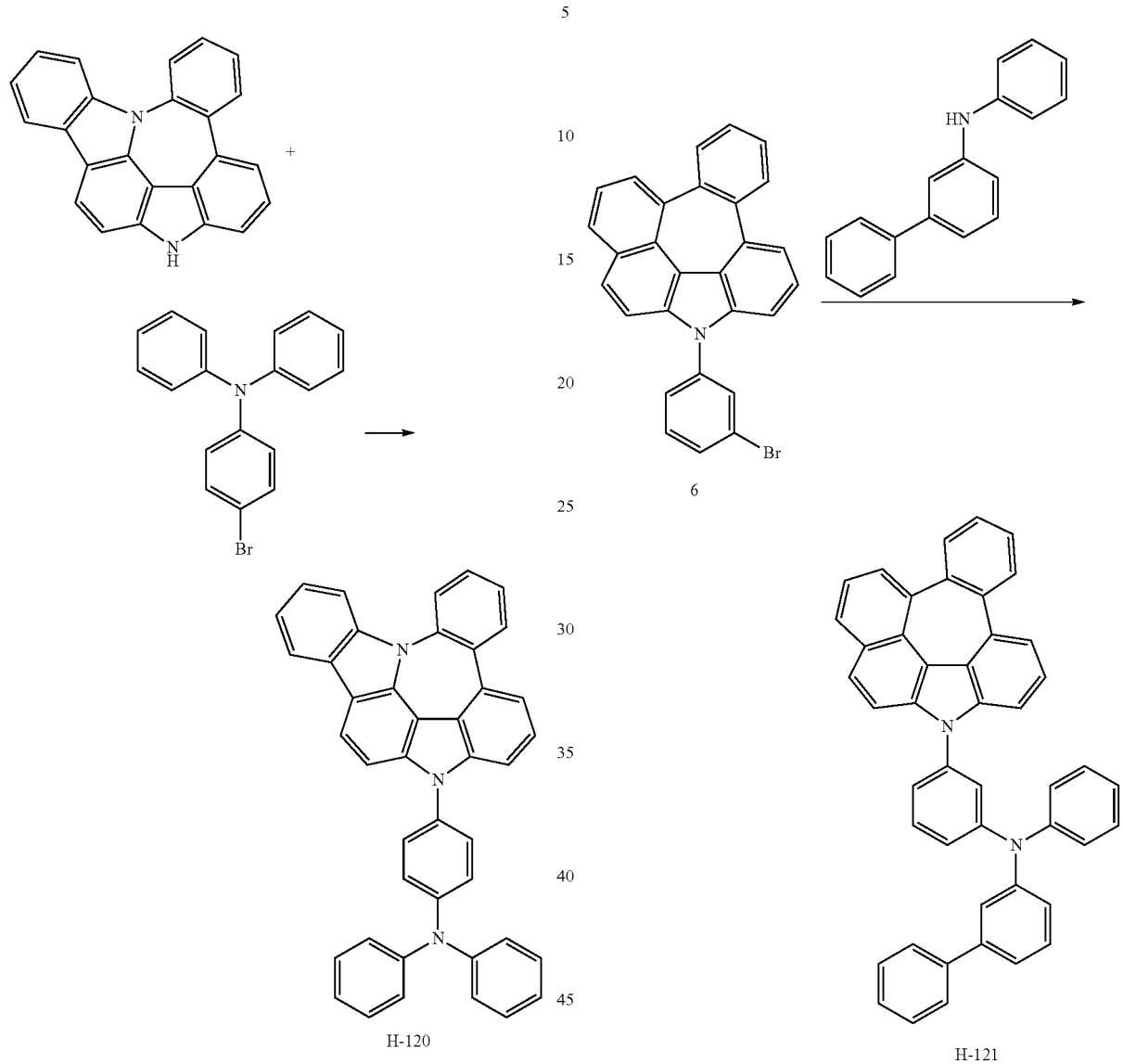

80 mL of o-xylene was added to 5.0 g of 14H-7b,14-diazadibenzo[3,4:5,6]azuleno[7,8,1-lma]fluorene (11.2 mmol), 5.4 g of 4-bromo-N,N-diphenylaniline (16.7 mmol), 0.7 g of Pd$_2$(dba)$_3$ (0.76 mmol), 0.6 g of s-phos (1.52 mmol), and 2.9 g of NaOtBu (30.4 mmol) in a flask and stirred under reflux for 4 hours. After the reaction was completed, the reaction mixture was cooled to room temperature and stirred at room temperature. A solid produced by adding MeOH thereto was filtered under reduced pressure, and separated by column chromatography using MC/Hex to obtain 4.0 g of compound H-120 (yield: 46%).

| Compound | MW | M.P. |
|---|---|---|
| H-120 | 573.7 | 317° C. |

Synthesis Example 10: Preparation of Compound H-121

160 mL of toluene was added to 14.0 g of compound 6 (31.4 mmol), 7.78 g of N-phenyl-[1,1'-biphenyl]-3-amine (31.7 mmol), 1.44 g of Pd$_2$dba$_3$ (1.57 mmol), 635 mg of t-Bu$_3$P (3.14 mmol), and 6.04 g of t-BuONa (62.8 mmol) in a flask and stirred under reflux for 2 hours. After the reaction was completed, the mixture was cooled to room temperature and extracted with distilled water and EA. The organic layer was filtered under reduced pressure, and separated by column chromatography using MC/Hex to obtain 14.6 g of compound H-121 (yield: 76%).

| Compound | MW | M.P. |
|---|---|---|
| H-121 | 610.7 | 141° C. |

Synthesis Example 11: Preparation of Compound H-119

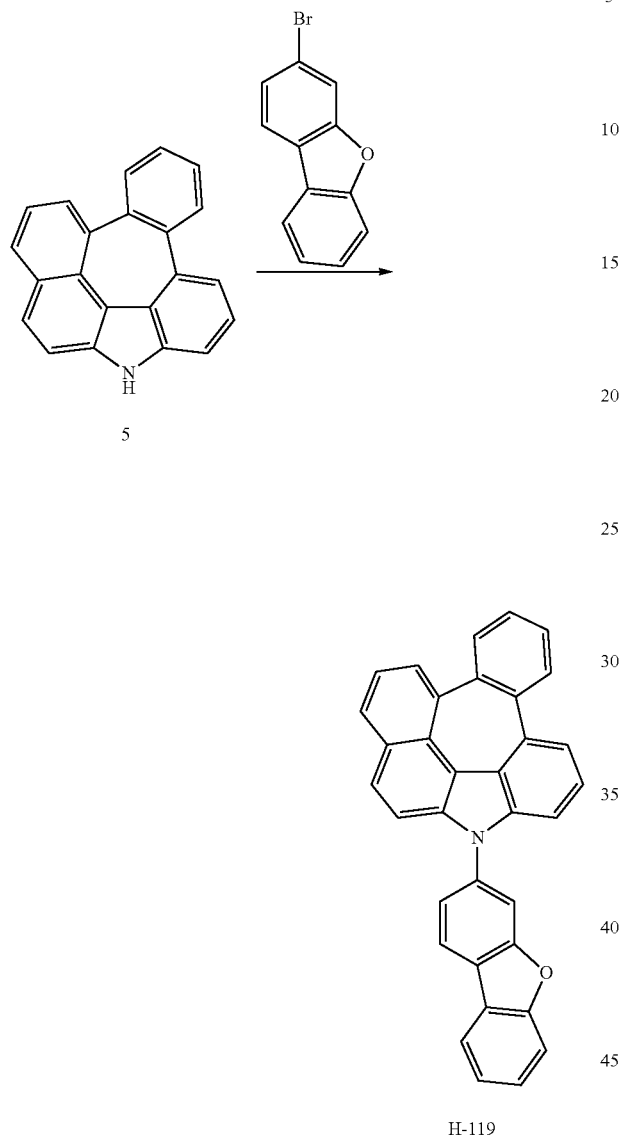

170 mL of toluene was added to 10 g of compound 5 (34.3 mmol), 12.7 g of 3-bromodibenzo[b,d]furan (51.45 mmol), 3.3 g of CuI (17.15 mmol), 4.6 mL of ethylenediamine (EDA) (68.8 mmol), and 21.8 g of K$_3$PO4 (102.9 mmol) in a flask and stirred under reflux for 12 hours. After the reaction was completed, the reaction mixture was cooled to room temperature and stirred at room temperature. A solid produced by adding MeOH thereto was filtered under reduced pressure, and separated by column chromatography using MC/Hex to obtain 8.3 g of compound H-119 (yield: 53%).

| Compound | MW | M.P. |
| --- | --- | --- |
| H-119 | 457.53 | 255.4° C. |

Synthesis Example 12: Preparation of Compound H-12

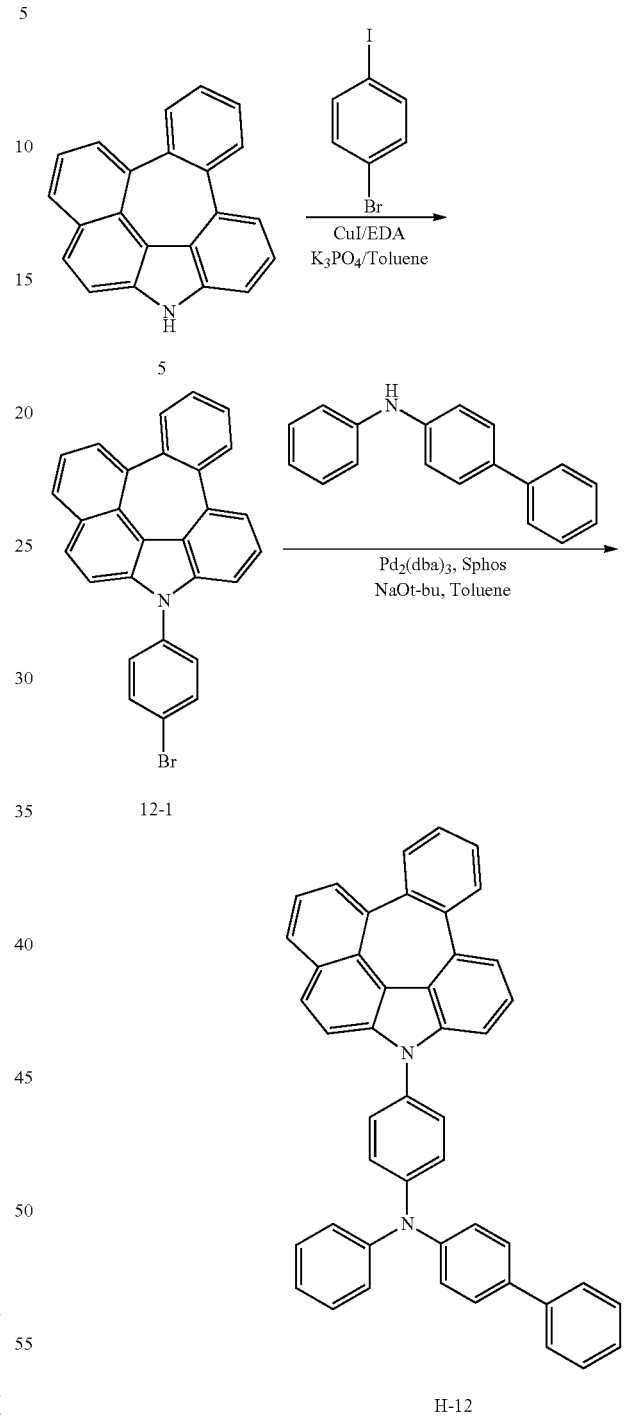

Synthesis of Compound 12-1

10.0 g of 3H-3-azadibenzo[g,ij]naphtho[2,1,8-cde]azulene (34.3 mmol), 14.6 g of 1-bromo-4-iodobenzene (51.5 mmol), 3.28 g of CuI (17.2 mmol), 4.12 g of EDA (68.6 mmol), 14.6 g of K$_3$PO4 (68.6 mmol), and 170 mL of toluene were introduced into a flask and stirred under reflux at 145° C. for 3 hours. After the reaction was completed, the reaction product was extracted with MC and dried with MgSO$_4$. The residue was separated by column chromatography and the solid produced was filtered by adding MeOH thereto under reduced pressure to obtain 9.0 g of compound 12-1 (yield: 59%).

Synthesis of Compound H-12

5.0 g of compound 12-1 (11 mmol), 3.3 g of N-phenyl-[1,1'-biphenyl]-4-amine (13 mmol), 0.513 g of Pd$_2$(dba)$_3$ (0.56 mmol), 0.460 g of s-phos (1 mmol), 2.691 g of NaOt-Bu (28 mmol), and 60 mL of toluene were introduced into a flask and stirred under reflux at 100° C. for 0.5 hours. After the reaction was completed, the reaction product was extracted with MC and dried with MgSO$_4$. The residue was separated by column chromatography and filtered the solid produced by adding MeOH thereto under reduced pressure to obtain 1.3 g of compound H-12 (yield: 19%).

| Compound | MW | M.P. |
| --- | --- | --- |
| H-12 | 610.76 | 168° C. |

Synthesis Example 13: Preparation of Compound H-35

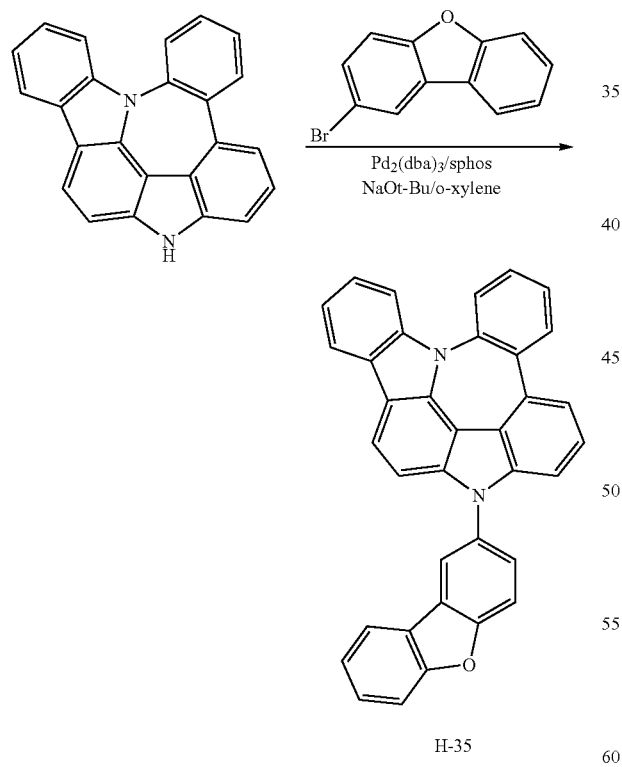

75 mL of o-xylene was added to 5.0 g of 14H-7b,14-diazadibenzo[3,4:5,6]azuleno[7,8,1-lma]fluorene (15.1 mmol), 4.1 g of 2-bromodibenzo[b,d]furan (16.6 mmol), 0.691 g of Pd$_2$(dba)$_3$ (0.755 mmol), 0.620 g of s-phos (1.51 mmol), and 3.63 g of NaOtBu (37.8 mmol) in a flask and stirred under reflux for 6 hours. After the reaction was completed, the reaction mixture was cooled to room temperature and stirred at room temperature. A solid produced by adding MeOH thereto was filtered under reduced pressure, and separated by column chromatography using MC/Hex to obtain 1.9 g of compound H-35 (yield: 25%).

| Compound | MW | M.P. |
| --- | --- | --- |
| H-35 | 496.56 | 280° C. |

Synthesis Example 14: Preparation of Compound E-112

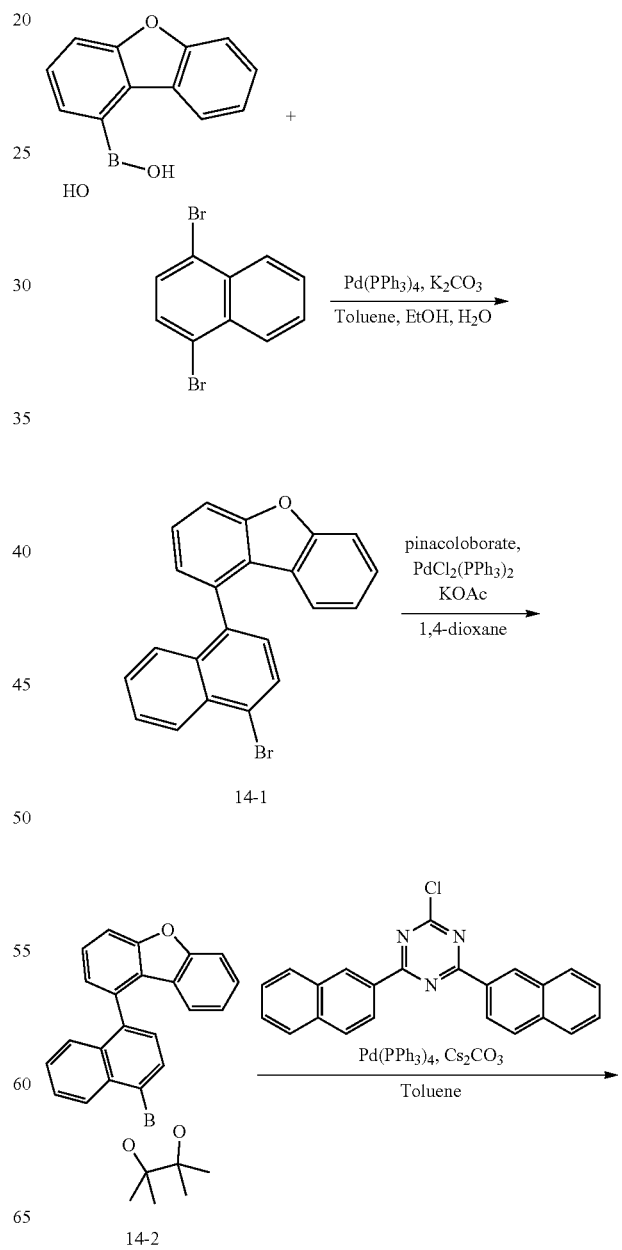

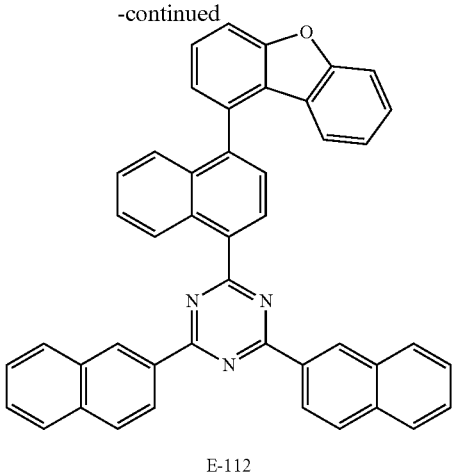

E-112

Synthesis of Compound 14-1

20 g of dibenzo[b,d]furan-1-yl boronic acid (94.3 mmol), 53.9 g of 1,4-dibromonaphthalene (188.67 mmol), 32.6 g of K$_2$CO$_3$ (235.75 mmol), and 5.4 g of Pd(PPh$_3$)$_4$ (4.7 mmol) were dissolved in 470 mL of toluene, 235 mL of ethanol, and 235 mL of water in a flask, and refluxed at 140° C. for 4 hours. After the reaction was completed, an organic layer was extracted with ethyl acetate, and residual moisture was removed by using magnesium sulfate. The residue was dried and separated by column chromatography to obtain 20 g of compound 14-1 (yield: 56.8%).

Synthesis of compound 14-2

20 g of compound 14-1 (53.6 mmol), 16.3 g of 4,4,4',4',5,5,5'5'-octamethyl-2,2'-bi(1,3,2-dioxaborolane) (64.3 mmol), 3.76 g of PdCl$_2$(PPh$_3$)$_2$ (5.36 mmol), and 10.5 g of KOAc (107.2 mmol) were dissolved in 270 mL of 1,4-dioxane in a flask, and refluxed at 150° C. for 4 hours. After the reaction was completed, an organic layer was extracted with ethyl acetate, and residual moisture was removed by using magnesium sulfate. The residue was dried and separated by column chromatography to obtain 23 g of compound 14-2 (yield: 100%).

Synthesis of Compound E-112

7 g of compound 14-2 (16.6 mmol), 7.35 g of 2-chloro-4,6-di(naphthalen-2-yl)-1,3,5-triazine (19.9 mmol), 13.5 g of Cs$_2$CO$_3$ (41.5 mmol), and 959 mg of Pd(PPh$_3$)$_4$ (0.83 mmol) were dissolved in 83 mL of toluene in a flask, and refluxed at 130° C. for 18 hours. After the reaction was completed, an organic layer was extracted with ethyl acetate, and residual moisture was removed by using magnesium sulfate. The residue was dried and separated by column chromatography to obtain 2 g of compound E-112 (yield: 19.2%).

Synthesis Example 15: Preparation of Compound E-117

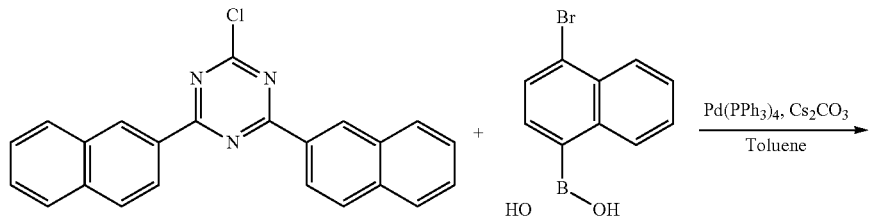

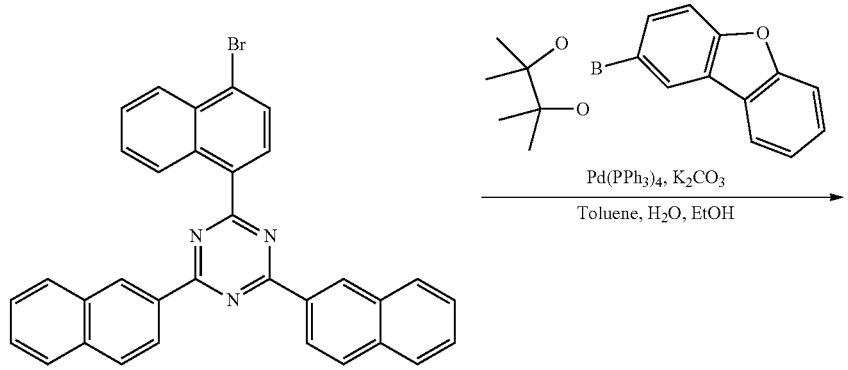

15-1

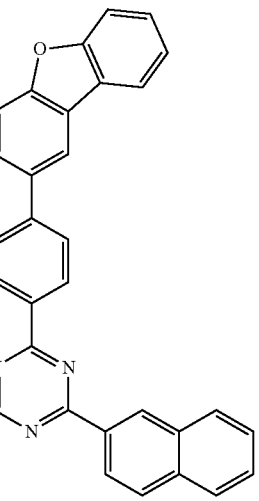

E-117

Synthesis of Compound 15-1

32.2 g of 2-chloro-4,6-di(naphthalen-2-yl)-1,3,5-triazine (87.7 mmol), 20 g of (4-bromonaphthalen-1-yl)boronic acid (79.7 mmol), 65 g of $Cs_2CO_3$ (199.25 mmol), and 4.6 g of $Pd(PPh)_4$ (3.985 mmol) were dissolved in 400 mL of toluene in a flask, and refluxed at 140° C. for 4 hours. After the reaction was completed, an organic layer was extracted with ethyl acetate, and residual moisture was removed by using magnesium sulfate. The residue was dried and separated by column chromatography to obtain 20 g of compound 15-1 (yield: 46.6%).

Synthesis of compound E-117

7 g of compound 15-1 (13 mmol), 4.6 g of 2-(dibenzo[b,d]furan-2-yl)-4,4,5,5-tetramethyl-1,3,2-dioxaborolane (15.6 mmol), 4.5 g of $K_2CO_3$ (32.5 mmol), and 0.75 g of $Pd(PPh_3)_4$ (0.65 mmol) were dissolved in 65 mL of toluene, 32.5 mL of ethanol, and 32.5 mL of water in a flask, and refluxed at 130° C. for 3 hours. After the reaction was completed, an organic layer was extracted with ethyl acetate, and residual moisture was removed by using magnesium sulfate. The residue was dried and separated by column chromatography to obtain 3.4 g of compound E-117 (yield: 41%).

Synthesis Example 16: Preparation of Compound E-130

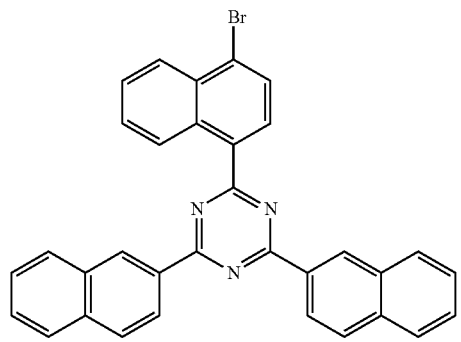

15-1

+

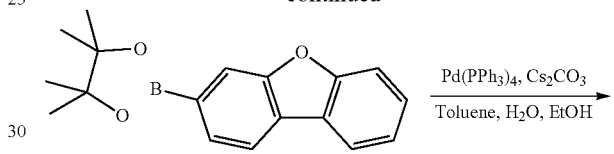

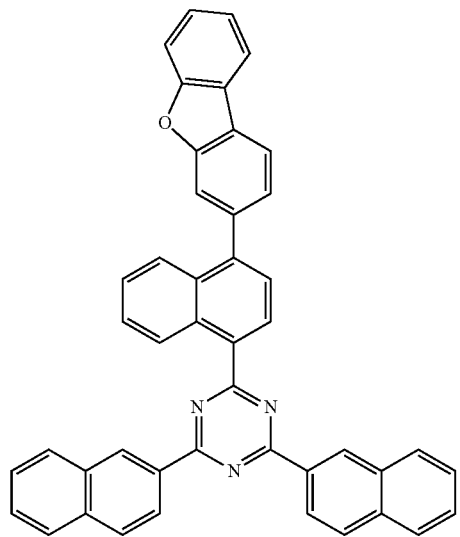

E-130

4.4 g of compound 15-1 (12.3 mmol), 5 g of 2-(dibenzo[b,d]furan-3-yl)-4,4,5,5-tetramethyl-1,3,2-dioxaborolane (13.5 mmol), 4.5 g of $Cs_2CO_3$ (32.5 mmol), and 0.75 g of $Pd(PPh)_4$ (0.65 mmol) were dissolved in 60 mL of toluene, 30 mL of ethanol, and 30 mL of water in a flask, and refluxed at 130° C. for 3 hours. After the reaction was completed, an organic layer was extracted with ethyl acetate, and residual moisture was removed by using magnesium sulfate. The residue was dried and separated by column chromatography to obtain 4 g of compound E-130 (yield: 49%).

Synthesis Example 17: Preparation of Compound E-111

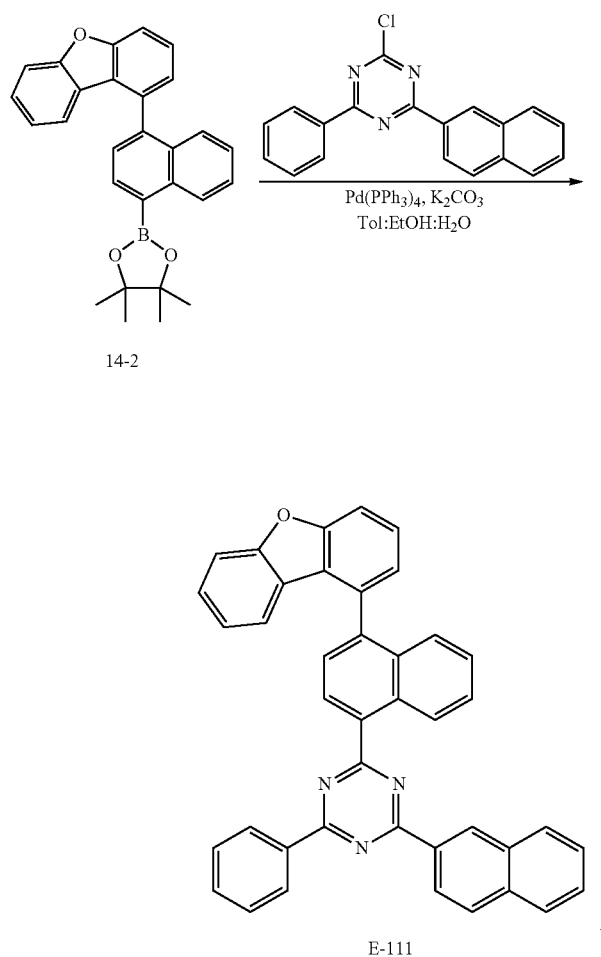

64 mL of toluene, 16 mL of EtOH, and 16 mL of purified water were added to 6 g of compound 14-2 (14.16 mmol), 5 g of 2-chloro-4-(naphthalen-2-yl)-6-phenyl-1,3,5-triazine (15.73 mmol), 0.9 g of Pd(PPh$_3$)$_4$ (0.786 mmol), and 4.3 g of K$_2$CO$_3$ (31.47 mmol) in a flask and stirred under reflux for 2 hours. After the reaction was completed, the mixture was cooled to room temperature and extracted with distilled water and EA. The organic layer was filtered under reduced pressure, and separated by column chromatography using MC/Hex to obtain 4 g of compound E-111 (yield: 44%).

$^1$H NMR (DMSO-d$_6$) δ: 9.42 (d, J=1.3 Hz, 1H), 9.29-9.24 (m, 1H), 8.83 (td, J=8.6, 1.5 Hz, 3H), 8.72 (d, J=7.3 Hz, 1H), 8.30 (d, J=8.0 Hz, 1H), 8.22 (d, J=8.7 Hz, 1H), 8.12-8.07 (m, 1H), 7.92 (dd, J=8.3, 0.8 Hz, 1H), 7.89 (d, J=7.3 Hz, 1H), 7.81-7.72 (m 6H), 7.72-7.65 (m, 2H), 7.65-7.60 (m, 1H), 7.54-7.41 (m, 3H), 7.04 (ddd, J=8.1, 7.3, 0.9 Hz, 1H), 6.53 (dt, J=8.0, 0.9 Hz, 1H)

| Compound | MW | M.P. |
|---|---|---|
| E-111 | 575.6 | 131.3° C. |

Synthesis Example 18: Preparation of Compound E-90

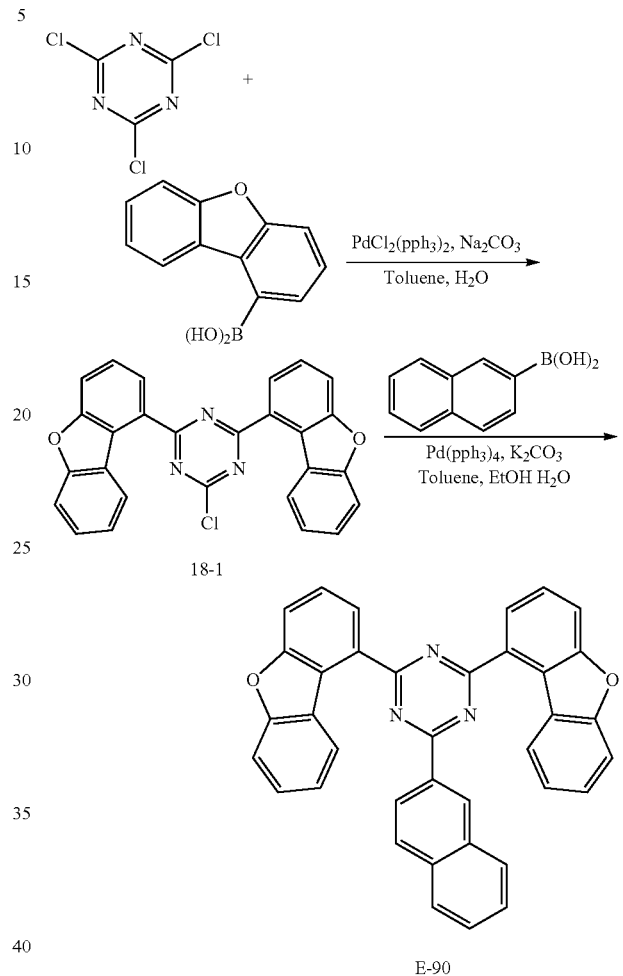

Synthesis of Compound 18-1

150 mL of toluene and 30 mL of purified water were added to 10 g of 2,4,6-trichloro-1,3,5-triazine (54.22 mmol), 20.7 g of dibenzo[b,d]furan-1-yl boronic acid (97.60 mmol), 0.76 g of PdCl$_2$(PPh$_3$)$_2$ (1.084 mmol), and 5.7 g of Na$_2$CO$_3$ (54.22 mmol) in a flask and stirred for 2 days. After the reaction was completed, the mixture was cooled to room temperature and extracted with distilled water and MeOH to obtain 3.4 g of compound 18-1 (yield: 14%).

Synthesis of Compound E-90

32 mL of toluene, 8 mL of EtOH, and 8 mL of purified water were added to 3.4 g of compound 18-1 (7.592 mmol), 1.5 g of naphthalen-2-yl boronic acid (9.111 mmol), 0.4 g of Pd(PPh)$_4$ (0.379 mmol), and 2 g of K$_2$CO$_3$ (15.18 mmol) in a flask and stirred under reflux at 140° C. for 1 hour. After the reaction was completed, the mixture was condensed under reduced pressure and extracted with MC, and the organic layer was condensed. The condensed organic layer was separated by column chromatography using MC/Hex to obtain 0.88 g of compound E-90 (yield: 21%).

¹H NMR (DMSO-d₆) δ: 9.35 (d, J=1.6 Hz, 1H), 8.74 (dd, J=8.6, 1.7 Hz, 1H), 8.71 (dd, J=7.7, 1.2 Hz, 2H), 8.51 (dd, J=7.7, 1.0 Hz, 2H), 8.20 (d, J=8.7 Hz, 1H), 8.13-8.07 (m, 4H), 7.86-7.80 (m, 4H), 7.75-7.70 (m, 1H), 7.66 (dd, J=8.5, 7.0 Hz, 1H), 7.59 (ddd, J=8.4, 7.2, 1.3 Hz, 2H), 7.18 (ddd, J=8.1, 7.1, 1.0 Hz, 2H)

| Compound | MW | M.P. |
| --- | --- | --- |
| E-90 | 539.5 | 282.1° C. |

Synthesis Example 19: Preparation of Compound E-125

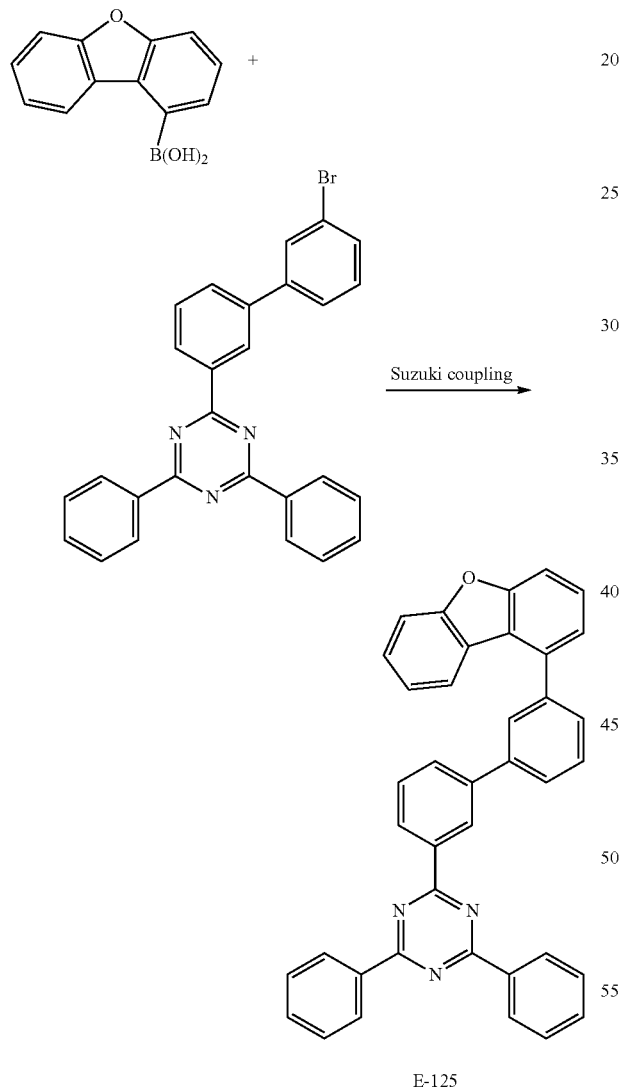

E-125

3.0 g of dibenzo[b,d]furan-1-yl boronic acid (14.2 mmol), 7.3 g of 2-(3'-bromo-[1,1'-biphenyl]-3-yl)-4,6-diphenyl-1,3,5-triazine (15.6 mmol), 0.8 g of tetrakis(triphenylphosphine) palladium(0) (0.71 mmol), and 3.9 g of sodium carbonate (28.4 mmol) were dissolved in 30 mL of toluene, 8 mL of ethanol, and 15 mL of water in a flask and refluxed for 2 hours. After the reaction was completed, an organic layer was extracted with ethyl acetate, and residual moisture was removed by using magnesium sulfate. The residue was dried and separated by column chromatography to obtain 2.7 g of compound E-125 (yield: 35%).

| Compound | MW | M.P. |
| --- | --- | --- |
| E-125 | 551.6 | 233° C. |

Synthesis Example 20: Preparation of Compound E-106

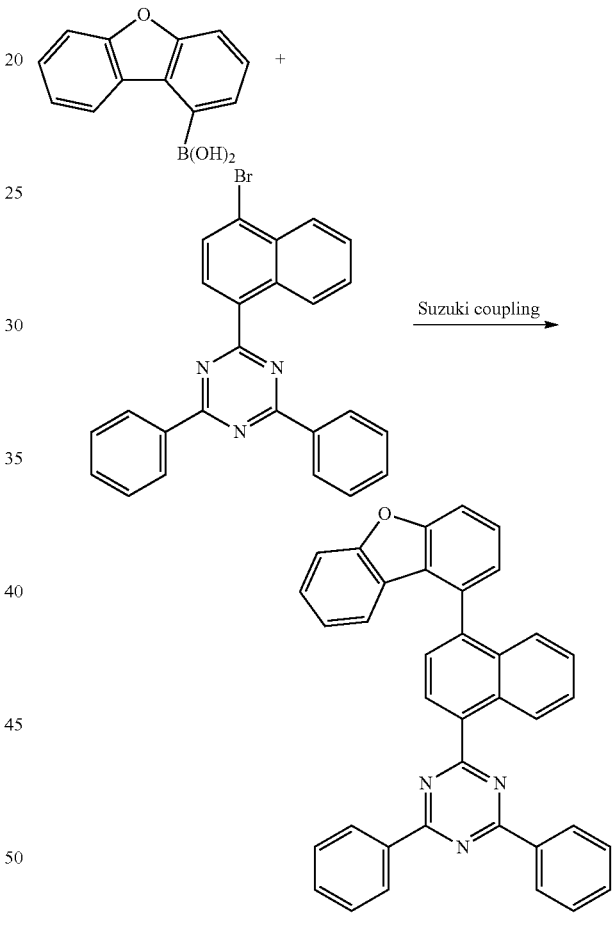

E-106

3.0 g of dibenzo[b,d]furan-1-yl boronic acid (14.2 mmol), 6.3 g of 2-(4-bromonaphthalen-1-yl)-4,6-diphenyl-1,3,5-triazine (14.2 mmol), 0.82 g of tetrakis(triphenylphosphine) palladium(0) (0.71 mmol), and 3.9 g of sodium carbonate (28.4 mmol) were dissolved in 30 mL of toluene, 8 mL of ethanol, and 15 mL of water in a flask and refluxed for 2 hours. After the reaction was completed, an organic layer was extracted with ethyl acetate, and residual moisture was removed by using magnesium sulfate. The residue was dried and separated by column chromatography to obtain 1.9 g of compound E-106 (yield: 26%).

| Compound | MW | M.P. |
|---|---|---|
| E-106 | 525.6 | 203° C. |

Synthesis Example 21: Preparation of Compound E-91

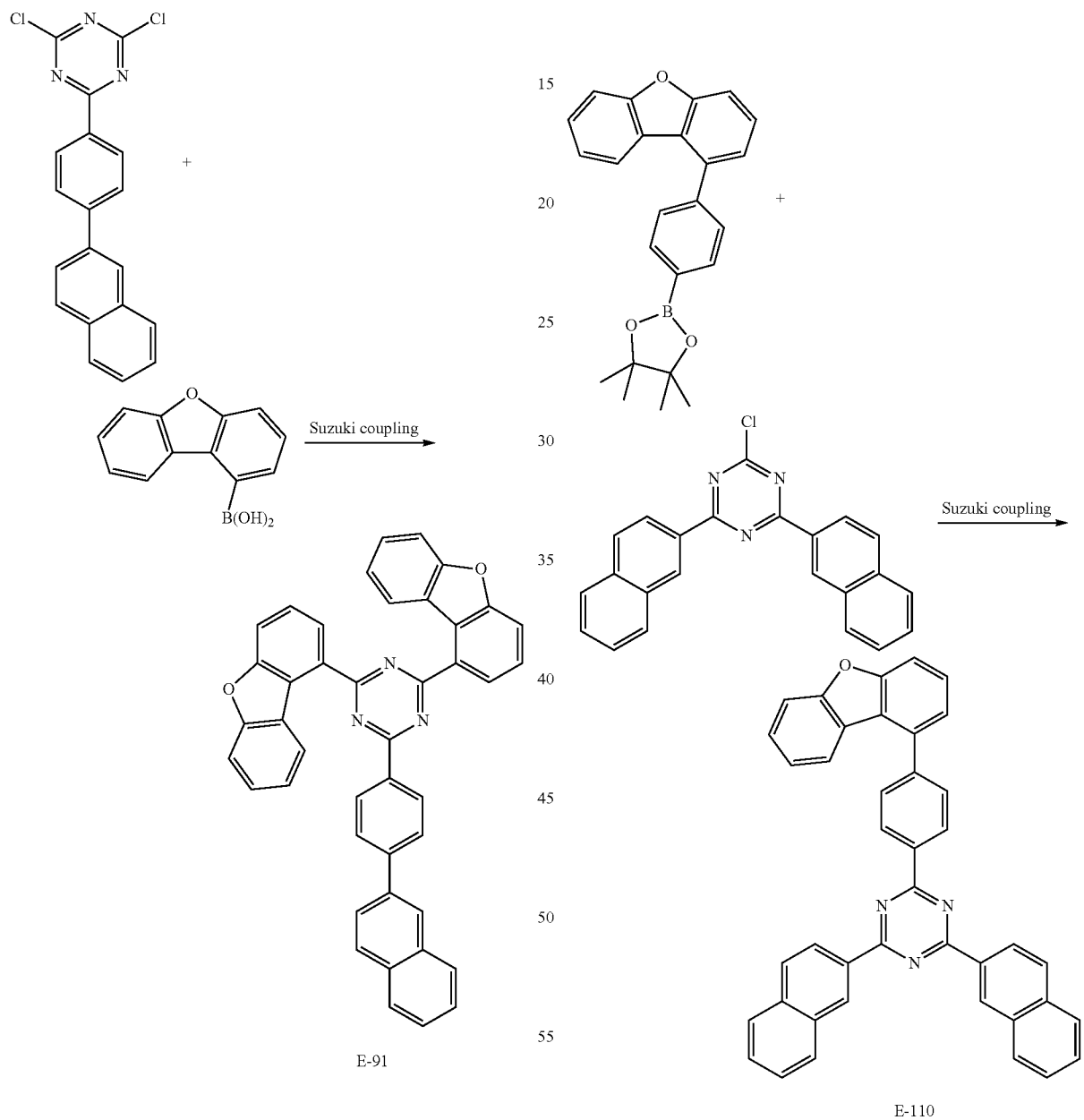

and separated by column chromatography to obtain 1.0 g of compound E-91 (yield: 36%).

| Compound | MW | M.P. |
|---|---|---|
| E-91 | 615.7 | 304° C. |

Synthesis Example 22: Preparation of Compound E-110

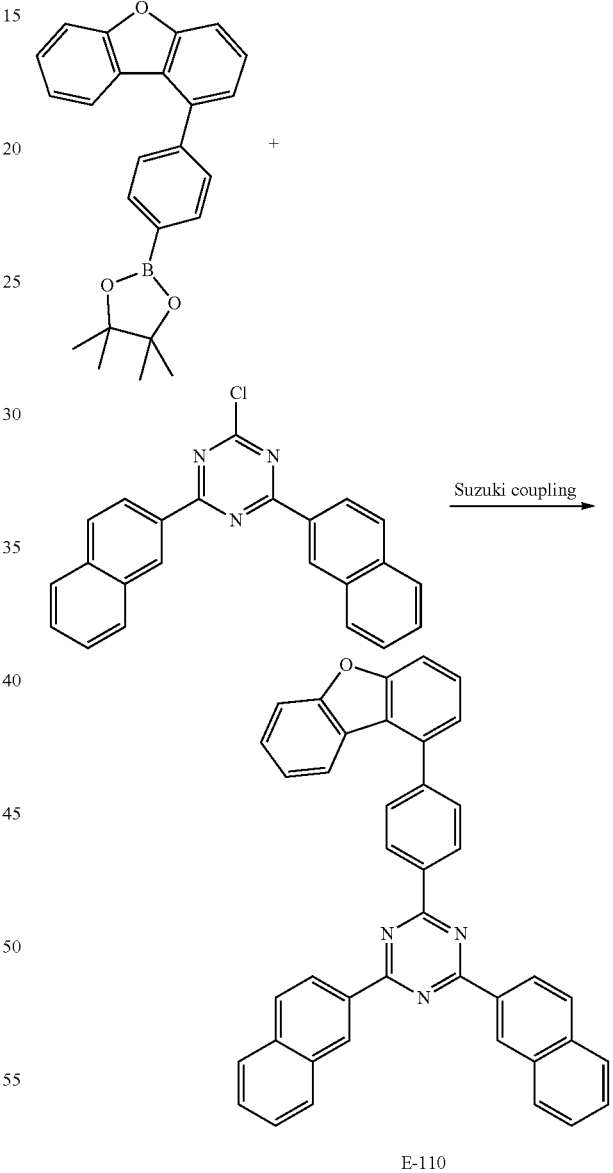

1.6 g of 2,4-dichloro-6-(4-(naphthalen-2-yl)phenyl)-1,3,5-triazine (4.54 mmol), 2.12 g of dibenzo[b,d]furan-1-yl boronic acid (10 mmol), 0.26 g of tetrakis(triphenylphosphine)palladium(0) (0.23 mmol), and 1.3 g of sodium carbonate (9.0 mmol) were dissolved in 16 mL of toluene, 1 mL of ethanol, and 1 mL of water in a flask and refluxed for 3 hours. After the reaction was completed, an organic layer was extracted with ethyl acetate, and residual moisture was removed by using magnesium sulfate. The residue was dried 4.0 g of 2-(4-(dibenzo[b,d]furan-1-yl)phenyl)-4,4,5,5-tetramethyl-1,3,2-dioxaborolane (10.8 mmol), 4.4 g of 2-chloro-4,6-di(naphthalen-2-yl)-1,3,5-triazine (11.9 mmol), 0.6 g of tetrakis(triphenylphosphine)palladium(0) (0.54 mmol), and 3.0 g of sodium carbonate (21.6 mmol) were dissolved in 30 mL of toluene, 7 mL of ethanol, and 10 mL of water in a flask and refluxed for 7 hours. After the reaction was completed, an organic layer was extracted with ethyl acetate, and residual moisture was removed by using magnesium sulfate. The residue was dried and separated by column chromatography to obtain 4.0 g of compound E-110 (yield: 65%).

| Compound | MW | M.P. |
|---|---|---|
| E-110 | 575.2 | 261° C. |

Device Examples 1 to 10: Production of an OLED Comprising the Plurality of Host Materials According to the Present Disclosure An organic electroluminescent device (OLED) according to the present disclosure was produced comprising the plurality of host materials according to the present disclosure. A transparent electrode indium tin oxide (ITO) thin film (10 Ω/sq) on a glass substrate for an OLED (Geomatec, Japan) was subjected to an ultrasonic washing with trichloroethylene, acetone, ethanol, and distilled water, sequentially, and was then stored in isopropanol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-8}$ torr. Thereafter, an electric current was applied to the cell to evaporate the above-introduced material, thereby forming a first hole injection layer having a thickness of 80 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. Compound HT-2 was introduced into another cell of said vacuum vapor depositing apparatus, and was evaporated by applying an electric current to the cell, thereby forming a second hole transport layer having a thickness of 60 nm on the first hole transport layer. After forming the hole injection layers and the hole transport layers, a light-emitting layer was then deposited as follows. The first and second host compounds shown in Table 1 below were introduced into two cells of the vacuum vapor depositing apparatus as a host, and compound D-39 was introduced into another cell. The two host materials were evaporated at a rate of 1:1 and the dopant material was simultaneously evaporated at a different rate and these were deposited in a doping amount of 3 wt % based on the total amount of the host and dopant to form a light-emitting layer having a thickness of 40 nm on the second hole transport layer. Compound ET-1 and compound EI-1 were then introduced into two other cells, evaporated at the rate of 1:1, and deposited to form an electron transport layer having a thickness of 35 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED was produced.

Comparative Examples 1 and 2: Production of an OLED not According to the Present Disclosure An OLED was produced in the same manner as in Device Example 1, except that only one compound, i.e., the first host compound as listed in Table 1 below, was used instead of two hosts.

The luminous efficiency at a luminance of 1,000 nit, and the time taken for luminance to decrease from 100% to 95% at a constant current in a luminance of 5,000 nit (lifespan: T95) of the OLED devices produced in the Device Examples and Comparative Examples are provided in Table 1 below.

TABLE 1

|  | First Host | Second Host | Luminous Efficiency (cd/A) | Lifespan (T95, hr) |
|---|---|---|---|---|
| Device Example 1 | E-111 | H-7 | 28.9 | 168 |
| Device Example 2 | E-92 | H-7 | 29.0 | 403 |
| Device Example 3 | E-111 | H-31 | 29.0 | 801 |
| Device Example 4 | E-111 | H-14 | 31.8 | 442 |
| Device Example 5 | E-112 | H-11 | 31.1 | 305 |
| Device Example 6 | E-112 | H-12 | 30.7 | 389 |
| Device Example 7 | E-115 | H-7 | 32.9 | 375 |
| Device Example 8 | E-115 | H-120 | 32.8 | 347 |
| Device Example 9 | E-136 | H-7 | 33.6 | 404 |
| Device Example 10 | E-136 | H-120 | 33.3 | 480 |
| Comparative Example 1 | E-111 | — | 25.0 | 21 |
| Comparative Example 2 | E-92 | — | 26.6 | 54 |

From Table 1, it is confirmed that an organic electroluminescent device comprising the plurality of host materials comprising a specific combination of compounds according to the present disclosure has improved efficiency and/or lifespan characteristics compared to conventional organic electroluminescent devices.

The compounds used in the Device Examples and the Comparative Examples are shown in Table 2 below.

TABLE 2
Hole Injection Layer/Hole Transport Layer
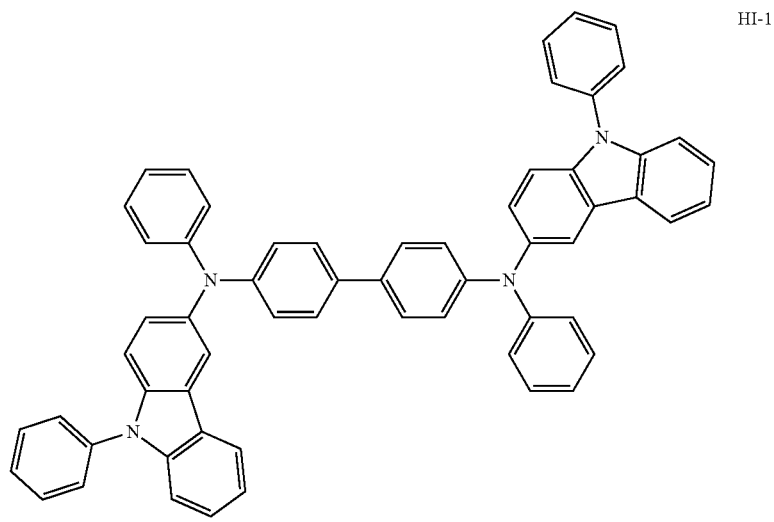
HI-1
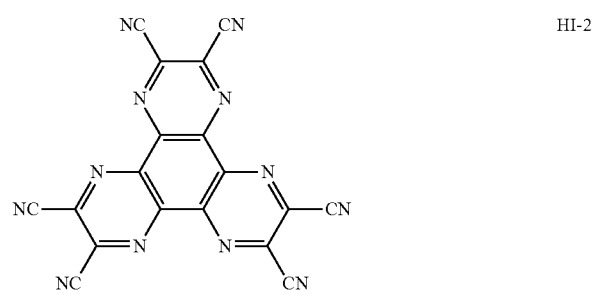
HI-2
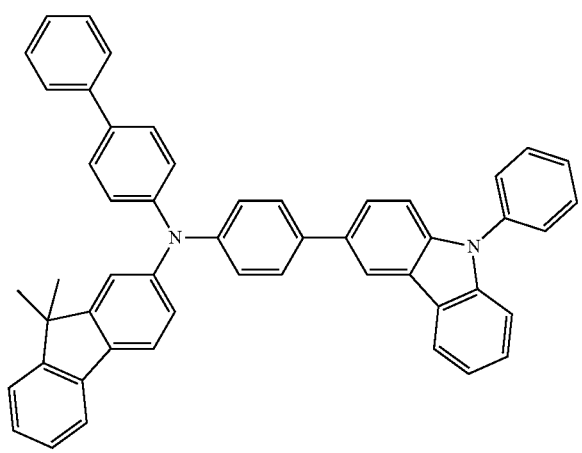 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
HT-1

167
TABLE 2-continued
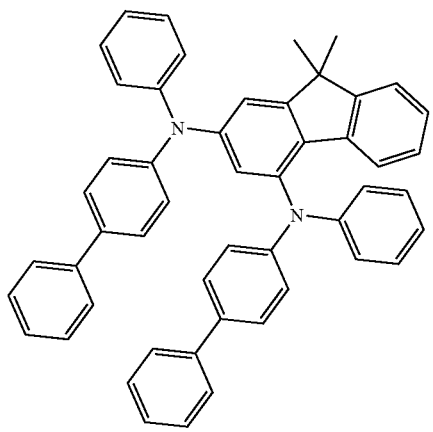 [SMILES: CC1(C)c2ccccc2-c2c(N(c3ccccc3)c3ccc(-c4ccccc4)cc3)cc(N(c3ccccc3)c3ccc(-c4ccccc4)cc3)cc21]
HT-2
Light-Emitting Layer
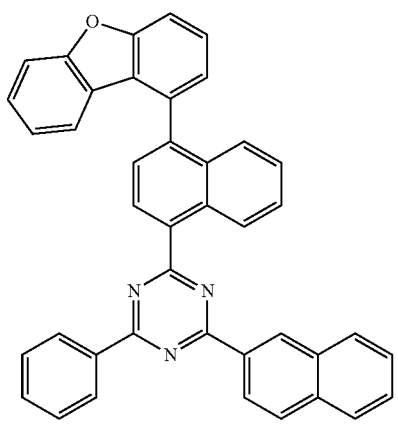 [SMILES: c1ccc(-c2nc(-c3ccc4ccccc4c3)nc(-c3ccc(-c4cccc5oc6ccccc6c45)c4ccccc34)n2)cc1]
E-111
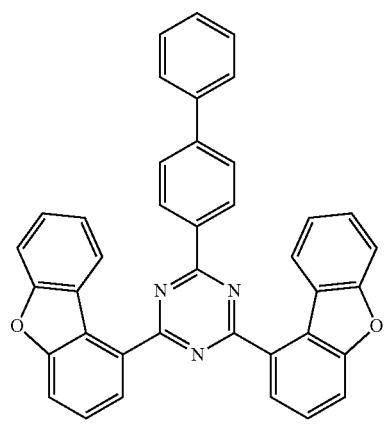 [SMILES: c1ccc(-c2ccc(-c3nc(-c4cccc5oc6ccccc6c45)nc(-c4cccc5oc6ccccc6c45)n3)cc2)cc1]
E-92

TABLE 2-continued
H-7
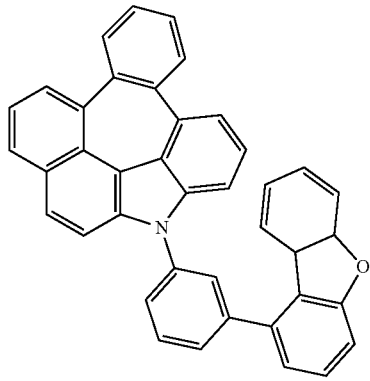 [SMILES: C1=CC2Oc3cccc(-c4cccc(-n5c6cccc7c6c6c8c(cccc8ccc65)-c5ccccc5-7)c4)c3C2C=C1]
H-14
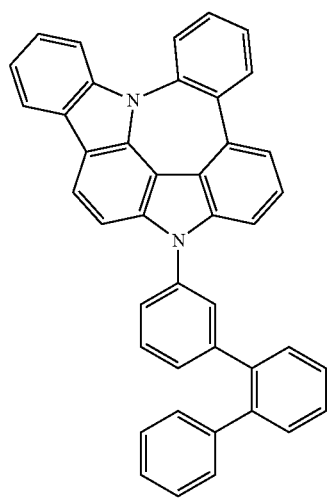 [SMILES: c1ccc(-c2ccccc2-c2cccc(-n3c4cccc5c6ccccc6n6c7ccccc7c7ccc3c(c54)c76)c2)cc1]
H-11
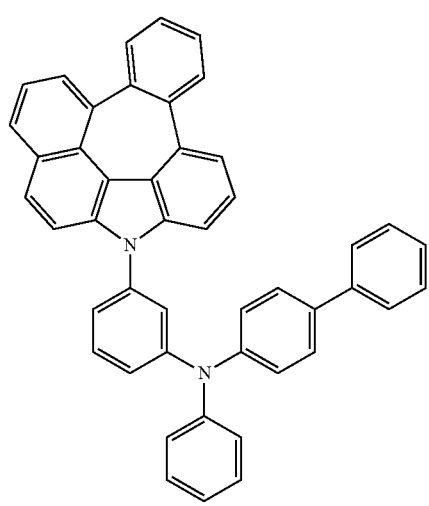 [SMILES: c1ccc(-c2ccc(N(c3ccccc3)c3cccc(-n4c5cccc6c5c5c7c(cccc7ccc54)-c4ccccc4-6)c3)cc2)cc1]

TABLE 2-continued
H-12
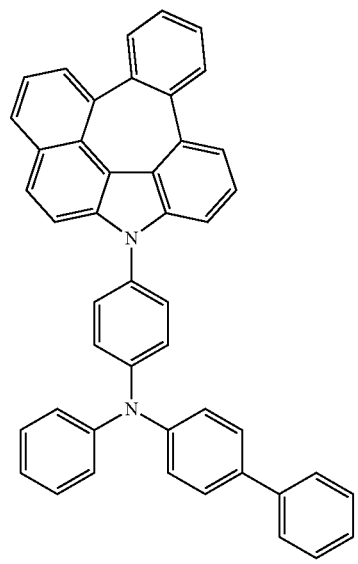 [SMILES: c1ccc(-c2ccc(N(c3ccccc3)c3ccc(-n4c5cccc6c5c5c7c(cccc7ccc54)-c4ccccc4-6)cc3)cc2)cc1]
H-120
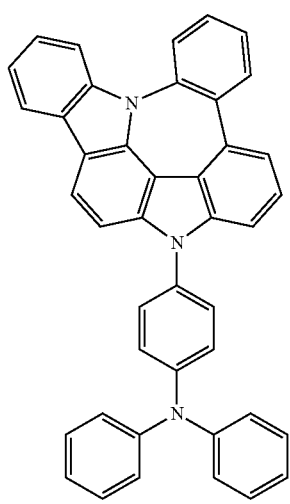 [SMILES: c1ccc(N(c2ccccc2)c2ccc(-n3c4cccc5c6ccccc6n6c7ccccc7c7ccc3c(c54)c76)cc2)cc1]
H-31
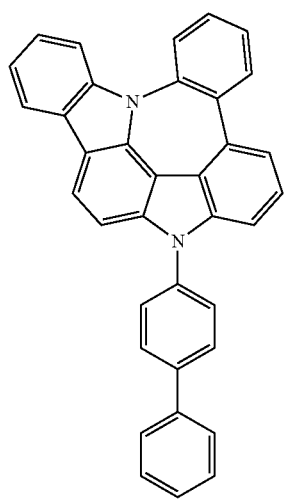 [SMILES: c1ccc(-c2ccc(-n3c4cccc5c6ccccc6n6c7ccccc7c7ccc3c(c54)c76)cc2)cc1]

TABLE 2-continued
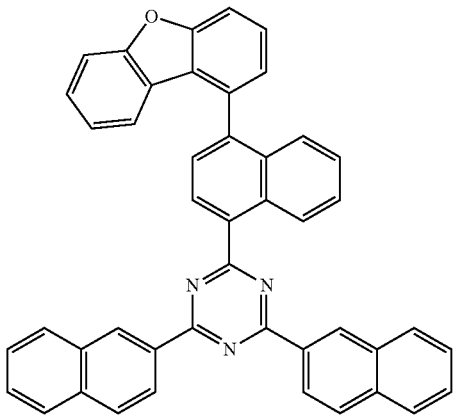 [SMILES: c1ccc2cc(-c3nc(-c4ccc5ccccc5c4)nc(-c4ccc(-c5cccc6oc7ccccc7c56)c5ccccc45)n3)ccc2c1]
E-112
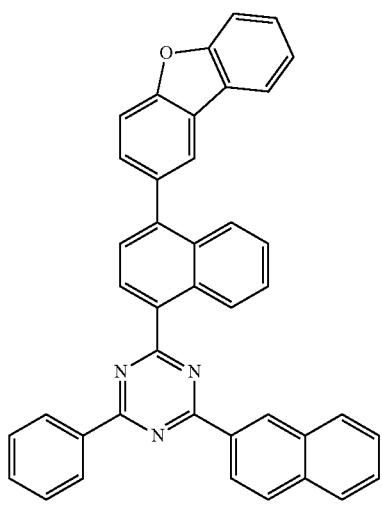 [SMILES: c1ccc(-c2nc(-c3ccc4ccccc4c3)nc(-c3ccc(-c4ccc5oc6ccccc6c5c4)c4ccccc34)n2)cc1]
E-115
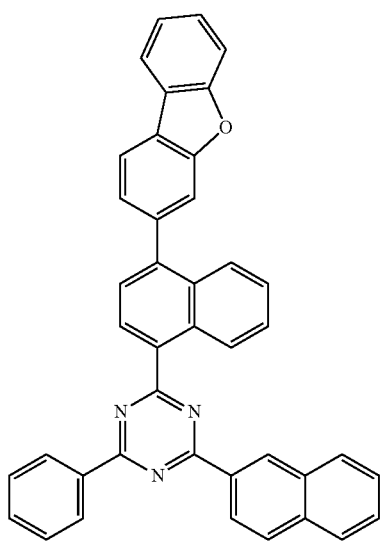 [SMILES: c1ccc(-c2nc(-c3ccc4ccccc4c3)nc(-c3ccc(-c4ccc5c(c4)oc4ccccc45)c4ccccc34)n2)cc1]
E-136

TABLE 2-continued

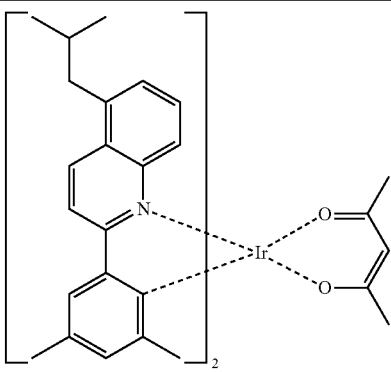

D-39

Electron Transport Layer/Electron Injection Layer

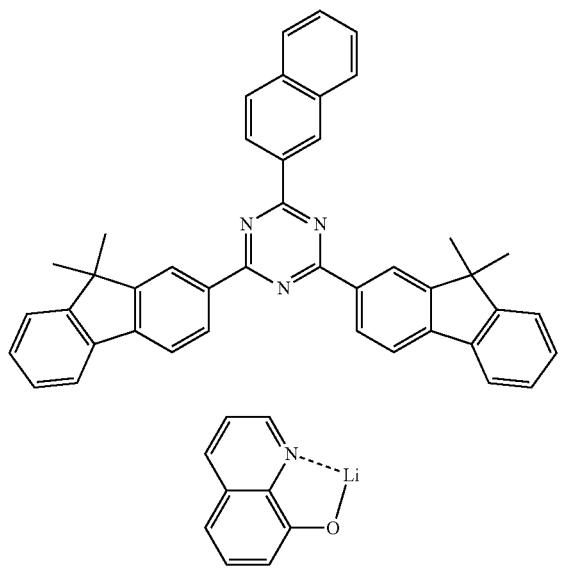

ET-1

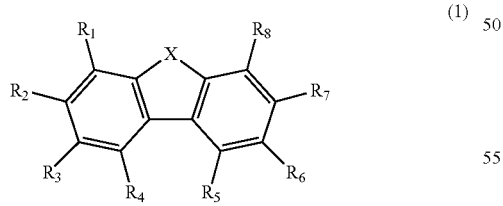

EI-1

The invention claimed is:

1. A plurality of host materials comprising a first host material comprising a compound represented by the following formula 1, and a second host material comprising a compound represented by the following formula 2:

$$\text{(1)}$$

wherein
X represents O;
$R_1$ to $R_8$ each independently represent-$L_1$-HAr, hydrogen, deuterium, a halogen, a cyano, a substituted or unsubstituted (C1-C30) alkyl, a substituted or unsubstituted (C3-C30) cycloalkyl, a substituted or unsubstituted (C3-C30) cycloalkenyl, a substituted or unsubstituted (3-to 7-membered) heterocycloalkyl, a substituted or unsubstituted (C6-C30) aryl, a substituted or unsubstituted (3-to 30-membered) heteroaryl,-$NR_9R_{10}$, or-$SiR_{11}R_{12}R_{13}$; or may be linked to an adjacent substituent to form a ring; with a proviso that at least one of $R_3$ to $R_6$ is-$L_1$-HAr;
$L_1$ represents a single bond, a substituted or unsubstituted (C1-C30) alkylene, a substituted or unsubstituted (C6-C30) arylene, a substituted or unsubstituted (3-to 30-membered) heteroarylene, or a substituted or unsubstituted (C3-C30) cycloalkylene, where if a plurality of $L_1$ is present, each of $L_1$ may be the same or different;
HAr represents a substituted or unsubstituted nitrogen-containing (3-to 30-membered) heteroaryl, where if a plurality of HAr is present, each HAr may be the same or different;
with proviso that (1) when HAr is a substituted or unsubstituted triazine and $L_1$ is a substituted or unsubstituted (C6-C30) arylene, the (C6-30) arylene is selected from the group consisting of a naphthylene, a naphthylphenylene, or a phenylnaphthylene;
or (2) when HAr is a substituted triazine and $L_1$ is a substituted or unsubstituted phenylene, or a substituted or unsubstituted biphenylene, at least one of substitutions in HAr is a naphthyl, a phenylnaphthyl, or a naphthylphenyl; or
(3) when HAr is a substituted triazine and $L_1$ is a single bond, one of two substitutions in HAr is a naphthyl, or a naphthylphenyl and the other one of two substitutions in HAr is a (C6-C30) aryl unsubstituted or substituted with at least one of a deuterium, a (C1-C30) alkyl(s), a (3-to 30-membered) heteroaryl(s), and a di (C6-C30) arylamino(s);

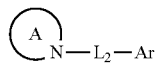
(2)

wherein $L_2$ represents a single bond, a substituted or unsubstituted (C1-C30) alkylene, a substituted or unsubstituted (C6-C30) arylene, a substituted or unsubstituted (3-to 30-membered) heteroarylene, or a substituted or unsubstituted (C3-C30) cycloalkylene;

Ar represents hydrogen, deuterium, a halogen, a cyano, a substituted or unsubstituted (C1-C30) alkyl, a substituted or unsubstituted (C3-C30) cycloalkyl, a substituted or unsubstituted (C3-C30) cycloalkenyl, a substituted or unsubstituted (3-to 7-membered) heterocycloalkyl, a substituted or unsubstituted (C6-C30) aryl, a substituted or unsubstituted (3-to 30-membered) heteroaryl, -$NR_9R_{10}$, or -$SiR_{11}R_{12}R_{13}$;

or may be linked to an adjacent substituent to form a ring;

is represented by the following formula 3;

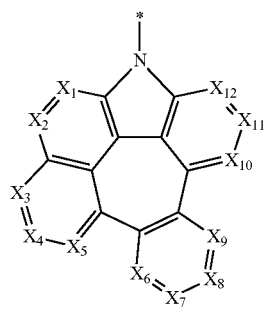
(3)

wherein $X_1$ to $X_{12}$ each independently represent N or $CR_{14}$;

$R_{14}$ each independently represent hydrogen, deuterium, a halogen, a cyano, a substituted or unsubstituted (C1-C30) alkyl, a substituted or unsubstituted (C6-C30) aryl, a substituted or unsubstituted (3-to 30-membered) heteroaryl, a substituted or unsubstituted (C3-C30) cycloalkyl, a substituted or unsubstituted (C1-C30) alkoxy, a substituted or unsubstituted tri (C1-C30) alkylsilyl, a substituted or unsubstituted di (C1-C30) alkyl (C6-C30) arylsilyl, a substituted or unsubstituted (C1-C30) alkyldi (C6-C30) arylsilyl, a substituted or unsubstituted tri (C6-C30) arylsilyl, a substituted or unsubstituted mono-or di-(C1-C30) alkylamino, a substituted or unsubstituted mono-or di-(C6-C30) arylamino, or a substituted or unsubstituted (C1-C30) alkyl (C6-C30) arylamino; or adjacent $R_{14}$'s may be linked to each other to form a ring, and where if a plurality of $R_{14}$ is present, each $R_{14}$ may be the same or different;

$R_9$ to $R_{13}$ each independently represent a substituted or unsubstituted (C1-C30) alkyl, a substituted or unsubstituted (C6-C30) aryl, or a substituted or unsubstituted (3-to 30-membered) heteroaryl; and

* represents a bonding site with $L_2$.

2. The plurality of host materials according to claim 1, wherein the substituents of the substituted alkyl, the substituted alkylene, the substituted aryl, the substituted arylene, the substituted heteroaryl, the substituted heteroarylene, the substituted cycloalkyl, the substituted cycloalkylene, the substituted cycloalkenyl, the substituted heterocycloalkyl, the substituted alkoxy, the substituted trialkylsilyl, the substituted dialkylarylsilyl, the substituted alkyldiarylsilyl, the substituted triarylsilyl, the substituted mono-or di-alkylamino, the substituted mono-or di-arylamino, and the substituted alkylarylamino in $R_1$ to $R_{14}$, $L_1$, $L_2$, HAr, and Ar, each independently, are at least one selected from the group consisting of deuterium; a halogen; a cyano; a carboxyl; a nitro; a hydroxyl; a (C1-C30) alkyl; a halo (C1-C30) alkyl; a (C2-C30) alkenyl; a (C2-C30) alkynyl; a (C1-C30) alkoxy; a (C1-C30) alkylthio; a (C3-C30) cycloalkyl; a (C3-C30) cycloalkenyl; a (3-to 7-membered) heterocycloalkyl; a (C6-C30) aryloxy; a (C6-C30) arylthio; a (3-to 30-membered) heteroaryl unsubstituted or substituted with a (C6-C30) aryl(s); a (C6-C30) aryl unsubstituted or substituted with at least one of a (C1-C30) alkyl(s), a (3-to 30-membered) heteroaryl(s), and a di (C6-C30) arylamino(s); a tri (C1-C30) alkylsilyl; a tri (C6-C30) arylsilyl; a di (C1-C30) alkyl (C6-C30) arylsilyl; a (C1-C30) alkyldi (C6-C30) arylsilyl; an amino; a mono-or di-(C1-C30) alkylamino; a mono-or di-(C6-C30) arylamino; a (C1-C30) alkyl (C6-C30) arylamino; a (C1-C30) alkylcarbonyl; a (C1-C30) alkoxycarbonyl; a (C6-C30) arylcarbonyl; a di (C6-C30) arylboronyl; a di (C1-C30) alkylboronyl; a (C1-C30) alkyl (C6-C30) arylboronyl; a (C6-C30) aryl (C1-C30) alkyl; and a (C1-C30) alkyl (C6-C30) aryl.

3. The plurality of host materials according to claim 1, wherein formula 1 is represented by at least one of the following formulas 1-3 to 1-4:

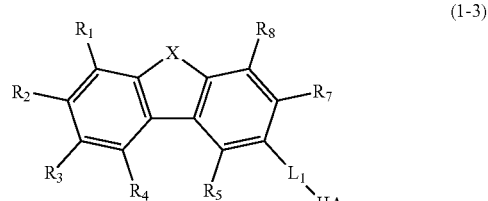
(1-3)

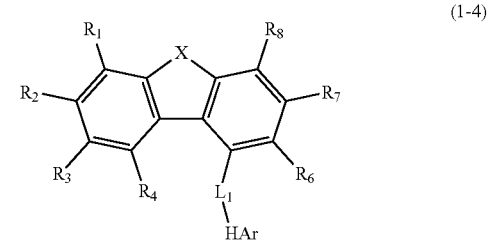
(1-4)

wherein
R₁ to R₈, X, L₁, and HAr are as defined in claim 1.

4. The plurality of host materials according to claim 1, wherein formula 3 is represented by the following formula 3-1:

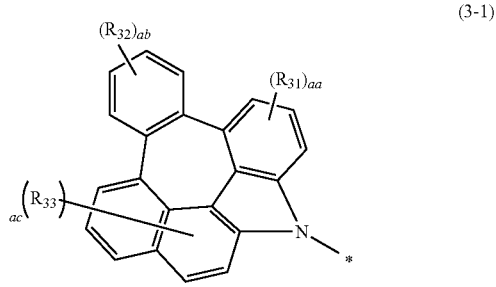

(3-1)

wherein
R₃₁ to R₃₃ each independently represent hydrogen, deuterium, a halogen, a cyano, a substituted or unsubstituted (C1-C30) alkyl, a substituted or unsubstituted (C6-C30) aryl, a substituted or unsubstituted (3-to 30-membered) heteroaryl, a substituted or unsubstituted (C3-C30) cycloalkyl, a substituted or unsubstituted (C1-C30) alkoxy, a substituted or unsubstituted tri (C1-C30) alkylsilyl, a substituted or unsubstituted di (C1-C30) alkyl (C6-C30) arylsilyl, a substituted or unsubstituted (C1-C30) alkyldi (C6-C30) arylsilyl, a substituted or unsubstituted tri (C6-C30) arylsilyl, a substituted or unsubstituted mono-or di-(C1-C30) alkylamino, a substituted or unsubstituted mono-or di-(C6-C30) arylamino, or a substituted or unsubstituted (C1-C30) alkyl (C6-C30) arylamino; or may be linked to an adjacent substituent to form a ring; and aa represents an integer of 1 to 3, ab represents an integer of 1 to 4, ac represents an integer of 1 to 5, where if aa, ab, and ac are an integer of 2 or more, each R₃₁, each R₃₂, and each R₃₃ may be the same or different.

5. The plurality of host materials according to claim 1, wherein HAr represents a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted triazanaphthyl, or a substituted or unsubstituted benzothienopyrimidinyl.

6. The plurality of host materials according to claim 1, wherein Ar represents a substituted or unsubstituted phenyl, a substituted or unsubstituted naphthyl, a substituted or unsubstituted biphenyl, a substituted or unsubstituted naphthylphenyl, a substituted or unsubstituted phenylnaphthyl, a substituted or unsubstituted terphenyl, a substituted or unsubstituted carbazolyl, a substituted or unsubstituted benzocarbazolyl, a substituted or unsubstituted dibenzocarbazolyl, a substituted or unsubstituted dibenzothiophenyl, a substituted or unsubstituted benzothiophenyl, a substituted or unsubstituted benzonaphthothiophenyl, a substituted or unsubstituted dibenzofuranyl, a substituted or unsubstituted benzofuranyl, a substituted or unsubstituted benzonaphthofuranyl, a substituted or unsubstituted diazadibenzofuranyl, a substituted or unsubstituted pyridyl, a substituted or unsubstituted pyrimidinyl, a substituted or unsubstituted triazinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted benzothienopyrimidinyl, a substituted or unsubstituted fluorenyl, a substituted or unsubstituted benzofluorenyl, a substituted or unsubstituted spirobifluorenyl, a substituted or unsubstituted diphenylamino, a substituted or unsubstituted phenylnaphthylamino, a substituted or unsubstituted phenylbiphenylamino, a substituted or unsubstituted naphthylbiphenylamino, a substituted or unsubstituted dibiphenylamino, a substituted or unsubstituted biphenylfluorenylamino, or a substituted or unsubstituted biphenyldibenzofuranylamino.

7. The plurality of host materials according to claim 1, wherein the compound represented by formula 1 is at least one selected from the following compounds:

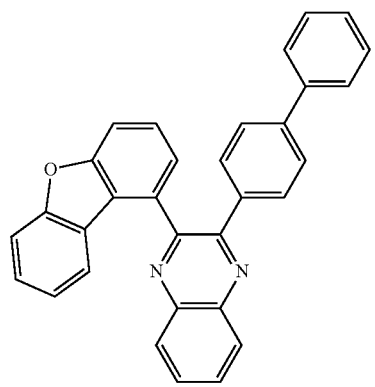

E-1

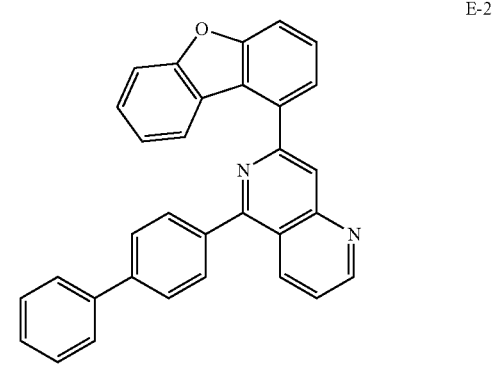

E-2

E-3
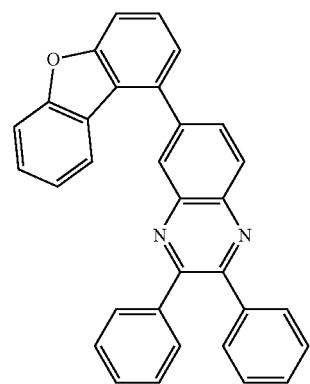
E-4
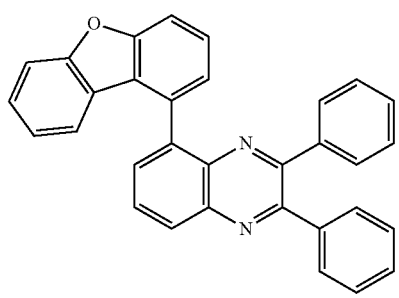
E-5
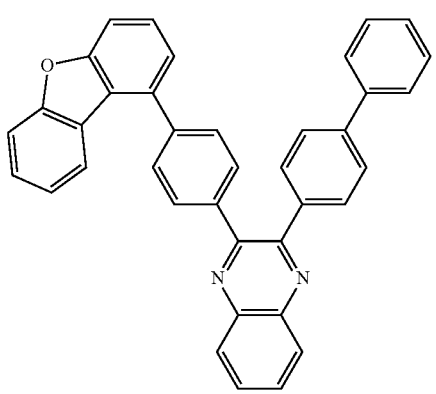
E-6
E-7
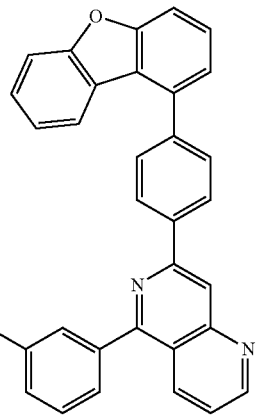
E-8
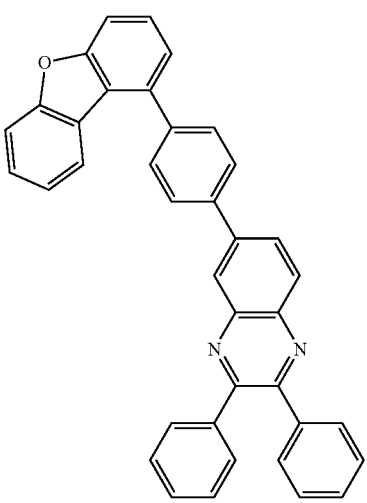
E-9
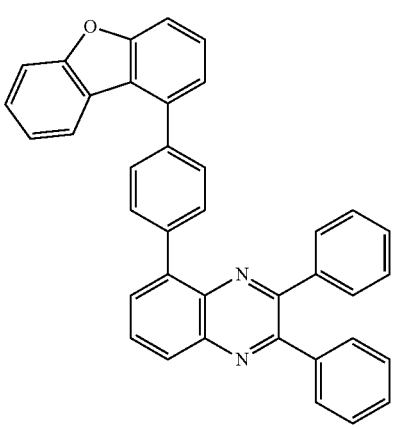

-continued
E-10
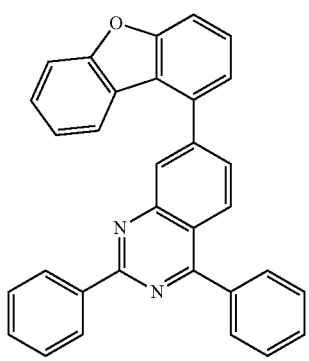
E-11
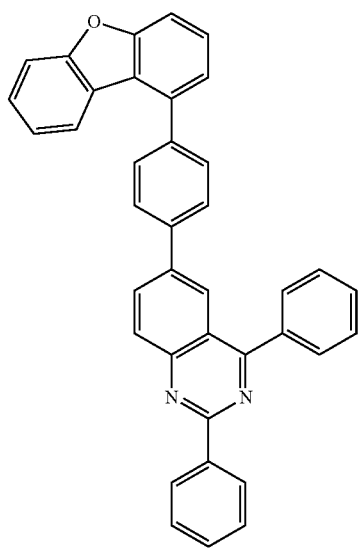
E-12
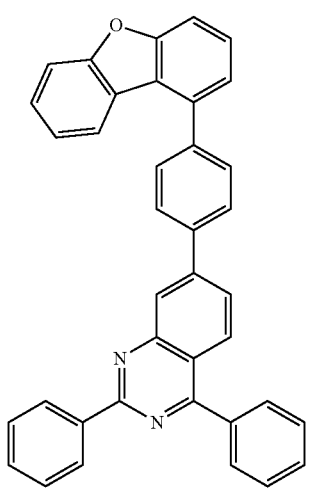
-continued
E-13
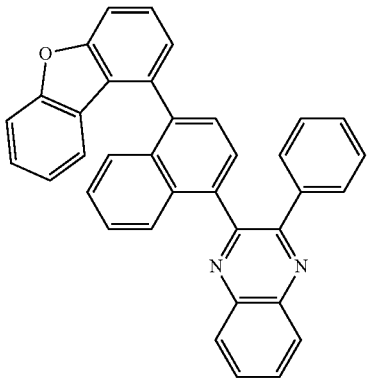
E-14
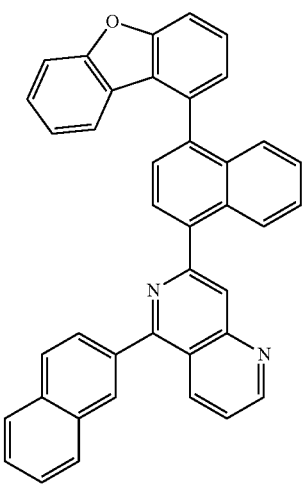
E-15
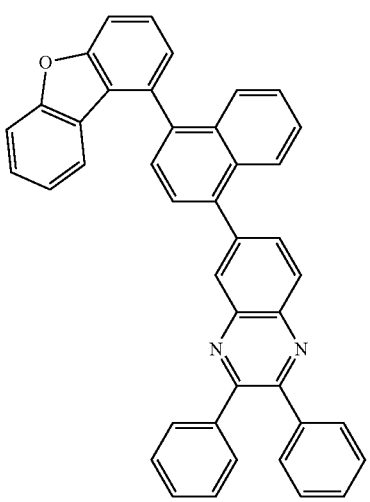

-continued
E-16
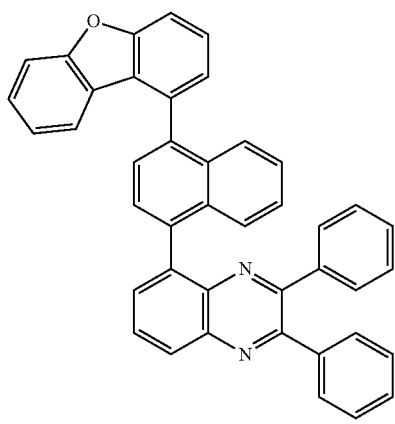
E-17
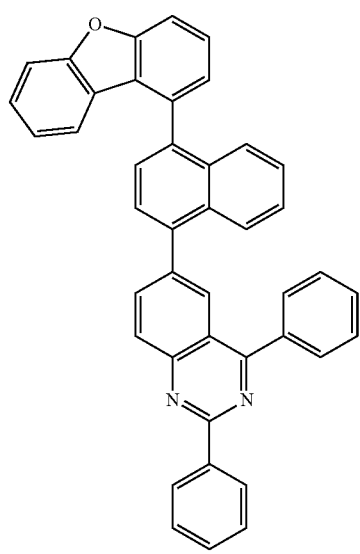
E-18
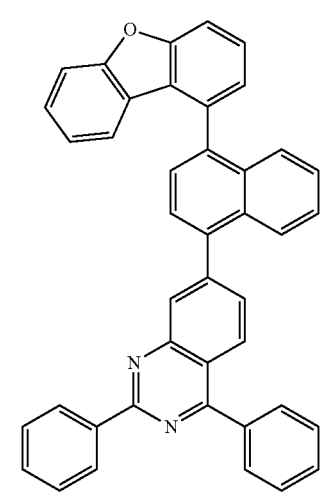
-continued
E-19
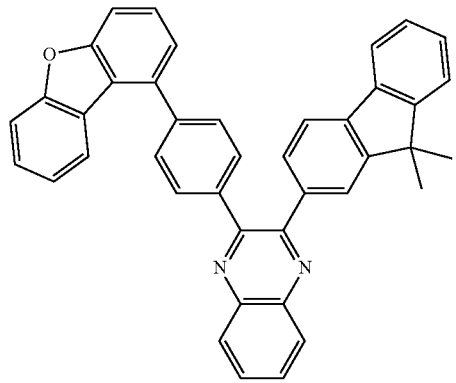
E-20
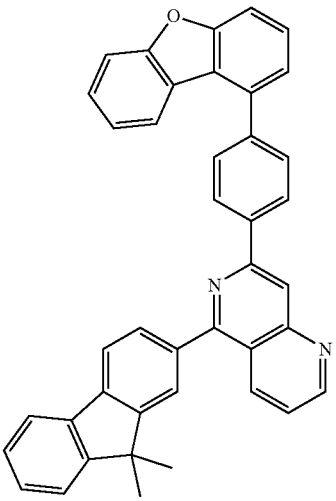
E-21
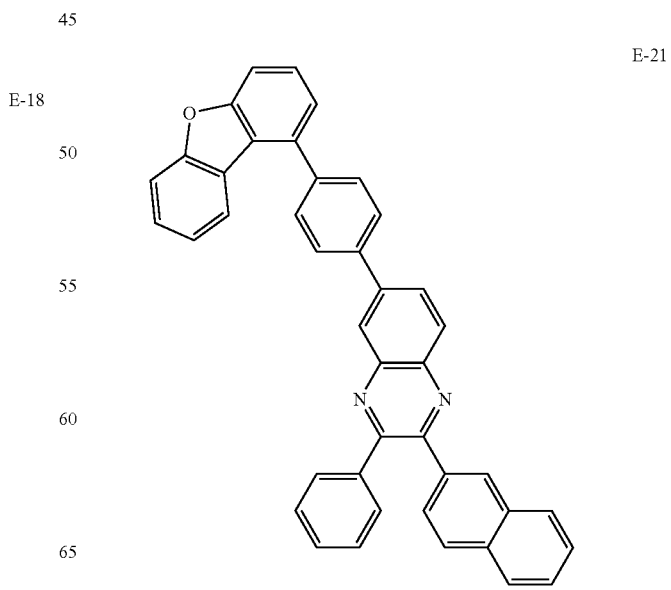

E-22
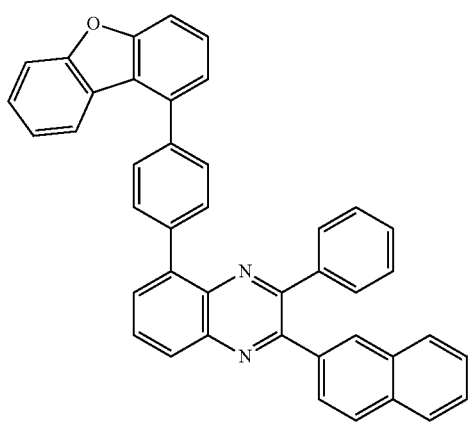
E-23
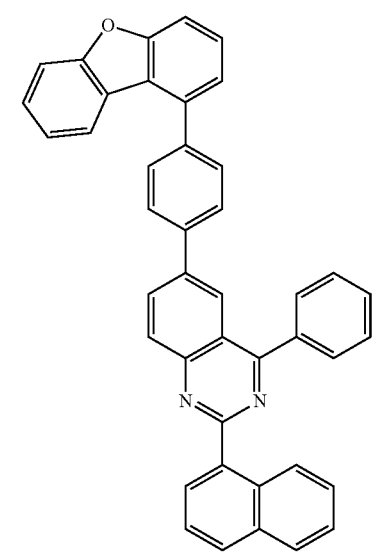
E-24
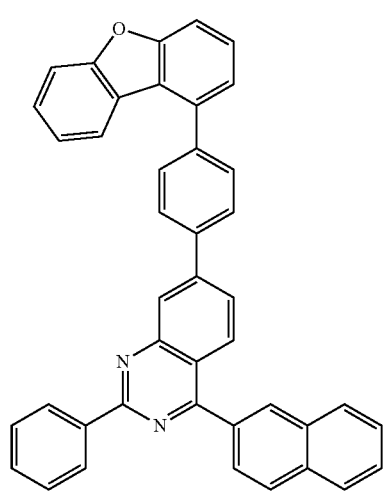
E-25
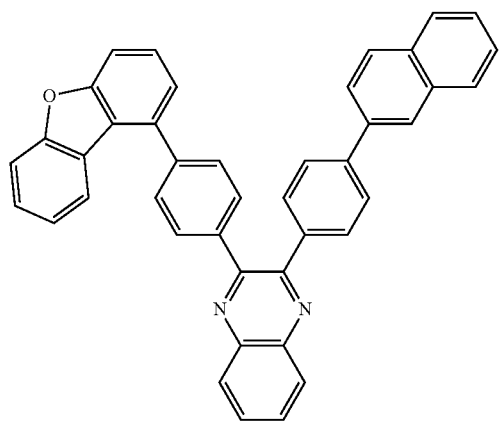
E-26
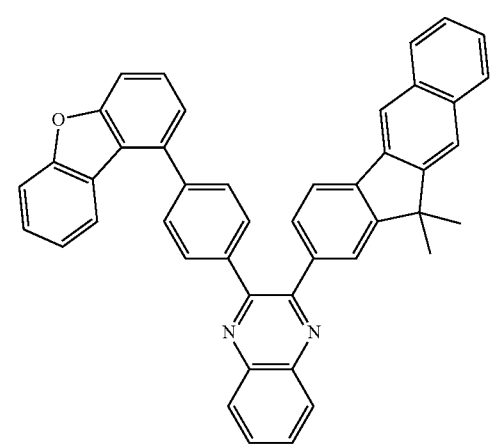
E-27
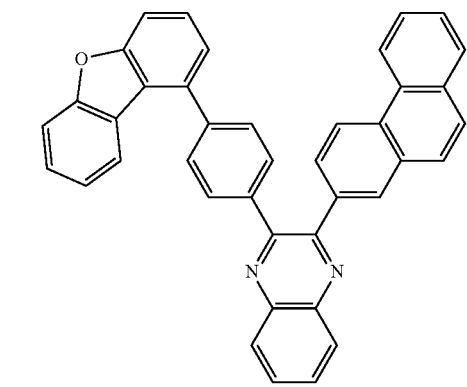
E-28
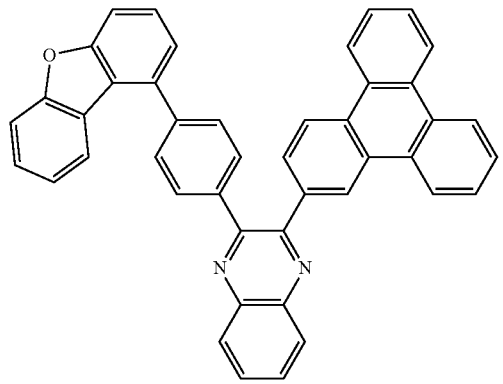

E-29
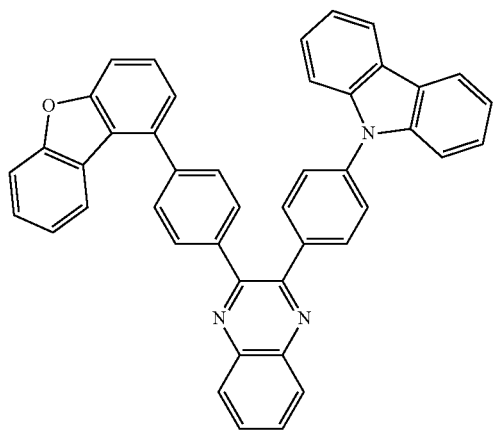
E-30
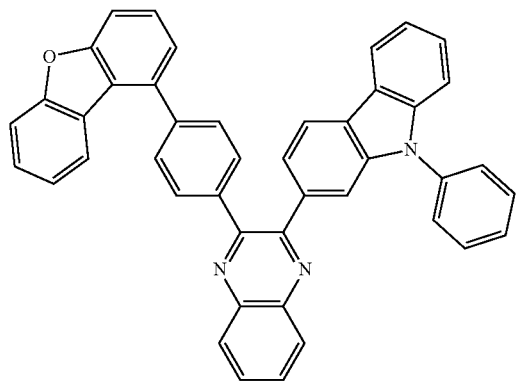
E-31
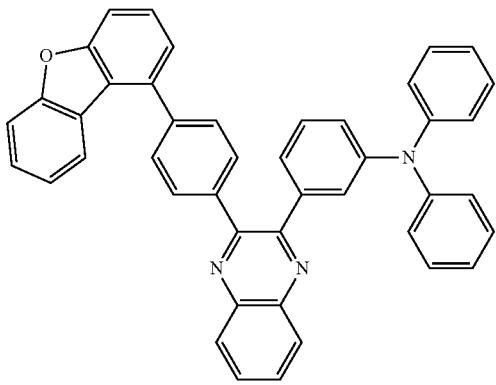
E-32
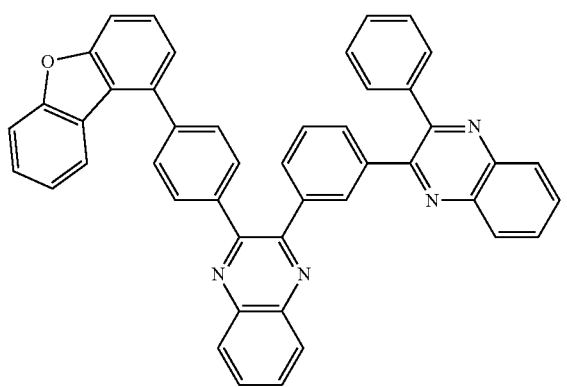
E-33
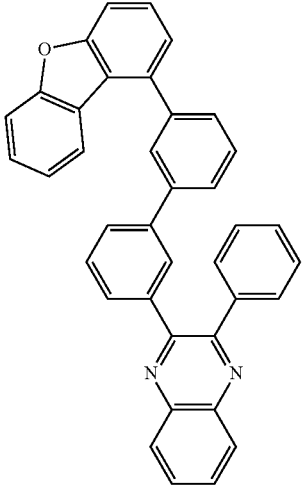
E-34
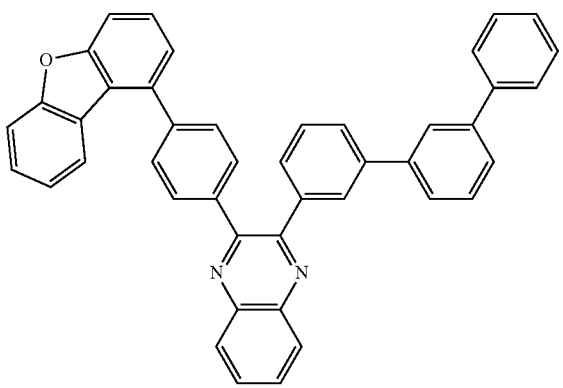
E-37
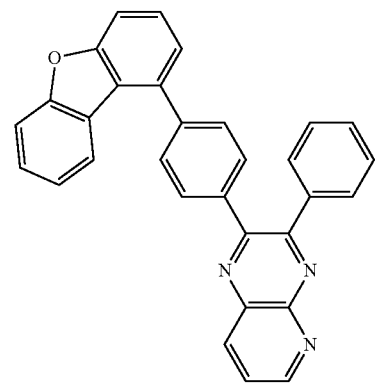

E-38
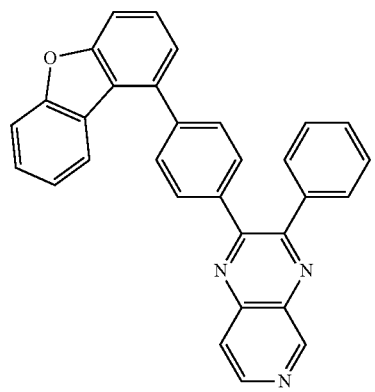
E-39
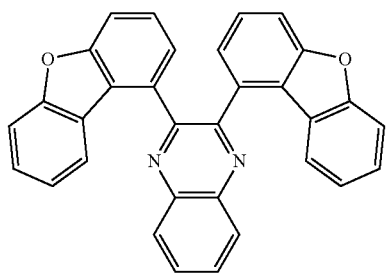
E-40
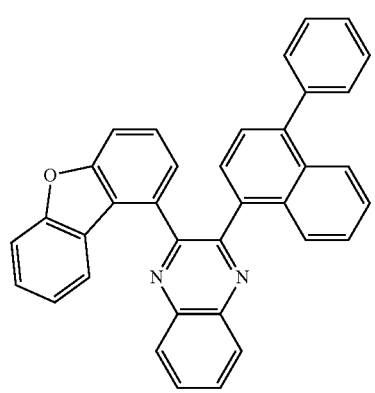
E-41
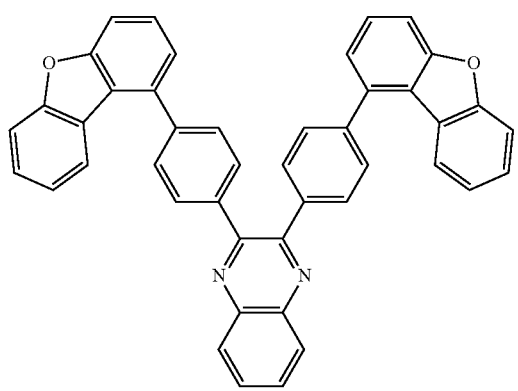
E-42
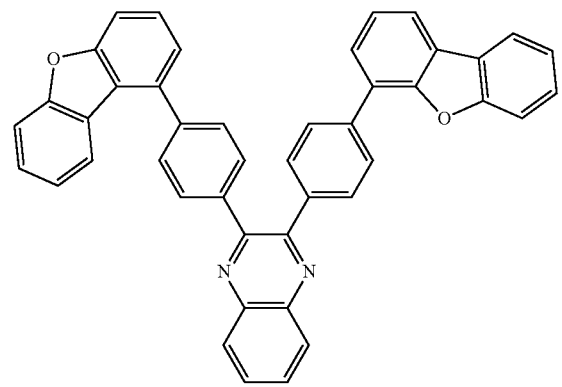
E-43
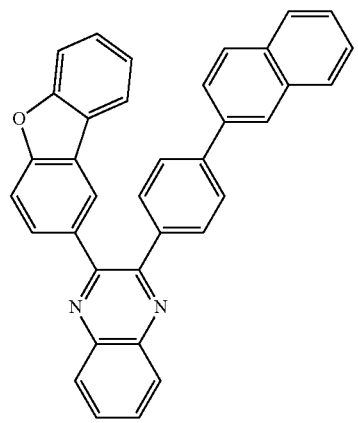
E-44
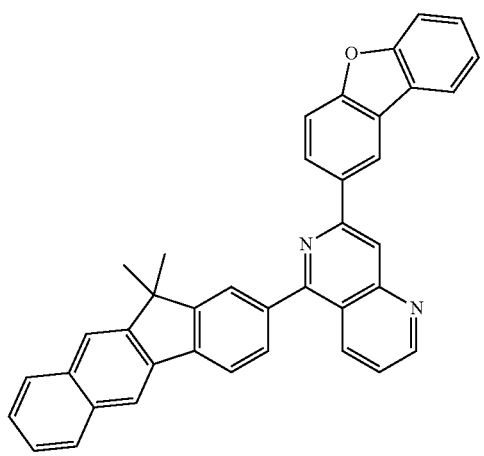

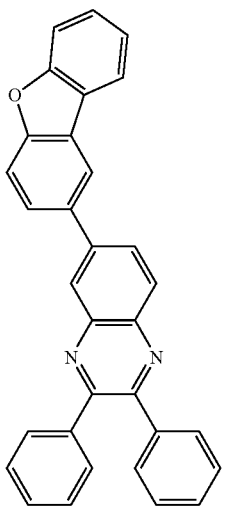 E-45
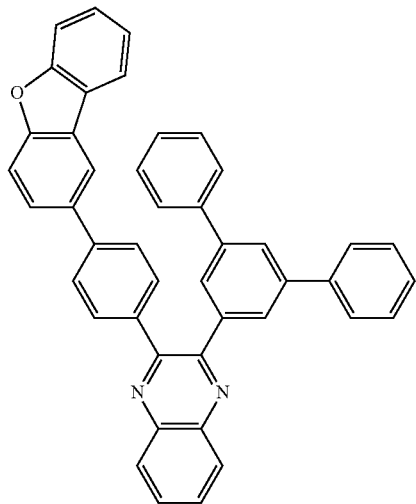 E-48
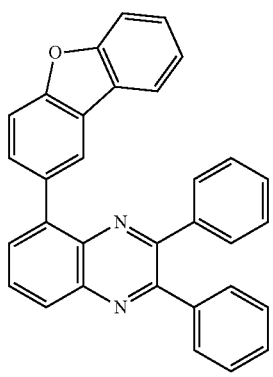 E-46
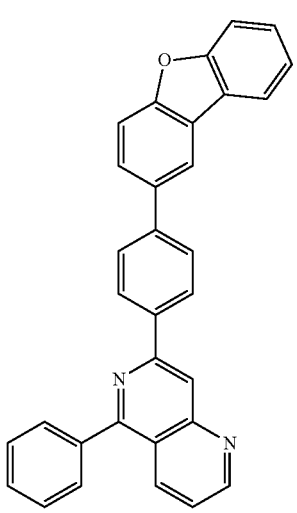 E-49
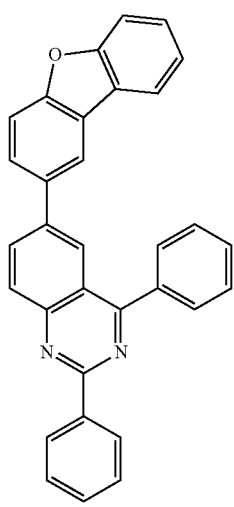 E-47
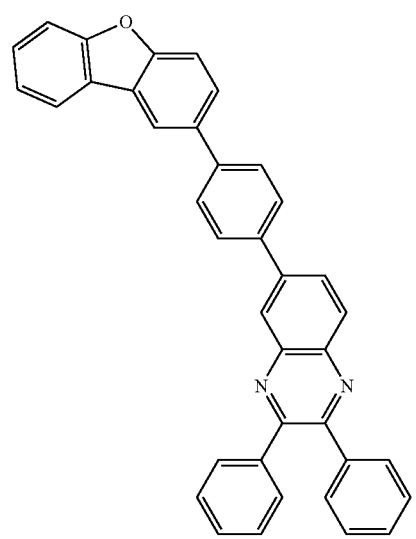 E-50

-continued
E-51
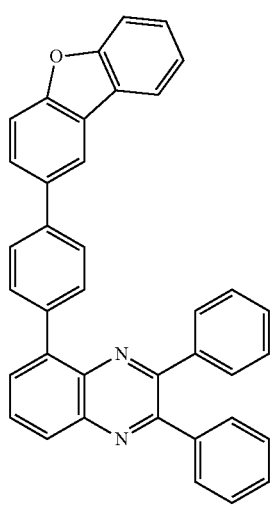
E-53
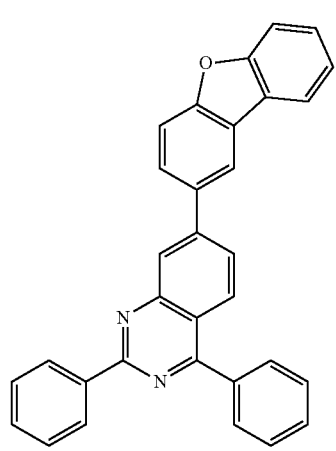
E-57
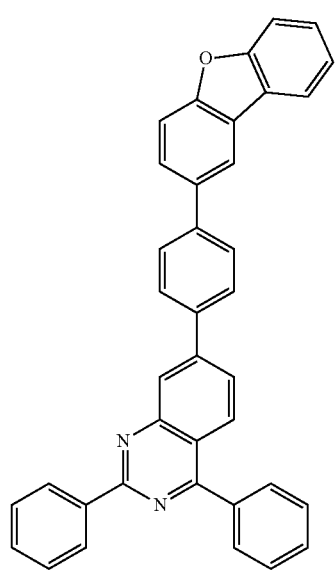
-continued
E-79
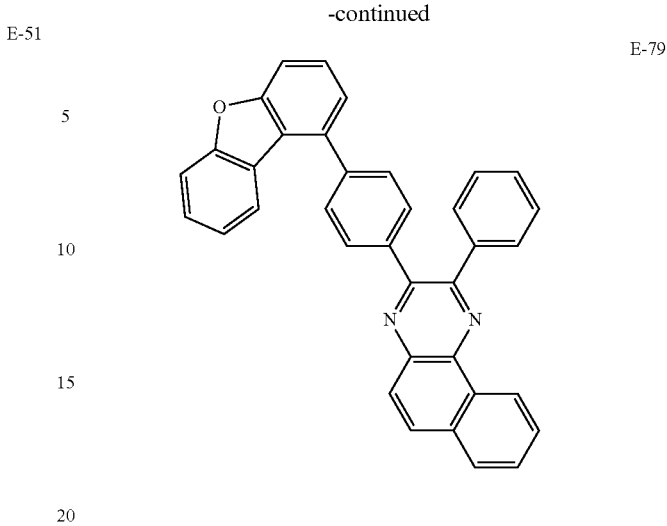
E-80
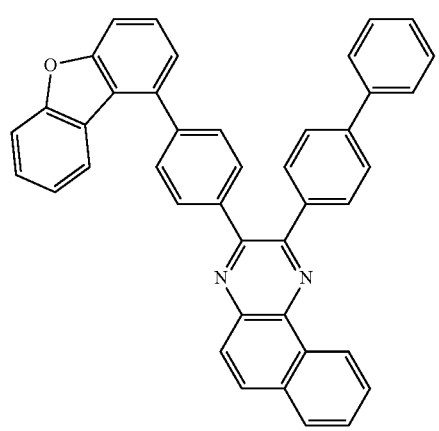
E-81
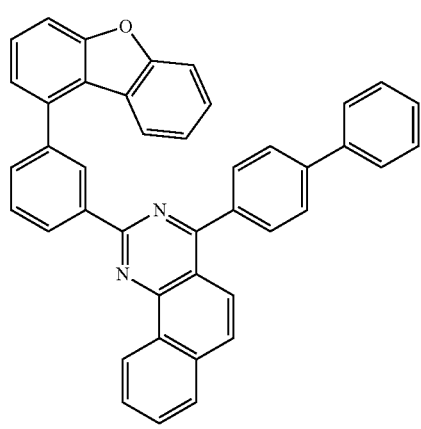

-continued
E-82
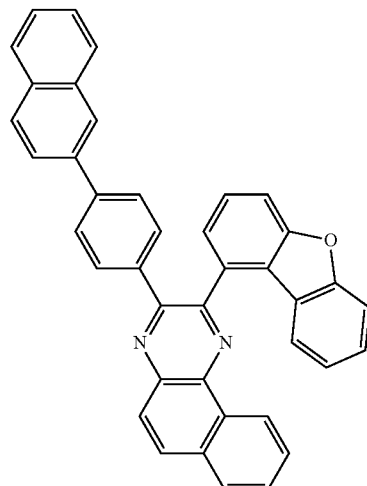
E-83
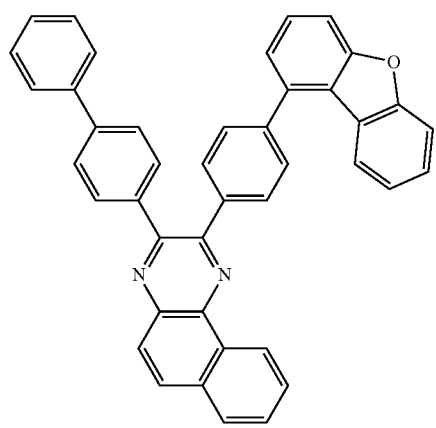
E-84
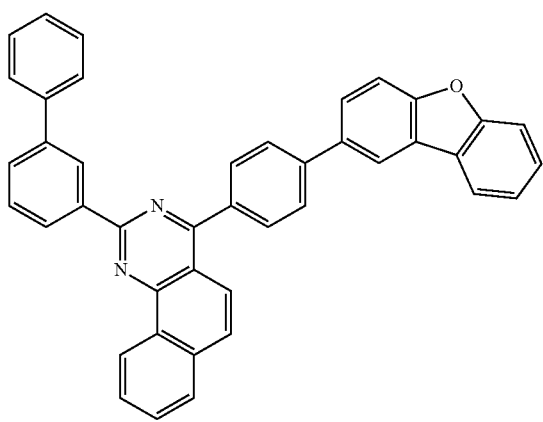
-continued
E-85
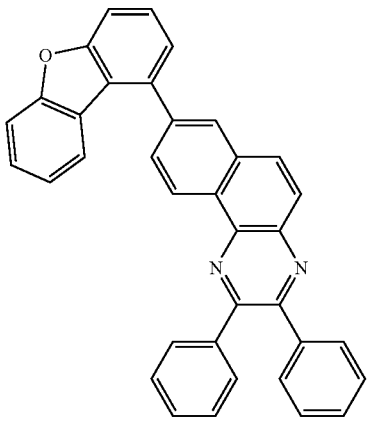
E-86
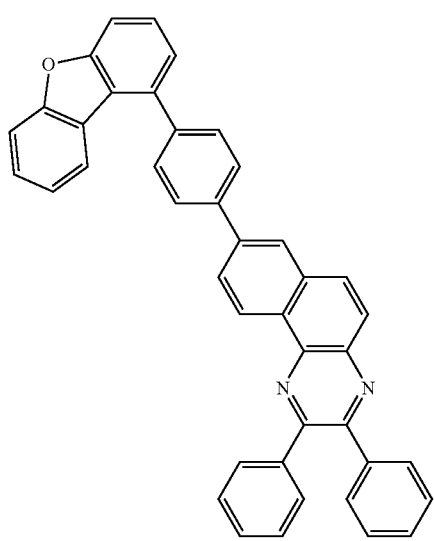
E-87
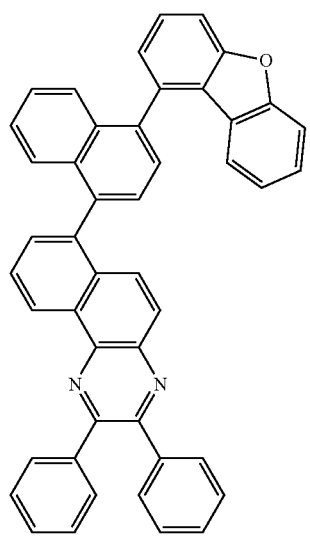

-continued
E-88
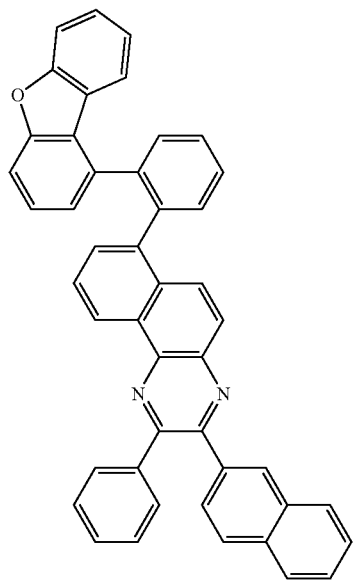
E-106
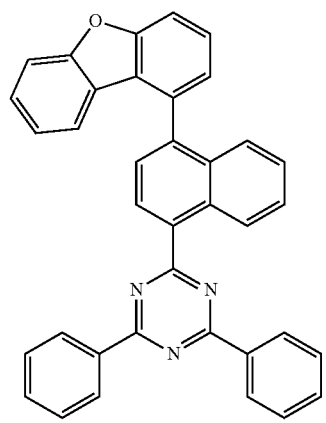
E-109
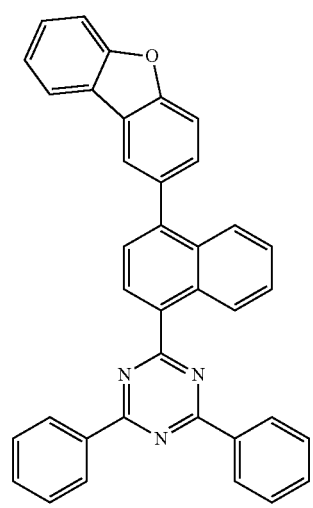
-continued
E-110
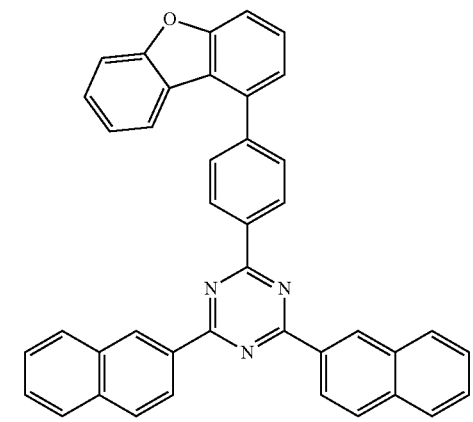
E-111
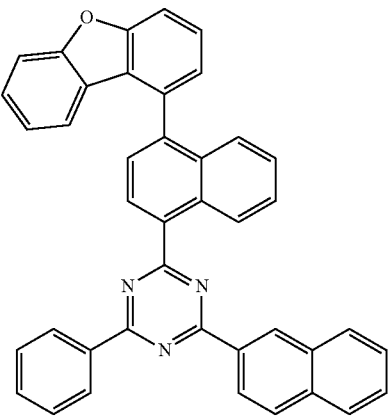
E-112
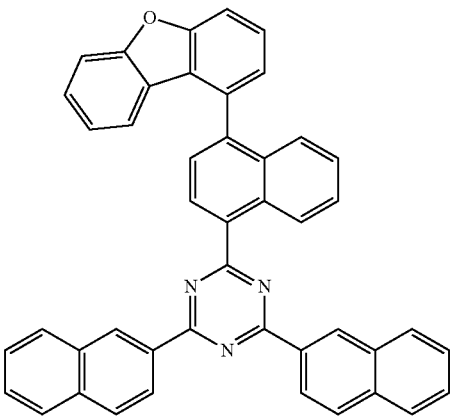

E-113
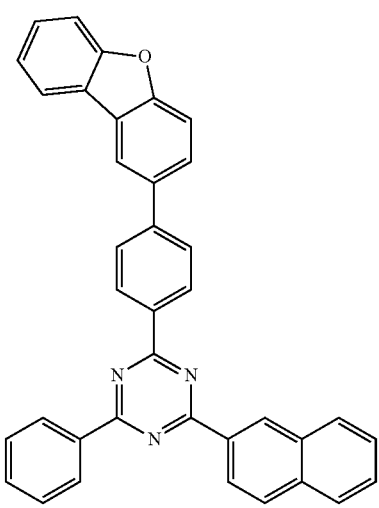
E-114
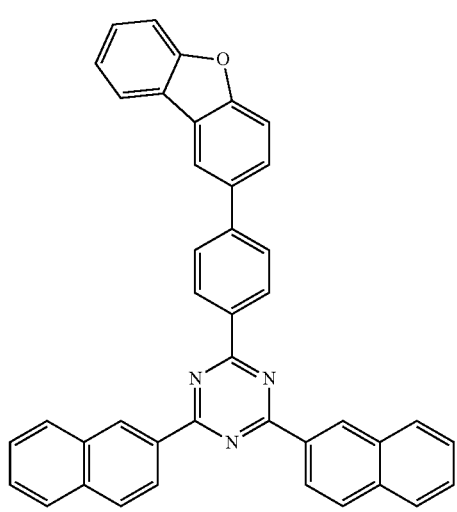
E-115
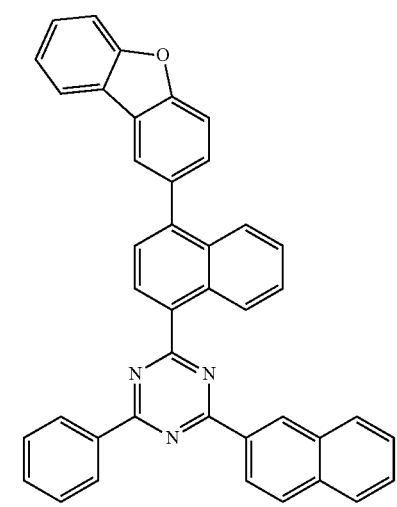
E-117
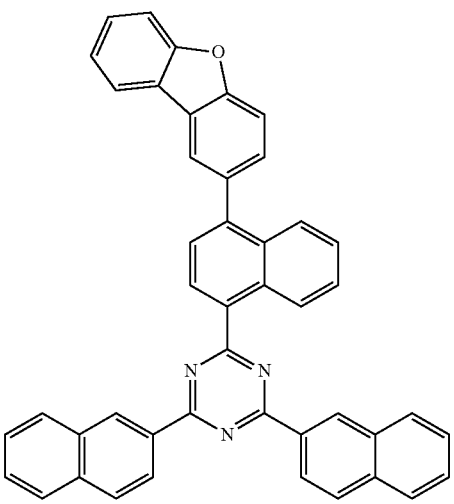
E-118
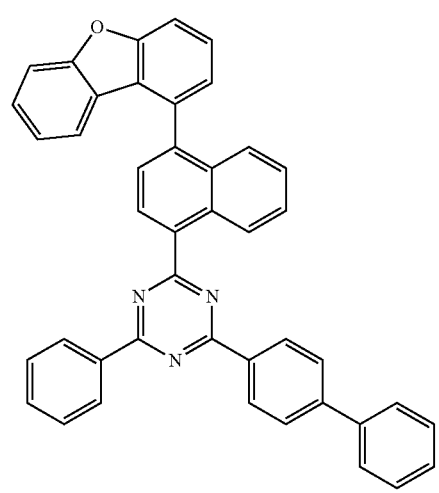
E-123
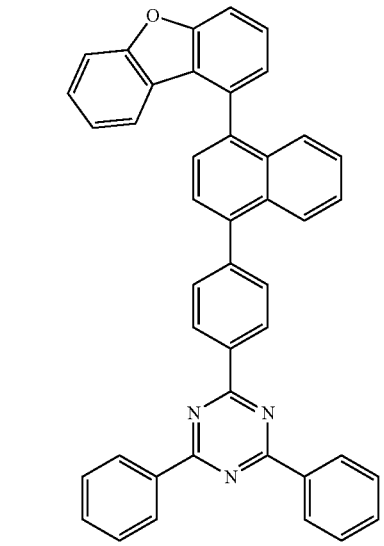

E-124
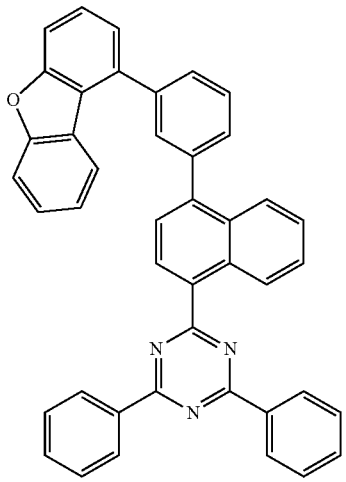
E-131
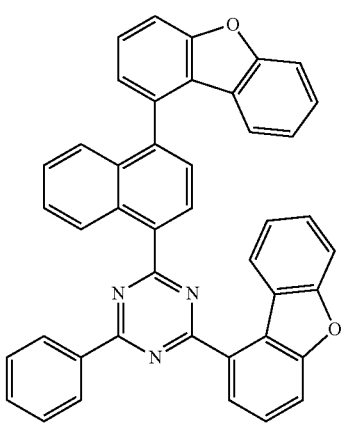
E-137
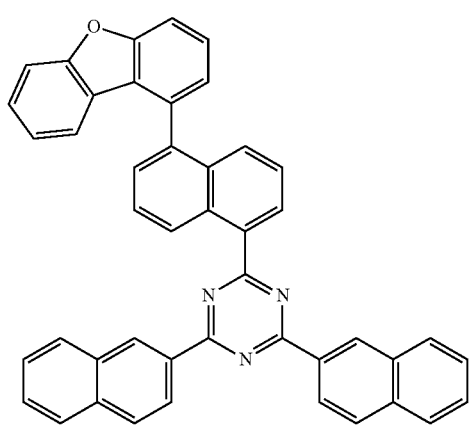
E-138
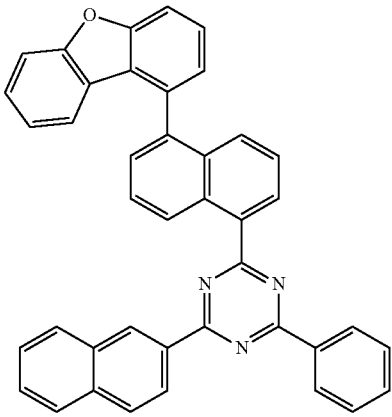
E-139
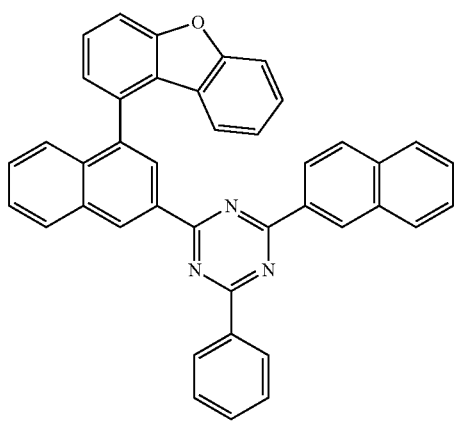
E-140
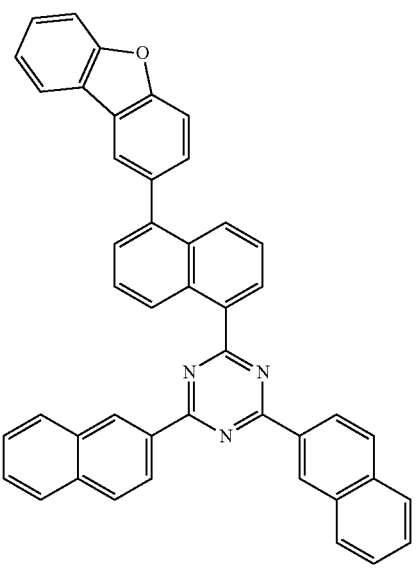

E-141
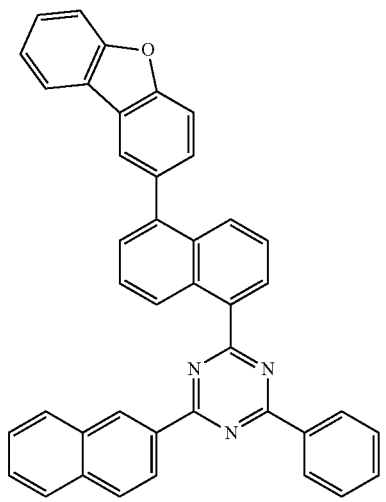
and
E-142
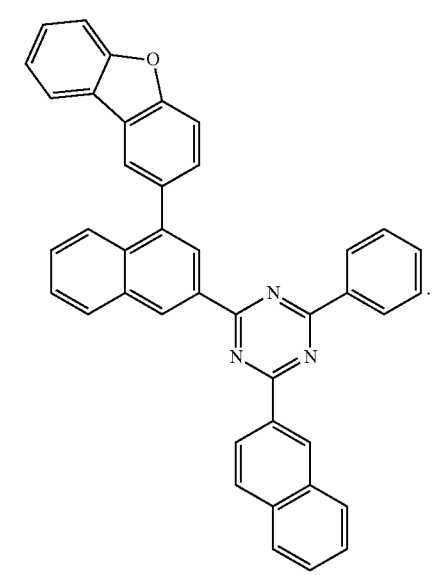
H-1
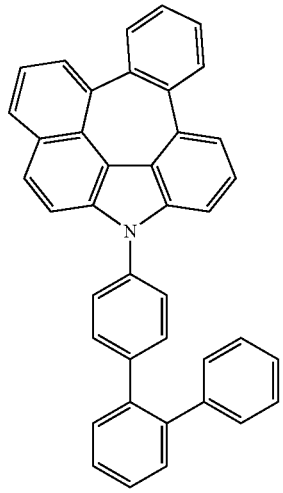
H-2
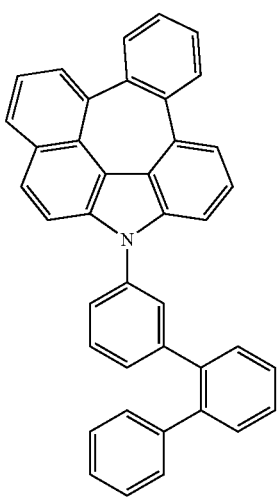
H-3
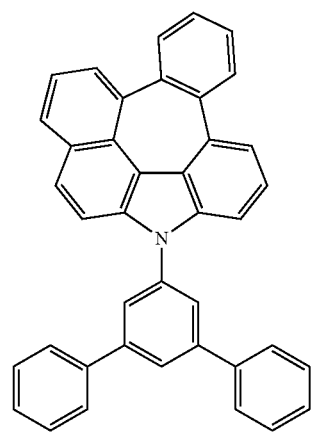
8. The plurality of host materials according to claim 1, wherein the compound represented by formula 2 is at least one selected from the following compounds:

H-4
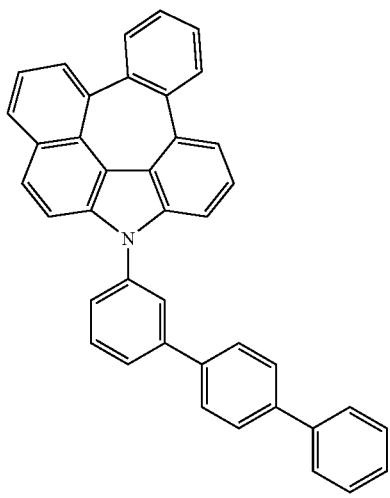
H-8
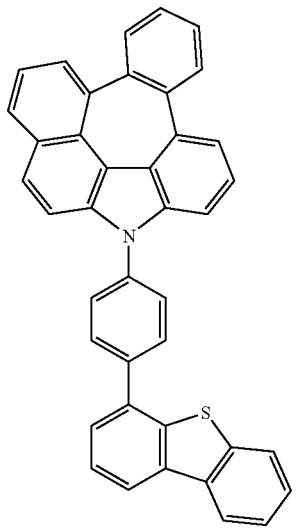
H-6
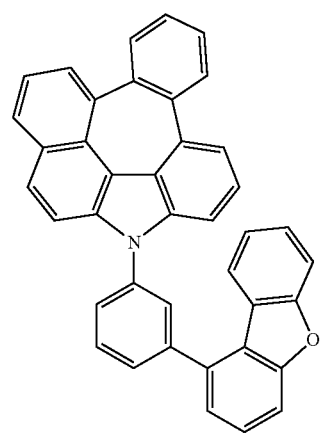
H-11
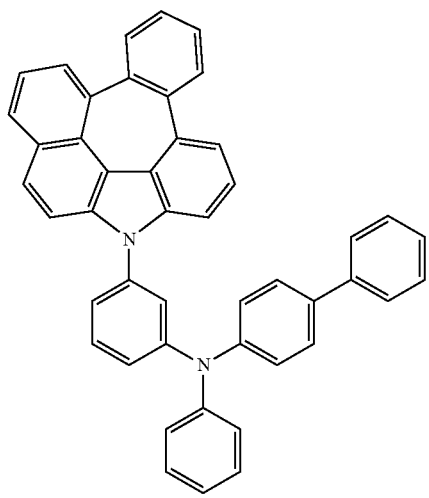
H-7
H-12
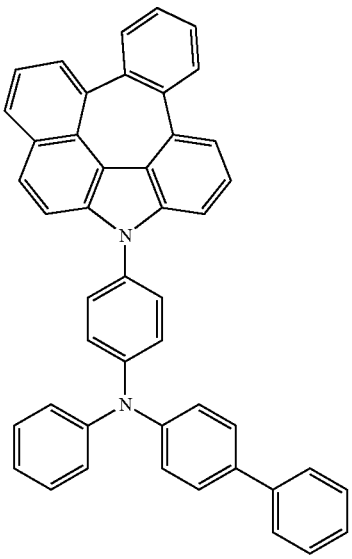

H-13
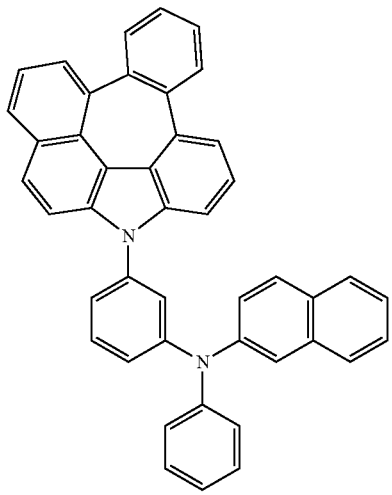
H-16
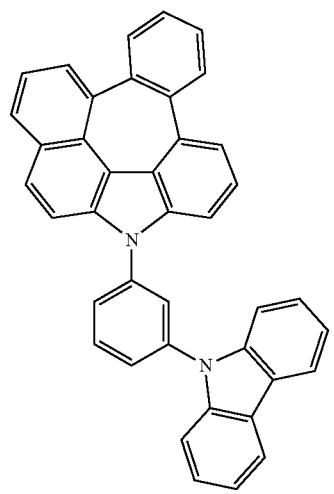
H-17
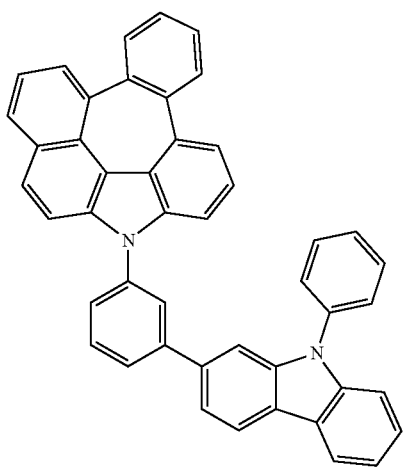
H-18
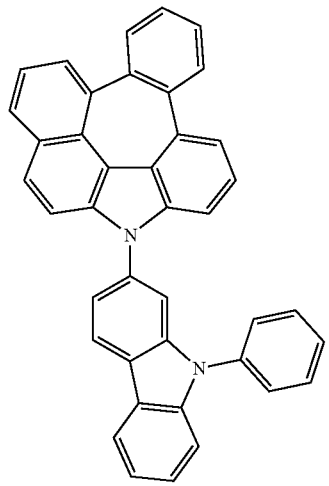
H-26
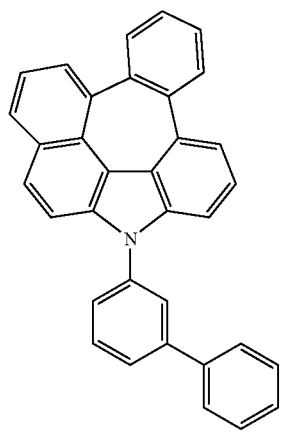
H-27

-continued
H-28
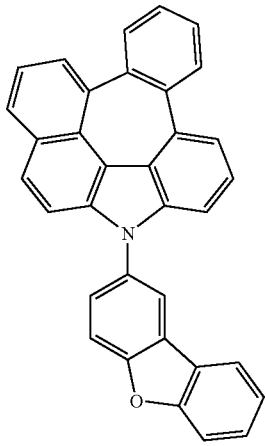
H-32
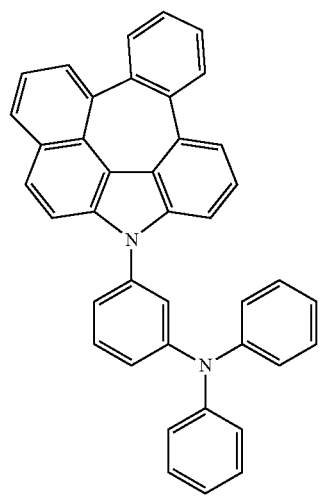
H-33
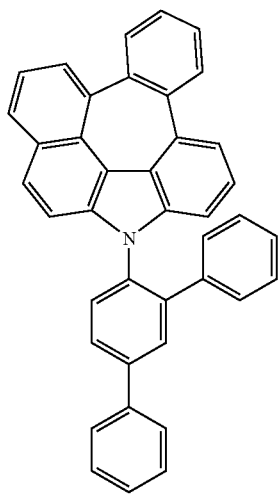
-continued
H-34
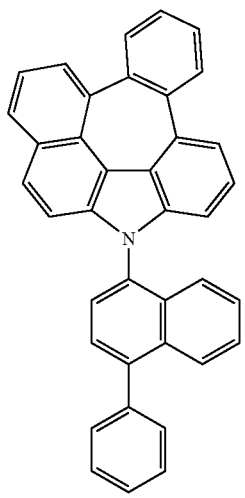
H-38
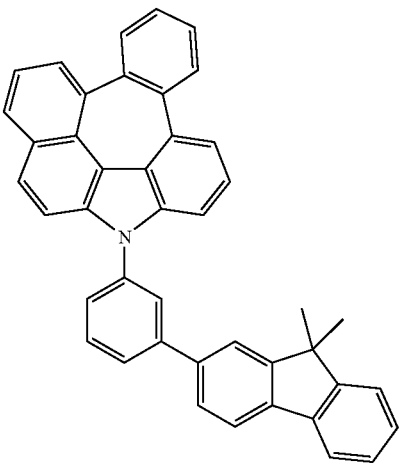
H-39
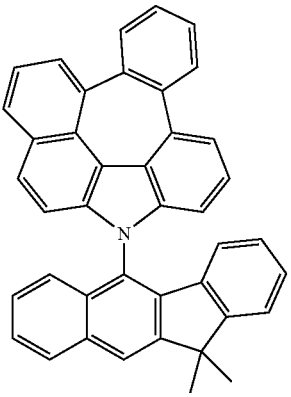

H-40
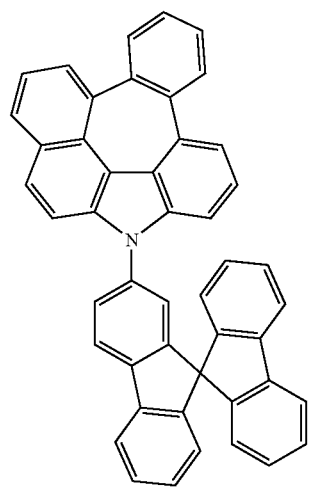
H-43
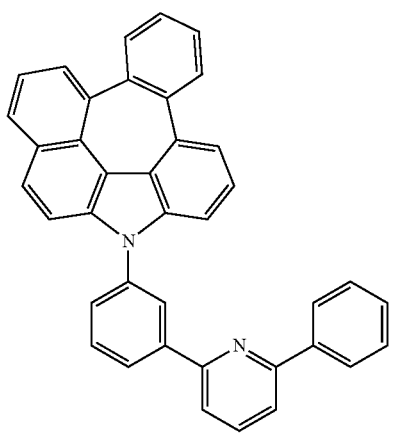
H-44
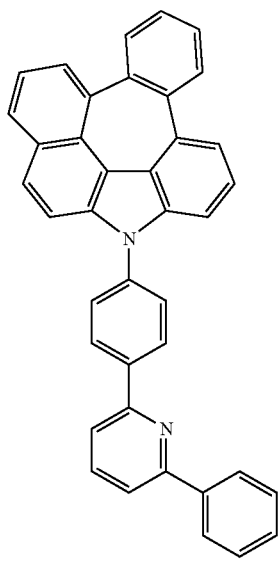
H-45
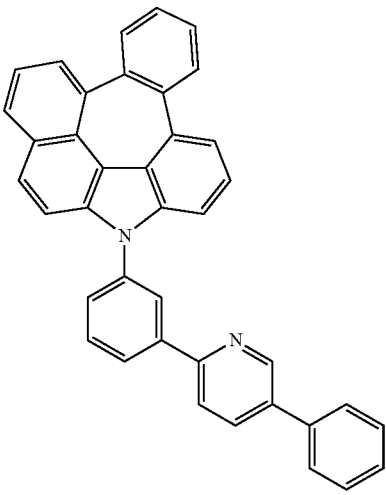
H-48
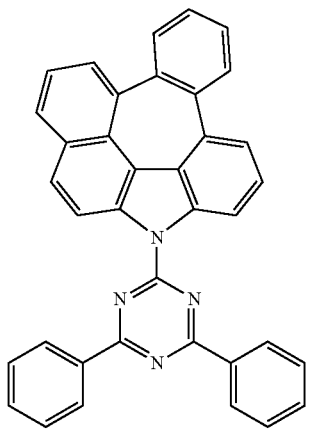
H-49
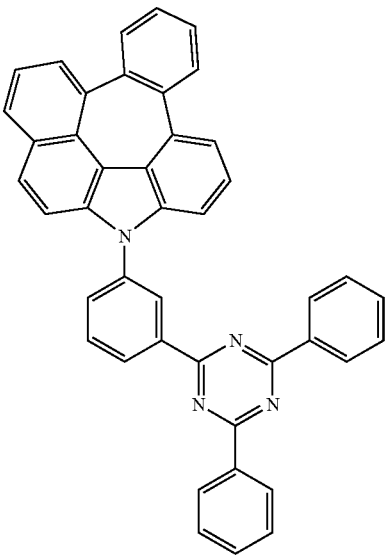

H-50
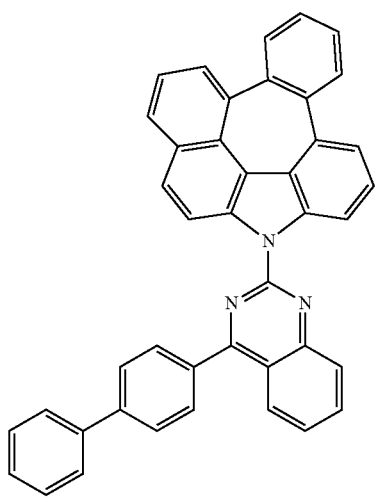
H-53
H-54
H-55
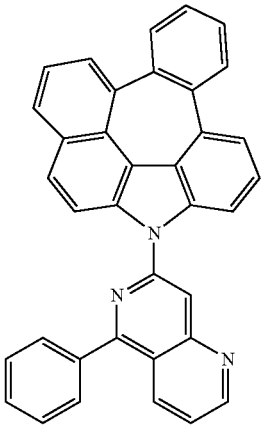
H-58
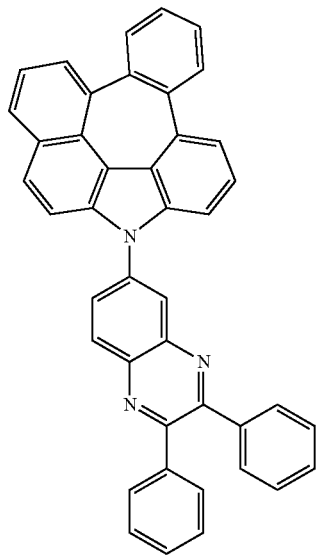
H-59
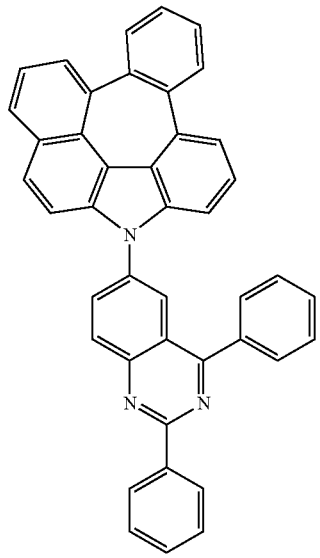

-continued
H-60
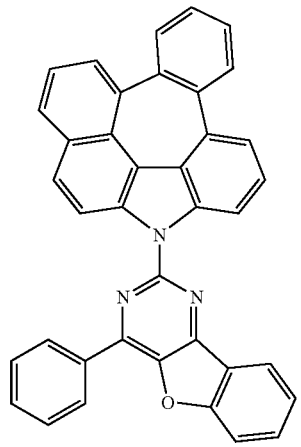
H-63
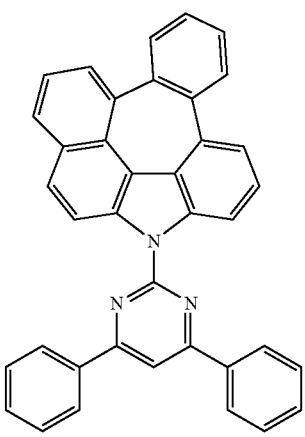
H-64
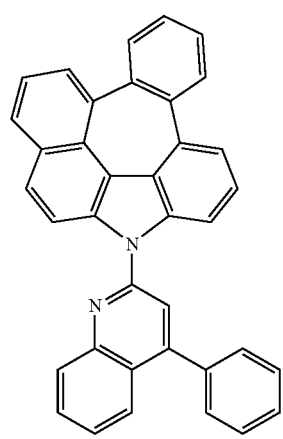
-continued
H-65
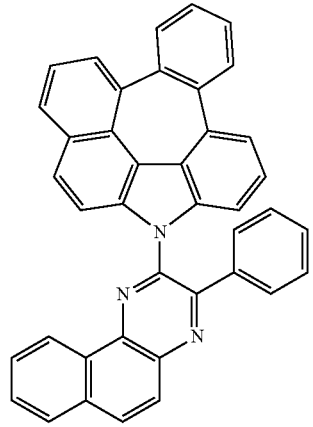
H-66
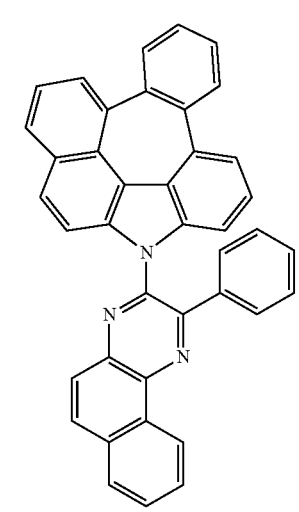
H-68
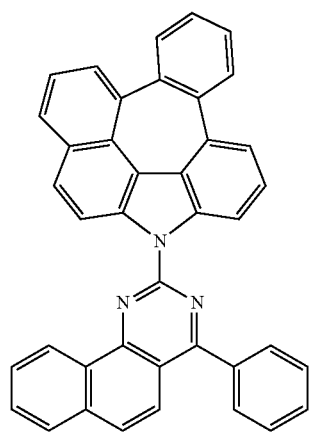

H-79
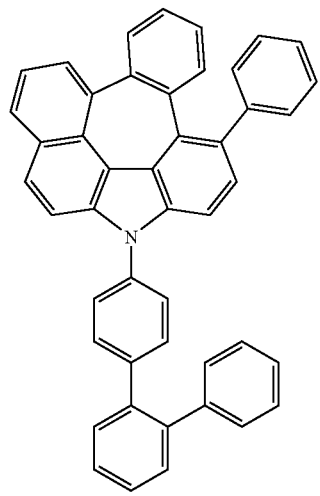
H-80
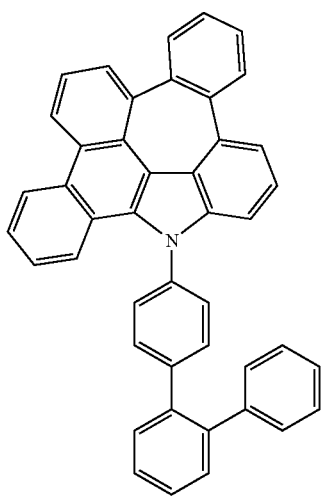
H-84
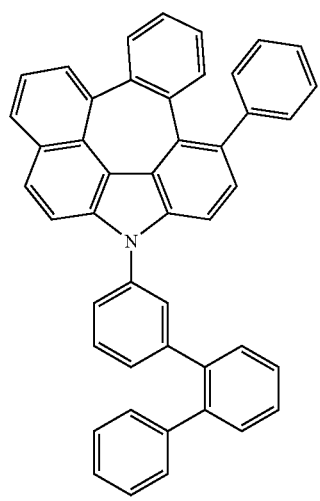
H-85
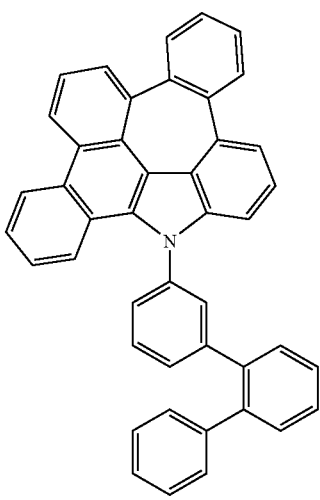
H-89
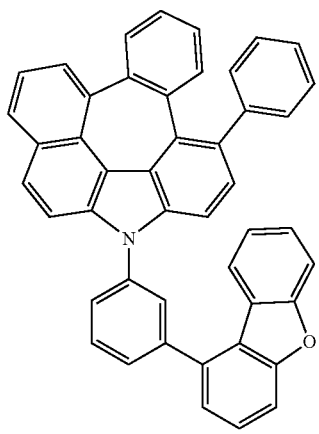
H-90
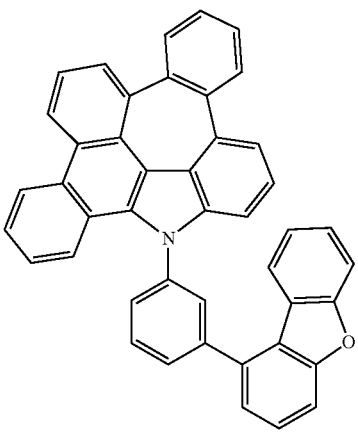

H-94
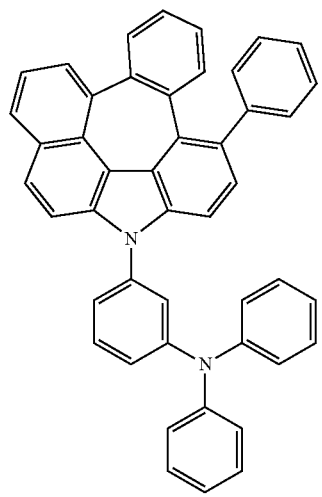
H-95
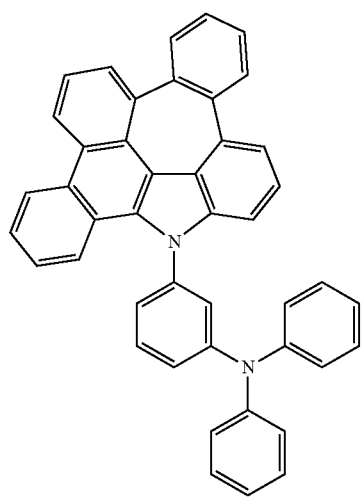
H-99
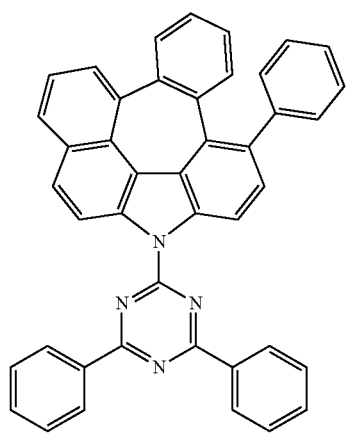
H-100
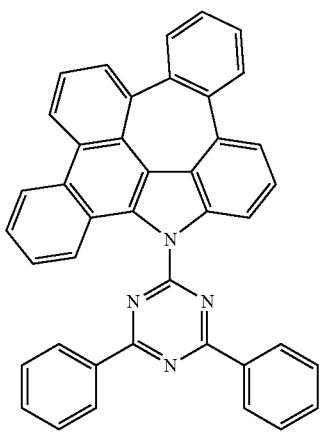
H-104
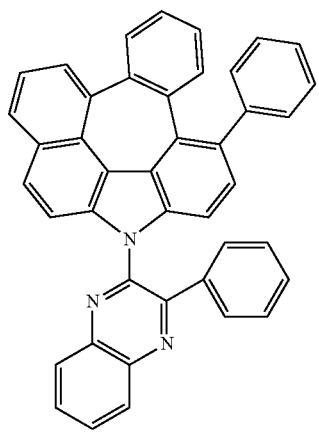
H-105
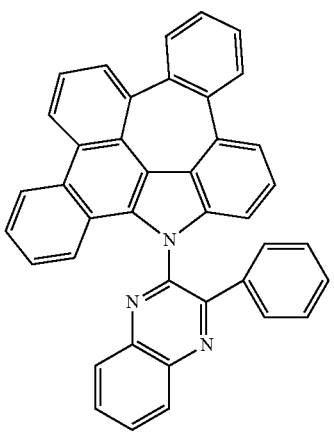

-continued
H-109
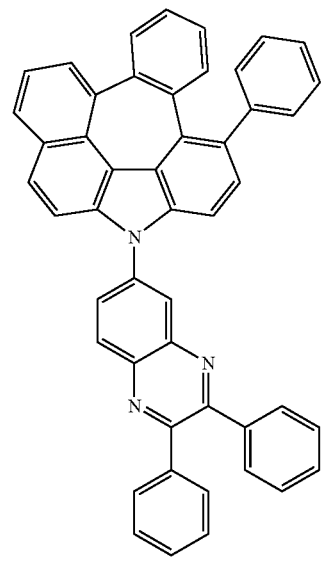
H-110
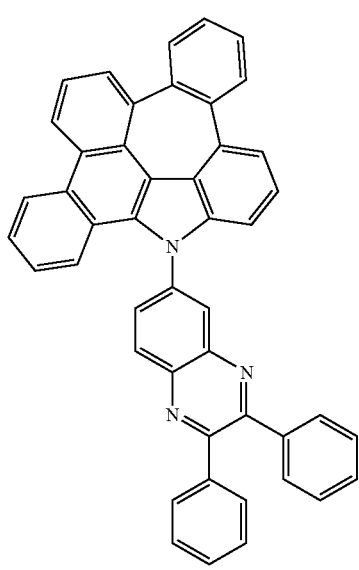
H-114
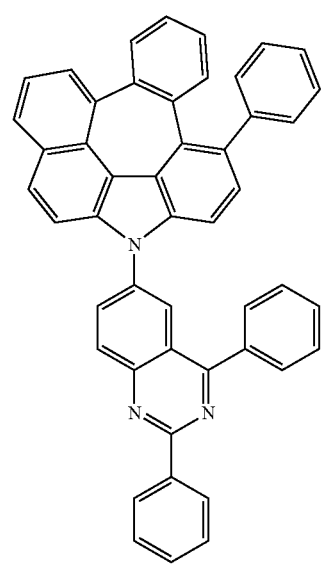
-continued
H-115
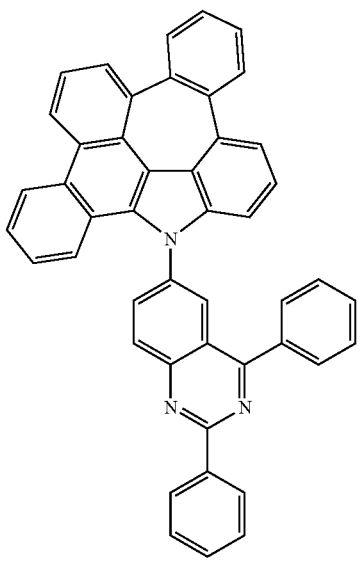
H-119
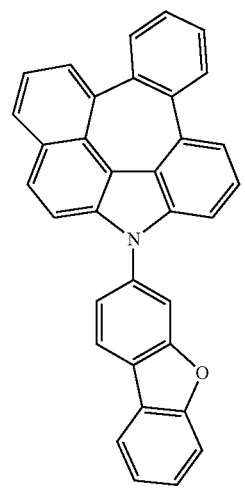
H-121
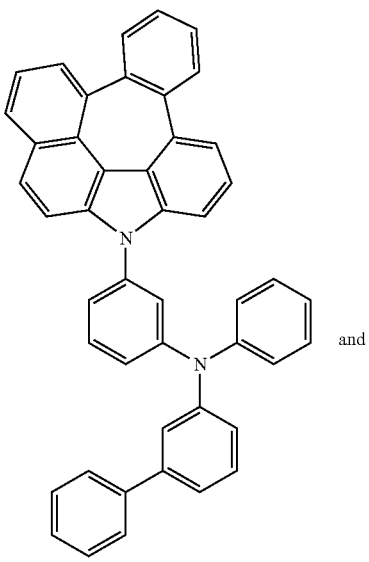
and H-122
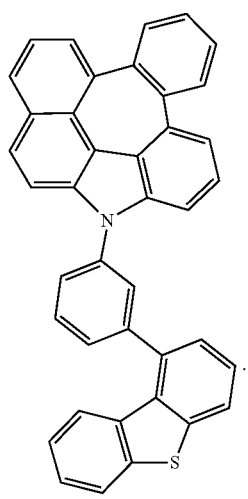
9. An organic electroluminescent device comprising an anode, a cathode, and at least one light-emitting layer between the anode and the cathode, wherein at least one layer of the light-emitting layers comprises the plurality of host materials according to claim 1.
* * * * *